United States Patent
Bartels et al.

(10) Patent No.: US 10,723,729 B2
(45) Date of Patent: *Jul. 28, 2020

(54) BACE1 INHIBITORS

(71) Applicant: Hoffmann-La Roche Inc., Little Falls, NJ (US)

(72) Inventors: Bjoern Bartels, Schopfheim (DE); Cosimo Dolente, Allschwil (CH); Wolfgang Guba, Muellheim (DE); Wolfgang Haap, Loerrach (DE); Ulrike Obst Sander, Reinach BL (CH); Jens-Uwe Peters, Grenzach-Wyhlen (DE); Thomas Woltering, Freiburg (DE)

(73) Assignee: Hoffmann-Le Roche Inc., Little Falls, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 16/512,905

(22) Filed: Jul. 16, 2019

(65) Prior Publication Data

US 2019/0337936 A1 Nov. 7, 2019

Related U.S. Application Data

(60) Continuation of application No. 16/033,785, filed on Jul. 12, 2018, now Pat. No. 10,399,969, which is a division of application No. 15/558,273, filed as application No. PCT/EP2016/055649 on Mar. 16, 2016, now Pat. No. 10,047,081.

(30) Foreign Application Priority Data

Mar. 20, 2015 (EP) .................................. 15160101

(51) Int. Cl.
*C07D 417/14* (2006.01)

(52) U.S. Cl.
CPC .................................. *C07D 417/14* (2013.01)

(58) Field of Classification Search
CPC .......................... C07D 487/04; C07D 417/14
USPC .......................................... 514/249; 544/48
See application file for complete search history.

(56) References Cited

U.S. PATENT DOCUMENTS

| 7,157,456 B2 | 1/2007 | Straub et al. |
| 10,047,081 B2* | 8/2018 | Bartels ................ C07D 417/14 |
| 10,399,969 B2* | 9/2019 | Bartels ................ C07D 417/14 |

FOREIGN PATENT DOCUMENTS

| WO | 2014062549 A1 | 4/2014 |
| WO | 2014114532 A1 | 7/2014 |

OTHER PUBLICATIONS

The English translation of the Russian Office Action, dated Jul. 4, 2019, in the related Russian Patent Application No. 2017134884/04(061153).
The English translation of the Japanese Office Action, dated Dec. 10, 2019, in the related Japanese Patent Application No. 2017-546991.

* cited by examiner

*Primary Examiner* — Kahsay Habte

(57) ABSTRACT

The present invention provides a compound of formula I, having BACE1 inhibitory activity, their manufacture, pharmaceutical compositions containing them and their use as therapeutically active substances. The active compounds of the present invention are useful in the therapeutic and/or prophylactic treatment of e.g. Alzheimer's disease.

19 Claims, No Drawings

BACE1 INHIBITORS

CROSS-REFERENCE TO RELATED APPLICATIONS

This application is a Continuation of U.S. patent application Ser. No. 16/033,785, filed Jul. 12, 2018, which in turn is a Divisional Application of U.S. patent application Ser. No. 15/558,273, filed Sep. 14, 2017, now U.S. Pat. No. 10,047,081, which in turns claims benefit from 371 National Stage Application of PCT/EP2016/055649, filed Mar. 16, 2016, which claims priority from European Patent Application No, 15160101 filed on Mar. 20, 2015, which are all hereby incorporated by reference in all of their entireties.

BACKGROUND ART

Alzheimer's disease (AD) is a neurodegenerative disorder of the central nervous system and the leading cause of a progressive dementia in the elderly population. Its clinical symptoms are impairment of memory, cognition, temporal and local orientation, judgment and reasoning but also severe emotional disturbances. There are currently no treatments available which can prevent the disease or its progression or stably reverse its clinical symptoms. AD has become a major health problem in all societies with high life expectancies and also a significant economic burden for their health systems.

AD is characterized by 2 major pathologies in the central nervous system (CNS), the occurrence of amyloid plaques and neurofibrillar tangles (Hardy et al., The amyloid hypothesis of Alzheimer's disease: progress and problems on the road to therapeutics, *Science.* 2002 Jul. 19; 297(5580):353-6, Selkoe, Cell biology of the amyloid beta-protein precursor and the mechanism of Alzheimer's disease, *Annu Rev Cell Biol.* 1994; 10:373-403). Both pathologies are also commonly observed in patients with Down's syndrome (trisomy 21), which also develop AD-like symptoms in early life. Neurofibrillar tangles are intracellular aggregates of the microtubule-associated protein tau (MAPT). Amyloid plaques occur in the extracellular space; their principal components are Aβ-peptides. The latter are a group of proteolytic fragments derived from the β-amyloid precursor protein (APP) by a series of proteolytic cleavage steps. Several forms of APP have been identified of which the most abundant are proteins of 695, 751 and 770 amino acids length. They all arise from a single gene through differential splicing. The Aβ-peptides are derived from the same domain of the APP but differ at their N- and C-termini, the main species are of 40 and 42 amino-acid length. There are several lines of evidence which strongly suggest that aggregated Aβ-peptides are the essential molecules in the pathogenesis of AD: 1) amyloid plaques formed of Aβ-peptides are invariably part of the AD pathology; 2) Aβ-peptides are toxic for neurons; 3) in Familial Alzheimer's Disease (FAD) the mutations in the disease genes APP, PSN1, PSN2 lead to increased levels of Aβ-peptides and early brain amyloidosis; 4) transgenic mice which express such FAD genes develop a pathology which bears many resemblances to the human disease. Aβ-peptides are produced from APP through the sequential action of 2 proteolytic enzymes termed β- and γ-secretase. β-Secretase cleaves first in the extracellular domain of APP approximately 28 amino acids outside of the transmembrane domain (TM) to produce a C-terminal fragment of APP containing the TM- and the cytoplasmatic domain (CTFβ). CTFβ is the substrate for γ-secretase which cleaves at several adjacent positions within the TM to produce the Aβ peptides and the cytoplasmic fragment. The γ-secretase is a complex of at least 4 different proteins, its catalytic subunit is very likely a presenilin protein (PSEN1, PSEN2). The β-secretase (BACE1, Asp2; BACE stands for β-site APP-cleaving enzyme) is an aspartyl protease which is anchored into the membrane by a transmembrane domain (Vassar et al., Beta-secretase cleavage of Alzheimer's amyloid precursor protein by the transmembrane aspartic protease BACE, *Science.* 1999 Oct. 22; 286(5440): 735). It is expressed in many tissues of the human organism but its level is especially high in the CNS. Genetic ablation of the BACE1 gene in mice has clearly shown that its activity is essential for the processing of APP which leads to the generation of Aβ-peptides, in the absence of BACE1 no Aβ-peptides are produced (Luo et al., Mice deficient in BACE1, the Alzheimer's beta-secretase, have normal phenotype and abolished beta-amyloid generation, *Nat Neurosci.* 2001 March; 4(3):231-2, Roberds et al., BACE knockout mice are healthy despite lacking the primary beta-secretase activity in brain: implications for Alzheimer's disease therapeutics, *Hum Mol Genet.* 2001 Jun. 1; 10(12): 1317-24). Mice which have been genetically engineered to express the human APP gene and which form extensive amyloid plaques and Alzheimer's disease like pathologies during aging fail to do so when β-secretase activity is reduced by genetic ablation of one of the BACE1 alleles (McConlogue et al., Partial reduction of BACE1 has dramatic effects on Alzheimer plaque and synaptic pathology in APP Transgenic Mice. *J Biol Chem.* 2007 Sep. 7; 282(36): 26326). It is thus presumed that inhibitors of BACE1 activity can be useful agents for therapeutic intervention in Alzheimer's disease (AD). Several patent applications have been filed describing BACE 1 inhibitors of various structures, e.g. WO2009103626, WO2010128058, WO2011020806, WO2011029803, WO2011069934, WO2011070029, WO2011138293, WO2012019966, WO2012028563, WO2012098064, WO2012104263, WO2012107371, WO2012110459, WO2012119883, WO2012126791, WO2012136603, WO2012139993, WO2012156284, WO2012163790, WO2012168164, WO2012168175, WO2013004676, WO2013041499, WO2013110622, WO2013174781, WO2014001228, WO2014114532, WO2014150331, WO2014150340 and WO2014150344. Further, WO2012139425 and WO2013028670 describe certain iminothiazines as BACE1 inhibitors.

Furthermore, the formation, or formation and deposition, of β-amyloid peptides in, on or around neurological tissue (e.g., the brain) are inhibited by the present compounds, i.e. inhibition of the Aβ-production from APP or an APP fragment.

The present invention provides novel compounds of formula I, their manufacture, medicaments based on a compound in accordance with the invention and their production as well as the use of compounds of formula I in the control or prevention of illnesses such as Alzheimer's disease.

FIELD OF THE INVENTION

The present invention provides 1-methylimino-1-oxo-2H-1,4-thiazin-amines having BACE1 inhibitory properties, their manufacture, pharmaceutical compositions containing them and their use as therapeutically active substances.

SUMMARY OF THE INVENTION

The present invention provides a compound of formula I,

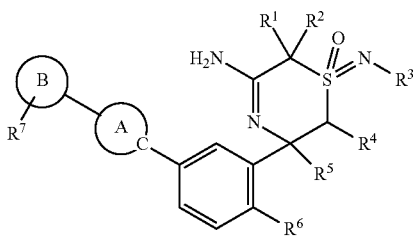

wherein the substituents and variables are as described below and in the claims, or a pharmaceutically acceptable salt thereof.

The present compounds have Asp2 (β-secretase, BACE1 or Memapsin-2) inhibitory activity and may therefore be used in the therapeutic and/or prophylactic treatment of diseases and disorders characterized by elevated β-amyloid levels and/or β-amyloid oligomers and/or β-amyloid plaques and further deposits, particularly Alzheimer's disease.

DETAILED DESCRIPTION OF THE INVENTION

The present invention provides a compound of formula I and their pharmaceutically acceptable salts thereof, the preparation of the above mentioned compounds, medicaments containing them and their manufacture as well as the use of the above mentioned compounds in the therapeutic and/or prophylactic treatment of diseases and disorders which are associated with inhibition of BACE1, such as Alzheimer's disease. Furthermore, the formation, or formation and deposition, of β-amyloid plaques in, on or around neurological tissue (e.g., the brain) are inhibited by the present compounds by inhibiting the Aβ production from APP or an APP fragment.

The following definitions of the general terms used in the present description apply irrespectively of whether the terms in question appear alone or in combination with other groups.

Unless otherwise stated, the following terms used in this Application, including the specification and claims, have the definitions given below. It must be noted that, as used in the specification and the appended claims, the singular forms "a", "an," and "the" include plural referents unless the context clearly dictates otherwise.

The term "$C_{1-6}$-alkyl", alone or in combination with other groups, stands for a hydrocarbon radical which may be linear or branched, with single or multiple branching, wherein the alkyl group in general comprises 1 to 6 carbon atoms, for example, methyl (Me), ethyl (Et), propyl, isopropyl (i-propyl), n-butyl, i-butyl (isobutyl), 2-butyl (sec-butyl), t-butyl (tert-butyl), isopentyl, 2-ethyl-propyl (2-methyl-propyl), 1,2-dimethyl-propyl and the like. Particular "$C_{1-6}$-alkyl" are "$C_{1-3}$-alkyl". Specific groups are methyl and ethyl. Most specific group is methyl.

The term "halogen-$C_{1-6}$-alkyl" or "$C_{1-6}$-alkyl-halogen", alone or in combination with other groups, refers to $C_{1-6}$-alkyl as defined herein, which is substituted by one or multiple halogen, particularly 1-5 halogen, more particularly 1-3 halogen. Particular halogen is fluoro. Particular "halogen-$C_{1-6}$-alkyl" is fluoro-$C_{1-6}$-alkyl and a particular "halogen-$C_{1-3}$-alkyl" is fluoro-$C_{1-3}$-alkyl. Examples are trifluoromethyl, difluoromethyl, fluoromethyl and the like. A specific group is fluoromethyl.

The term "cyano", alone or in combination with other groups, refers to N≡C—(NC—).

The term "halogen", alone or in combination with other groups, denotes chloro (Cl), iodo (I), fluoro (F) and bromo (Br). Particular "halogen" are Cl, I and F. A specific group is F.

The term "heteroaryl", alone or in combination with other groups, refers to an aromatic carbocyclic group of having a single 4 to 8 membered ring, in particular 5 to 8, or multiple condensed rings comprising 6 to 14, in particular 6 to 10 ring atoms and containing 1, 2 or 3 heteroatoms individually selected from N, O and S, in particular 1N or 2N, in which group at least one heterocyclic ring is aromatic. Examples of "heteroaryl" include benzofuryl, benzoimidazolyl, 1H-benzoimidazolyl, benzooxazinyl, benzoxazolyl, benzothiazinyl, benzothiazolyl, benzothienyl, benzotriazolyl, furyl, imidazolyl, indazolyl, 1H-indazolyl, indolyl, isoquinolinyl, isothiazolyl, isoxazolyl, oxazolyl, pyrazinyl, pyrazolyl (pyrazyl), 1H-pyrazolyl, pyrazolo[1,5-a]pyridinyl, pyridazinyl, pyridinyl (pyridyl), pyrimidinyl (pyrimidyl), pyrrolyl, quinolinyl, tetrazolyl, thiazolyl, thienyl, triazolyl, and the like. Particular "heteroaryl" groups are pyridyl, pyrazinyl and imidazo[1,2-a]pyridinyl. Examples of "5-membered-heteroaryl groups" include triazolyl, thienyl, furyl, imidazolyl, isothiazolyl, isoxazolyl, oxazolyl, pyrazolyl (pyrazyl), 1H-pyrazolyl, pyrrolyl, tetrazolyl, thiazolyl, triazolyl and the like. Particular "5-membered-heteroaryl groups" are isoxazolyl and triazolyl. Specific "5-membered-heteroaryl groups" are isoxazol-5-yl, isoxazol-3-yl, triazol-1-yl and triazol-4-yl. Examples of "6-membered-heteroaryl groups" include pyrazinyl, pyridazinyl, pyridinyl and pyrimidinyl. Particular "6-membered-heteroaryl groups" are pyrazinyl, pyridinyl and pyrimidinyl. Specific "6-membered-heteroaryl groups" are pyrazin-2-yl, pyridin-2-yl and pyrimidin-2-yl.

The term "pharmaceutically acceptable salts" refers to salts that are suitable for use in contact with the tissues of humans and animals. Examples of suitable salts with inorganic and organic acids are, but are not limited to acetic acid, citric acid, formic acid, fumaric acid, hydrochloric acid, lactic acid, maleic acid, malic acid, methane-sulfonic acid, nitric acid, phosphoric acid, p-toluenesulphonic acid, succinic acid, sulfuric acid (sulphuric acid), tartaric acid, trifluoroacetic acid and the like. Particular acids are formic acid, trifluoroacetic acid and hydrochloric acid. A specific acid is trifluoroacetic acid.

The term "amino", alone or in combination with other groups, refers to —$NH_2$.

The terms "hydroxyl" or "hydroxyl", alone or in combination with other groups, refer to —OH.

The term "$C_{2-6}$-alkynyl-$C_{1-6}$-alkoxy", alone or in combination with other groups, refers to $C_{1-6}$-alkoxy as defined herein, which is substituted by one or multiple $C_{2-6}$-alkynyl as defined herein, in particular 1 $C_{2-6}$-alkynyl.

The term "$C_{2-6}$-alkynyl", alone or in combination with other groups, denotes a monovalent linear or branched saturated hydrocarbon group of 2 to 6 carbon atoms, in particular from 2 to 4 carbon atoms, and comprising one, two or three triple bonds. Examples of $C_{2-6}$-alkynyl include ethynyl, propynyl, and n-butynyl.

The term "$C_{1-6}$-alkoxy-$C_{1-6}$-alkyl", alone or in combination with other groups, refers to $C_{1-6}$-alkyl as defined herein, which is substituted by one or multiple $C_{1-6}$-alkoxy, as defined herein, particularly 1 $C_{1-6}$-alkoxy. Particular "$C_{1-6}$- alkoxy-$C_{1-6}$-alkyl" is methoxy-$C_{1-6}$-alkyl. Examples are methoxymethyl, methoxyethyl and the like.

The term "$C_{1-6}$-alkoxy", alone or in combination with other groups, stands for an —O—$C_{1-6}$-alkyl radical which may be linear or branched, with single or multiple branching, wherein the alkyl group in general comprises 1 to 6 carbon atoms, for example, methoxy (OMe, MeO), ethoxy (OEt), propoxy, isopropoxy (i-propoxy), n-butoxy, i-butoxy (iso-butoxy), 2-butoxy (sec-butoxy), t-butoxy (tert-butoxy), isopentyloxy (i-pentyloxy) and the like. Particular "$C_{1-6}$-alkoxy" are groups with 1 to 4 carbon atoms. Specific are ethoxy and methoxy.

The term "halogen-$C_{1-6}$-alkoxy", alone or in combination with other groups, refers to $C_{1-6}$-alkoxy as defined herein, which is substituted by one or multiple halogens, in particular fluoro. Particular "halogen-$C_{1-6}$-alkoxy" are fluoro-$C_{1-6}$-alkoxy. Specific "halogen-$C_{1-6}$-alkoxy" are $CHF_2$—$CF_2$—$CH_2$—O—, $CHF_2$—O— and $CF_2$—O—.

The terms "pharmaceutically acceptable carrier" and "pharmaceutically acceptable auxiliary substance" refer to carriers and auxiliary substances such as diluents or excipients that are compatible with the other ingredients of the formulation.

The term "pharmaceutical composition" encompasses a product comprising specified ingredients in pre-determined amounts or proportions, as well as any product that results, directly or indirectly, from combining specified ingredients in specified amounts. Particularly it encompasses a product comprising one or more active ingredients, and an optional carrier comprising inert ingredients, as well as any product that results, directly or indirectly, from combination, complexation or aggregation of any two or more of the ingredients, or from dissociation of one or more of the ingredients, or from other types of reactions or interactions of one or more of the ingredients.

The term "inhibitor" denotes a compound which competes with, reduces or prevents the binding of a particular ligand to particular receptor or which reduces or prevents the inhibition of the function of a particular protein.

The term "half maximal inhibitory concentration" ($IC_{50}$) denotes the concentration of a particular compound required for obtaining 50% inhibition of a biological process in vitro. $IC_{50}$ values can be converted logarithmically to $pIC_{50}$ values (−log $IC_{50}$), in which higher values indicate exponentially greater potency. The $IC_{50}$ value is not an absolute value but depends on experimental conditions e.g. concentrations employed. The $IC_{50}$ value can be converted to an absolute inhibition constant (Ki) using the Cheng-Prusoff equation (Biochem. Pharmacol. (1973) 22:3099). The term "inhibition constant" (Ki) denotes the absolute binding affinity of a particular inhibitor to a receptor. It is measured using competition binding assays and is equal to the concentration where the particular inhibitor would occupy 50% of the receptors if no competing ligand (e.g. a radioligand) was present. Ki values can be converted logarithmically to pKi values (−log Ki), in which higher values indicate exponentially greater potency.

"Therapeutically effective amount" means an amount of a compound that, when administered to a subject for treating a disease state, is sufficient to effect such treatment for the disease state. The "therapeutically effective amount" will vary depending on the compound, disease state being treated, the severity or the disease treated, the age and relative health of the subject, the route and form of administration, the judgment of the attending medical or veterinary practitioner, and other factors.

The term "as defined herein" and "as described herein" when referring to a variable incorporates by reference the broad definition of the variable as well as particularly, more particularly and most particularly definitions, if any.

The terms "treating", "contacting" and "reacting" when referring to a chemical reaction means adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

The term "aromatic" denotes the conventional idea of aromaticity as defined in the literature, in particular in IUPAC—Compendium of Chemical Terminology, 2nd, A. D. McNaught and A. Wilkinson (Eds). Blackwell Scientific Publications, Oxford (1997).

The term "pharmaceutically acceptable excipient" denotes any ingredient having no therapeutic activity and being non-toxic such as disintegrators, binders, fillers, solvents, buffers, tonicity agents, stabilizers, antioxidants, surfactants or lubricants used in formulating pharmaceutical products.

Whenever a chiral carbon is present in a chemical structure, it is intended that all stereoisomers associated with that chiral carbon are encompassed by the structure as pure stereoisomers as well as mixtures thereof.

The invention also provides pharmaceutical compositions, methods of using, and methods of preparing the aforementioned compounds.

All separate embodiments may be combined.

One embodiment of the invention provides a compound of formula I,

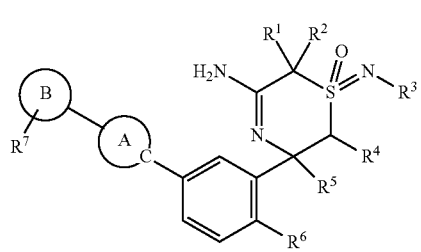

A is a heteroaryl group,
B is a heteroaryl group,
R is selected from the group consisting of
   i) $C_{1-6}$-alkyl and
   ii) halogen-$C_{1-6}$-alkyl;
$R^2$ is selected from the group consisting of
   i) $C_{1-6}$-alkyl, and
   ii) halogen-$C_{1-6}$-alkyl;
or $R^1$ and $R^2$ form together with the C-atom they are attached to, a $C_{3-6}$-cycloalkyl-, wherein the $C_{3-6}$-cycloalkyl- is optionally substituted by one or more substituents selected from the group consisting of halogen and hydroxyl;
$R^3$ is selected from the group consisting of
   i) hydrogen,
   ii) $C_{3-6}$-cycloalkyl,
   iii) halogen-$C_{1-6}$-alkyl, and
   iv) $C_{1-6}$-alkyl;

$R^4$ is selected from the group consisting of
  i) hydrogen, and
  ii) $C_{1-6}$-alkyl;
$R^5$ is selected from the group consisting of
  i) $C_{1-6}$-alkyl, and
  ii) halogen-$C_{1-6}$-alkyl;
$R^6$ is halogen;
$R^7$ is selected from the group consisting of
  i) amino,
  ii) cyano,
  iii) hydrogen,
  iv) OH,
  v) halogen,
  vi) $C_{1-6}$-alkyl,
  vii) $C_{1-6}$-alkyl-$C_{3-6}$-cycloalkyl,
  viii) halogen-$C_{1-6}$-alkyl,
  ix) $C_{1-6}$-alkoxy-$C_{1-6}$-alkyl,
  x) $C_{2-6}$-alkynyl,
  xi) $C_{2-6}$-alkynyl-$C_{1-6}$-alkyl,
  xii) $C_{2-6}$-alkynyl-$C_{1-6}$-alkoxy
  xiii) $C_{1-6}$-alkoxy, and
  xiv) halogen-$C_{1-6}$-alkoxy;
or pharmaceutically acceptable salts thereof.

A certain embodiment of the invention provides a compound of formula I, wherein
A is a heteroaryl group,
B is a heteroaryl group,
$R^1$ is selected from the group consisting of
  i) $C_{1-6}$-alkyl and
  ii) halogen-$C_{1-6}$-alkyl;
$R^2$ is selected from the group consisting of
  i) $C_{1-6}$-alkyl, and
  ii) halogen-$C_{1-6}$-alkyl;
or $R^1$ and $R^2$ form together with the C-atom they are attached to, a $C_{3-6}$-cycloalkyl-, wherein the $C_{3-6}$-cycloalkyl- is optionally substituted by one or more substituents selected from the group consisting of halogen and hydroxyl;
$R^3$ is selected from the group consisting of
  i) hydrogen,
  ii) halogen-$C_{1-6}$-alkyl, and
  iii) $C_{1-6}$-alkyl;
$R^4$ is selected from the group consisting of
  i) hydrogen, and
  ii) $C_{1-6}$-alkyl;
$R^5$ is selected from the group consisting of
  i) $C_{1-6}$-alkyl, and
  ii) halogen-$C_{1-6}$-alkyl;
$R^6$ is halogen;
$R^7$ is selected from the group consisting of
  i) amino,
  ii) cyano,
  iii) hydrogen,
  iv) halogen,
  v) $C_{1-6}$-alkyl,
  vi) halogen-$C_{1-6}$-alkyl,
  vii) $C_{1-6}$-alkoxy-$C_{1-6}$-alkyl,
  viii) $C_{2-6}$-alkynyl,
  ix) $C_{2-6}$-alkynyl-$C_{1-6}$-alkyl,
  x) $C_{2-6}$-alkynyl-$C_{1-6}$-alkoxy
  xi) $C_{1-6}$-alkoxy, and
  xii) halogen-$C_{1-6}$-alkoxy;
or pharmaceutically acceptable salts thereof.

A certain embodiment of the invention provides a compound of formula I, which is of formula Ia, wherein A, B, $R^1$, $R^2$, $R^3$, $R^4$, $R^5$, $R^6$ and $R^7$ are as defined herein

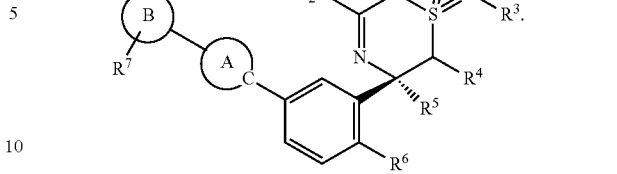

A certain embodiment of the invention provides a compound of formula I as described herein, wherein A is a 5-membered heteroaryl group.

A certain embodiment of the invention provides a compound of formula I as described herein, wherein A is isoxazolyl or triazolyl.

A certain embodiment of the invention provides a compound of formula I as described herein, wherein B is a 6-membered heteroaryl group.

A certain embodiment of the invention provides a compound of formula I as described herein, wherein B is pyrimidinyl, pyrazinyl or pyridinyl.

A certain embodiment of the invention provides a compound of formula T as described herein, wherein $R^1$ is $C_{1-6}$-alkyl.

A certain embodiment of the invention provides a compound of formula I as described herein, wherein $R^1$ is methyl.

A certain embodiment of the invention provides a compound of formula I as described herein, wherein $R^2$ is $C_{1-6}$-alkyl.

A certain embodiment of the invention provides a compound of formula I as described herein, wherein $R^2$ is methyl.

A certain embodiment of the invention provides a compound of formula I as described herein, wherein $R^1$ and $R^2$ form together with the C-atom they are attached to a $C_{3-6}$-cycloalkyl-.

A certain embodiment of the invention provides a compound of formula I as described herein, wherein $R^1$ and $R^2$ form together with the C-atom they are attached to a cyclopentyl.

A certain embodiment of the invention provides a compound of formula I as described herein, wherein $R^3$ is $C_{1-6}$-alkyl.

A certain embodiment of the invention provides a compound of formula I as described herein, wherein $R^3$ is methyl.

A certain embodiment of the invention provides a compound of formula I as described herein, wherein $R^3$ is H, $CH_3$, $CD_3$, $CH_2CF_3$ or cyclopropyl.

A certain embodiment of the invention provides a compound of formula I as described herein, wherein $R^4$ is hydrogen.

A certain embodiment of the invention provides a compound of formula I as described herein, wherein $R^5$ is $C_{1-6}$-alkyl or halogen-$C_{1-6}$-alkyl.

A certain embodiment of the invention provides a compound of formula I as described herein, wherein $R^5$ is methyl or —$CH_2F$.

A certain embodiment of the invention provides a compound of formula I as described herein, wherein $R^5$ is methyl.

A certain embodiment of the invention provides a compound of formula I as described herein, wherein $R^5$ is —CH$_2$F.

A certain embodiment of the invention provides a compound of formula I as described herein, wherein $R^6$ is F.

A certain embodiment of the invention provides a compound of formula T as described herein, wherein $R^7$ is Br, CH$_2$-cyclopropyl, Cl, CN, Et, Me, OCH$_2$CF$_2$CHF$_2$, OCH$_2$CF$_3$, OCH$_2$CHF$_2$, OH or OMe.

A certain embodiment of the invention provides a compound of formula I as described herein, wherein $R^7$ is selected from the group consisting of cyano, halogen, C$_{1-6}$-alkoxy and halogen-C$_{1-6}$-alkoxy.

A certain embodiment of the invention provides a compound of formula I as described herein, wherein $R^7$ is selected from the group consisting of chloro, cyano, methoxy and 2,2-difluoroethoxy.

A certain embodiment of the invention provides a compound of formula T as described herein, wherein A is a 5-membered heteroaryl group, B is a 6-membered heteroaryl group, $R^1$ is methyl, $R^2$ is methyl, $R^3$ is methyl, $R^4$ is hydrogen, $R^5$ is methyl or —CH$_2$F, $R^6$ is F and $R^7$ is selected from the group consisting of cyano, halogen, C$_{1-6}$-alkoxy and halogen-C$_{1-6}$-alkoxy.

A certain embodiment of the invention provides a compound of formula I as described herein, wherein A is selected from the group consisting of isoxazolyl and triazolyl, B is selected from the group consisting of pyrimidinyl, pyrazinyl and pyridinyl, $R^1$ is methyl, $R^2$ is methyl, $R^3$ is methyl, $R^4$ is hydrogen, $R^5$ is methyl or —CH$_2$F, $R^6$ is F and $R^7$ is selected from the group consisting of cyano, halogen, C$_{1-6}$-alkoxy and halogen-C$_{1-6}$-alkoxy.

A certain embodiment of the invention provides a compound of formula I as described herein that is selected from the group consisting of (1R,3R)-3-[2-fluoro-5-[3-(5-methoxypyrazin-2-yl)isoxazol-5-yl]phenyl]-3,6,6-trimethyl-1-methylimino-1-oxo-2H-1,4-thiazin-5-amine;2,2,2-trifluoroacetic acid, (1R,3R)-3-[2-fluoro-5-[3-(5-methoxypyrazin-2-yl)isoxazol-5-yl]phenyl]-3,6,6-trimethyl-1-oxo-1-(trideuteriomethylimino)-2H-1,4-thiazin-5-amine 2,2,2-trifluoroacetate, (1R,3R)-3-[2-fluoro-5-[3-[5-(2,2,3,3-tetrafluoropropoxy)pyrimidin-2-yl]isoxazol-5-yl]phenyl]-3,6,6-trimethyl-1-oxo-1-(trideuteriomethylimino)-2H-1,4-thiazin-5-amine 2,2,2-trifluoroacetate, (1R,3R)-3-[5-[1-(5-chloro-2-pyridyl)triazol-4-yl]-2-fluorophenyl]-3,6,6-trimethyl-1-methylimino-1-oxo-2H-1,4-thiazin-5-amine;2,2,2-trifluoroacetic acid, (1R,3R)-3-[5-[3-(5-chloropyrimidin-2-yl)isoxazol-5-yl]-2-fluoro-phenyl]-3,6,6-trimethyl-1-methylimino-1-oxo-2H-1,4-thiazin-5-amine;2,2,2-trifluoroacetic acid, (1R,3R)-3-[5-[3-(5-chloropyrimidin-2-yl)isoxazol-5-yl]-2-fluoro-phenyl]-1-cyclopropylimino-3,6,6-trimethyl-1-oxo-2H-1,4-thiazin-5-amine 2,2,2-trifluoroacetate, (1R,3R)-3-[5-[3-(5-chloropyrimidin-2-yl)isoxazol-5-yl]-2-fluoro-phenyl]-1-imino-3,6,6-trimethyl-1-oxo-2H-1,4-thiazin-5-amine;2,2,2-trifluoroacetic acid 2,2,2-trifluoroacetate, (1R,3R)-3-[5-[3-(5-ethylpyrimidin-2-yl)isoxazol-5-yl]-2-fluoro-phenyl]-3,6,6-trimethyl-1-oxo-1-(trideuteriomethylimino)-2H-1,4-thiazin-5-amine 2,2,2-trifluoroacetate, (1R,3R)-3-[5-[3-[5-(2,2-difluoroethoxy)pyrazin-2-yl]isoxazol-5-yl]-2-fluoro-phenyl]-3,6,6-trimethyl-1-methylimino-1-oxo-2H-1,4-thiazin-5-amine;2,2,2-trifluoroacetic acid, (1R,3R)-3-[5-[3-[5-(2,2-difluoroethoxy)pyrimidin-2-yl]isoxazol-5-yl]-2-fluoro-phenyl]-3,6,6-trimethyl-1-methylimino-1-oxo-2H-1,4-thiazin-5-amine, (1R,3R)-5-amino-1-(cyclopropylimino)-3-(2-fluoro-5-(3-(5-methoxypyrazin-2-yl)isoxazol-5-yl)phenyl)-3,6,6-trimethyl-3,6-dihydro-2H-1,4-thiazine 1-oxide, (1R,3R)-5-amino-3-(2-fluoro-5-(3-(5-(2,2,2-trifluoroethoxy)pyrazin-2-yl)isoxazol-5-yl)phenyl)-3,6,6-trimethyl-1-(methylimino)-3,6-dihydro-2H-1,4-thiazine 1-oxide 2,2,2-trifluoroacetate, (1R,3R)-5-amino-3-(2-fluoro-5-(3-(5-hydroxypyrazin-2-yl)isoxazol-5-yl)phenyl)-3,6,6-trimethyl-1-(methylimino)-3,6-dihydro-2H-1,4-thiazine 1-oxide, (1R,3R)-5-amino-3-(2-fluoro-5-(3-(5-methoxypyrazin-2-yl)isoxazol-5-yl)phenyl)-3,6,6-trimethyl-1-((2,2,2-trifluoroethyl)imino)-3,6-dihydro-2H-1,4-thiazine 1-oxide 2,2,2-trifluoroacetate, (1R,3R)-5-amino-3-(2-fluoro-5-(3-(5-methoxypyrazin-2-yl)isoxazol-5-yl)phenyl)-1-imino-3,6,6-trimethyl-3,6-dihydro-2H-1,4-thiazine 1-oxide, (1R,3R)-5-amino-3-(2-fluoro-5-(3-(5-methoxypyrimidin-2-yl)isoxazol-5-yl)phenyl)-3,6,6-trimethyl-1-(methylimino)-3,6-dihydro-2H-1,4-thiazine 1-oxide, (1R,3R)-5-amino-3-(5-(3-(5-(cyclopropylmethoxy)pyrazin-2-yl)isoxazol-5-yl)-2-fluorophenyl)-3,6,6-trimethyl-1-(methylimino)-3,6-dihydro-2H-1,4-thiazine 1-oxide, (1R,3R)-5-amino-3-(5-(3-(5-chloropyrimidin-2-yl)isoxazol-5-yl)-2-fluorophenyl)-3,6,6-trimethyl-1-((2,2,2-trifluoroethyl)imino)-3,6-dihydro-2H-1,4-thiazine 1-oxide 2,2,2-trifluoroacetate, (1R,3S)-3-[2-fluoro-5-[3-(5-methoxypyrimidin-2-yl)isoxazol-5-yl]phenyl]-3-(fluoromethyl)-6,6-dimethyl-1-methylimino-1-oxo-2H-1,4-thiazin-5-amine, (1R,3S)-5-amino-3-(5-(1-(5-chloropyridin-2-yl)-1H-1,2,3-triazol-4-yl)-2-fluorophenyl)-3-(fluoromethyl)-6,6-dimethyl-1-(methylimino)-3,6-dihydro-2H-1,4-thiazine 1-oxide 2,2,2-trifluoroacetate, (1R,3S)-5-amino-3-(5-(3-(5-(2,2-difluoroethoxy)pyrazin-2-yl)isoxazol-5-yl)-2-fluorophenyl)-3-(fluoromethyl)-6,6-dimethyl-1-(methylimino)-3,6-dihydro-2H-1,4-thiazine 1-oxide 2,2,2-trifluoroacetate, (1R,3S)-5-amino-3-(5-(3-(5-bromo-3-methylpyridin-2-yl)isoxazol-5-yl)-2-fluorophenyl)-3-(fluoromethyl)-6,6-dimethyl-1-(methylimino)-3,6-dihydro-2H-1,4-thiazine 1-oxide 2,2,2-trifluoroacetate, (1R,3S)-5-amino-3-(5-(3-(5-chloropyrimidin-2-yl)isoxazol-5-yl)-2-fluorophenyl)-3-(fluoromethyl)-6,6-dimethyl-1-(methylimino)-3,6-dihydro-2H-1,4-thiazine 1-oxide 2,2,2-trifluoroacetate, (1S,3R)-3-[2-fluoro-5-[3-(5-methoxypyrazin-2-yl)isoxazol-5-yl]phenyl]-1-imino-3,6,6-trimethyl-1-oxo-2H-1,4-thiazin-5-amine 2,2,2-trifluoroacetate, (1S,3R)-3-[5-[3-(5-chloropyrimidin-2-yl)isoxazol-5-yl]-2-fluoro-phenyl]-1-imino-3,6,6-trimethyl-1-oxo-2H-1,4-thiazin-5-amine 2,2,2-trifluoroacetate, (1S,3R)-3-[5-[3-[5-(2,2-difluoroethoxy)pyrimidin-2-yl]isoxazol-5-yl]-2-fluoro-phenyl]-3,6,6-trimethyl-1-methylimino-1-oxo-2H-1,4-thiazin-5-amine, (1S,3R)-5-amino-1-(cyclopropylimino)-3-(2-fluoro-5-(3-(5-methoxypyrazin-2-yl)isoxazol-5-yl)phenyl)-3,6,6-trimethyl-3,6-dihydro-2H-1,4-thiazine 1-oxide 2,2,2-trifluoroacetate, (1S,3R)-5-amino-3-(2-fluoro-5-(3-(5-methoxypyrazin-2-yl)isoxazol-5-yl)phenyl)-3,6,6-trimethyl-1-((2,2,2-trifluoroethyl)imino)-3,6-dihydro-2H-1,4-thiazine 1-oxide 2,2,2-trifluoroacetate, (1S,3R)-5-amino-3-(5-(3-(5-(2,2-difluoroethoxy)pyrazin-2-yl)isoxazol-5-yl)-2-fluorophenyl)-3,6,6-trimethyl-1-(methylimino)-3,6-dihydro-2H-1,4-thiazine 1-oxide 2,2,2-trifluoroacetate, (1S,3R)-5-amino-3-(5-(3-(5-chloropyrimidin-2-yl)isoxazol-5-yl)-2-fluorophenyl)-3,6,6-trimethyl-1-(methylimino)-3,6-dihydro-2H-1,4-thiazine 1-oxide 2,2,2-trifluoroacetate, (1S,3R)-5-amino-3-(5-(3-(5-chloropyrimidin-2-yl)isoxazol-5-yl)-2-fluorophenyl)-1-(cyclopropylimino)-3,6,6-trimethyl-3,6-dihydro-2H-1,4-thiazine 1-oxide 2,2,2-trifluoroacetate, (1S,3R)-5-amino-3-(5-(3-(5-chloropyrimidin-2-yl)isoxazol-5-yl)-2-fluorophenyl)-3,6,6-trimethyl-1-((2,2,2-trifluoroethyl)imino)-3,6-dihydro-2H-1,4-thiazine 1-oxide 2,2,2-trifluoroacetate, (1S,3S)-3-[2-fluoro-5-[3-(5-methoxypyrazin-2-yl)isoxazol-5-yl]phenyl]-3-(fluoromethyl)-6,6-dimethyl-1-methylimino-1-oxo-2H-1,4-thiazin-5-amine;2,2,2-trifluoroacetic acid, (1S,3S)-3-[5-[3-(5-chloropyrimidin-2-yl)isoxazol-5-yl]-2-fluoro-phenyl]-3-(fluoromethyl)-6,6-dimethyl-1-methylimino-1-oxo-2H-1,4-thiazin-5-amine;2,2,2-trifluoroacetic acid, (1S,3S)-5-amino-3-(2-fluoro-5-(3-(5-methoxypyrimidin-2-yl)isoxazol-5-yl)phenyl)-3-(fluoromethyl)-6,6-dimethyl-1-(methylimino)-3,6-dihydro-2H-1,4-thiazine 1-oxide, (6R,8R)-10-amino-8-(2-fluoro-5-(3-(5-methoxypyrazin-2-yl)isoxazol-5-yl)phenyl)-8-methyl-6-(methylimino)-6-thia-9-azaspiro[4.5]dec-9-ene 6-oxide 2,2,2-trifluoroacetate, (6R,8R)-10-amino-8-(2-fluoro-5-(3-(5-methoxypyrimidin-2-yl)isoxazol-5-yl)phenyl)-8-methyl-6-(methylimino)-6-thia-9-azaspiro[4.5]dec-9-ene 6-oxide 2,2,2-trifluoroacetate, (6R,8R)-10-amino-8-(5-(3-(5-(2,2-difluoroethoxy)pyrazin-2-yl)isoxazol-5-yl)-2-fluorophenyl)-8-methyl-6-(methylimino)-6-thia-9-azaspiro[4.5]dec-9-ene 6-oxide, (6R,8R)-10-amino-8-(5-(3-(5-chloropyrimidin-2-yl)isoxazol-5-yl)-2-fluorophenyl)-8-methyl-6-(methylimino)-6-thia-9-azaspiro[4.5]dec-9-ene 6-oxide 2,2,2-trifluoroacetate, (6S,8R)-10-amino-8-(2-fluoro-5-(3-(5-methoxypyrazin-2-yl)isoxazol-5-yl)phenyl)-8-methyl-6-(methylimino)-6-thia-9-azaspiro[4.5]dec-9-ene 6-oxide 2,2,2-trifluoroacetate, (6S,8R)-10-amino-8-(5-(3-(5-chloropyrimidin-2-yl)isoxazol-5-yl)-2-fluorophenyl)-8-methyl-6-(methylimino)-6-thia-9-azaspiro[4.5]dec-9-ene 6-oxide 2,2,2-trifluoroacetate, 2-[5-[3-[(1R,3R)-5-amino-3,6,6-trimethyl-1-methylimino-1-oxo-2H-1,4-thiazin-3-yl]-4-fluoro-phenyl]isoxazol-3-yl]pyrimidine-5-carbonitrile;2,2,2-trifluoroacetic acid, 6-(4-(3-((1R,3S)-5-amino-3-(fluoromethyl)-6,6-dimethyl-1-(methylimino)-1-oxido-3,6-dihydro-2H-1,4-thiazin-3-yl)-4-fluorophenyl)-1H-1,2,3-triazol-1-yl)nicotinonitrile 2,2,2-trifluoroacetate, and 6-[4-[3-[(1R,3R)-5-amino-3,6,6-trimethyl-1-methylimino-1-oxo-2H-1,4-thiazin-3-yl]-4-fluoro-phenyl]triazol-1-yl]pyridine-3-carbonitrile 2,2,2-trifluoroacetic acid.

A certain embodiment of the invention provides a compound of formula I as described herein that is selected from the group consisting of (1R,3R)-3-[2-fluoro-5-[3-(5-methoxypyrazin-2-yl)isoxazol-5-yl]phenyl]-3,6,6-trimethyl-1-methylimino-1-oxo-2H-1,4-thiazin-5-amine trifluoroacetate, (1R,3R)-3-[5-[1-(5-chloro-2-pyridyl)triazol-4-yl]-2-fluoro-phenyl]-3,6,6-trimethyl-1-methylimino-1-oxo-2H-1,4-thiazin-5-amine trifluoroacetate, (1R,3R)-3-[5-[3-(5-chloropyrimidin-2-yl)isoxazol-5-yl]-2-fluoro-phenyl]-3,6,6-trimethyl-1-methylimino-1-oxo-2H-1,4-thiazin-5-amine trifluoroacetate, (1R,3R)-3-[5-[3-[5-(2,2-difluoroethoxy)pyrazin-2-yl]isoxazol-5-yl]-2-fluoro-phenyl]-3,6,6-trimethyl-1-methylimino-1-oxo-2H-1,4-thiazin-5-amine trifluoroacetate, (1R,3S)-5-amino-3-(5-(3-(5-(2,2-difluoroethoxy)pyrazin-2-yl)isoxazol-5-yl)-2-fluorophenyl)-3-(fluoromethyl)-6,6-dimethyl-1-(methylimino)-3,6-dihydro-2H-1,4-thiazine 1-oxide trifluoroacetate, (1R,3S)-5-amino-3-(5-(3-(5-chloropyrimidin-2-yl)isoxazol-5-yl)-2-fluorophenyl)-3-(fluoromethyl)-6,6-dimethyl-1-(methylimino)-3,6-dihydro-2H-1,4-thiazine 1-oxide trifluoroacetate, (1S,3R)-5-amino-3-(5-(3-(5-(2,2-difluoroethoxy)pyrazin-2-yl)isoxazol-5-yl)-2-fluorophenyl)-3,6,6-trimethyl-1-(methylimino)-3,6-dihydro-2H-1,4-thiazine 1-oxide trifluoroacetate, (1S,3R)-5-amino-3-(5-(3-(5-chloropyrimidin-2-yl)isoxazol-5-yl)-2-fluorophenyl)-3,6,6-trimethyl-1-(methylimino)-3,6-dihydro-2H-1,4-thiazine 1-oxide trifluoroacetate, (1S,3S)-3-[2-fluoro-5-[3-(5-methoxypyrazin-2-yl)isoxazol-5-yl]phenyl]-3-(fluoromethyl)-6,6-dimethyl-1-methylimino-1-oxo-2H-1,4-thiazin-5-amine trifluoroacetate, (1S,3S)-3-[5-[3-(5-chloropyrimidin-2-yl)isoxazol-5-yl]-2-fluoro-phenyl]-3-(fluoromethyl)-6,6-dimethyl-1-methylimino-1-oxo-2H-1,4-thiazin-5-amine trifluoroacetate, 2-[5-[3-[(1R,3R)-5-amino-3,6,6-trimethyl-1-methylimino-1-oxo-2H-1,4-thiazin-3-yl]-4-fluoro-phenyl]isoxazol-3-yl]pyrimidine-5-carbonitrile trifluoroacetate, and 6-[4-[3-[(1R,3R)-5-amino-3,6,6-trimethyl-1-methylimino-1-oxo-2H-1,4-thiazin-3-yl]-4-fluoro-phenyl]triazol-1-yl]pyridine-3-carbonitrile trifluoroacetate.

A certain embodiment of the invention provides a compound of formula T as described herein that is selected from the group consisting of (1R,3R)-3-[5-[3-[5-(2,2-difluoroethoxy)pyrazin-2-yl]isoxazol-5-yl]-2-fluoro-phenyl]-3,6,6-trimethyl-1-methylimino-1-oxo-2H-1,4-thiazin-5-amine;2,2,2-trifluoroacetic acid (1R,3R)-3-[5-[3-(5-chloropyrimidin-2-yl)isoxazol-5-yl]-2-fluoro-phenyl]-3,6,6-trimethyl-1-methylimino-1-oxo-2H-1,4-thiazin-5-amine;2,2,2-trifluoroacetic acid (1R,3R)-3-[2-fluoro-5-[3-(5-methoxypyrazin-2-yl)isoxazol-5-yl]phenyl]-3,6,6-trimethyl-1-methylimino-1-oxo-2H-1,4-thiazin-5-amine;2,2,2-trifluoroacetic acid and (1R,3R)-3-[2-fluoro-5-[3-(5-methoxypyrazin-2-yl)isoxazol-5-yl]phenyl]-3,6,6-trimethyl-1-oxo-1-(trideuteriomethylimino)-2H-1,4-thiazin-5-amine 2,2,2-trifluoroacetate.

A certain embodiment of the invention provides a compound of formula I as described herein that is selected from the group consisting of (1R,3R)-3-[5-[3-[5-(2,2-difluoroethoxy)pyrazin-2-yl]isoxazol-5-yl]-2-fluoro-phenyl]-3,6,6-trimethyl-1-methylimino-1-oxo-2H-1,4-thiazin-5-amine trifluoroacetate, (1R,3R)-3-[5-[3-(5-chloropyrimidin-2-yl)isoxazol-5-yl]-2-fluoro-phenyl]-3,6,6-trimethyl-1-methylimino-1-oxo-2H-1,4-thiazin-5-amine trifluoroacetate, and (1R,3R)-3-[2-fluoro-5-[3-(5-methoxypyrazin-2-yl)isoxazol-5-yl]phenyl]-3,6,6-trimethyl-1-methylimino-1-oxo-2H-1,4-thiazin-5-amine trifluoroacetate.

A certain embodiment of the invention provides a compound of formula I as described herein that is (1R,3R)-3-

[2-fluoro-5-[3-(5-methoxypyrazin-2-yl)isoxazol-5-yl]phenyl]-3,6,6-trimethyl-1-methylimino-1-oxo-2H-1,4-thiazin-5-amine trifluoroacetate.

A certain embodiment of the invention provides a compound of formula I as described herein whenever prepared by a process as described herein.

A certain embodiment of the invention provides a compound of formula I as described herein for use as therapeutically active substance.

A certain embodiment of the invention provides a compound of formula I as described herein for the use as inhibitor of BACE1 activity.

A certain embodiment of the invention provides a compound of formula I as described herein for the use as therapeutically active substance for the therapeutic and/or prophylactic treatment of diseases and disorders characterized by elevated β-amyloid levels and/or β-amyloid oligomers and/or β-amyloid plaques and further deposits or Alzheimer's disease.

A certain embodiment of the invention provides a compound of formula I as described herein for the use as therapeutically active substance for the therapeutic and/or prophylactic treatment of Alzheimer's disease.

A certain embodiment of the invention provides a pharmaceutical composition comprising a compound of formula I as described herein and a pharmaceutically acceptable carrier and/or a pharmaceutically acceptable auxiliary substance.

A certain embodiment of the invention provides the use of a compound of formula I as described herein for the manufacture of a medicament for the use in inhibition of BACE1 activity.

A certain embodiment of the invention provides the use of a compound of formula I as described herein for the manufacture of a medicament for the therapeutic and/or prophylactic treatment of diseases and disorders characterized by elevated β-amyloid levels and/or β-amyloid oligomers and/or β-amyloid plaques and further deposits or Alzheimer's disease.

A certain embodiment of the invention provides the use of a compound of formula I as described herein for the manufacture of a medicament for the therapeutic and/or prophylactic treatment of Alzheimer's disease.

A certain embodiment of the invention provides the use of a compound of formula I as described herein for the manufacture of a medicament for the therapeutic and/or prophylactic treatment of Alzheimer's disease.

A certain embodiment of the invention provides a compound of formula I as described herein for the use in inhibition of BACE1 activity.

A certain embodiment of the invention provides a compound of formula T as described herein for the use in the therapeutic and/or prophylactic treatment of diseases and disorders characterized by elevated β-amyloid levels and/or β-amyloid oligomers and/or β-amyloid plaques and further deposits or Alzheimer's disease.

A certain embodiment of the invention provides a compound of formula I as described herein for the use in the therapeutic and/or prophylactic treatment of Alzheimer's disease.

A certain embodiment of the invention provides a method for the use in inhibition of BACE1 activity, particularly for the therapeutic and/or prophylactic treatment of diseases and disorders characterized by elevated β-amyloid levels and/or β-amyloid oligomers and/or β-amyloid plaques and further deposits or Alzheimer's disease, which method comprises administering compound of formula I as described herein to a human being or animal.

A certain embodiment of the invention provides a method for the use in the therapeutic and/or prophylactic treatment of Alzheimer's disease, which method comprises administering a compound of formula I as described herein to a human being or animal.

Furthermore, the invention includes all optical isomers, i.e. diastereoisomers, diastereomeric mixtures, racemic mixtures, all their corresponding enantiomers and/or tautomers as well as their solvates of the compounds of formula I.

The invention also includes various deuterated forms of compounds of formula I or pharmaceutically acceptable salts thereof. Each available hydrogen atom attached to a carbon atom may be independently replaced with a deuterium atom, in particular a $CH_3$ group may be replaced by a $CD_3$ group. A skilled person will know how to synthesize deuterated forms of compounds of formula I or pharmaceutically acceptable salts thereof.

The skilled person in the art will recognize that the compounds of formula I can exist in tautomeric form

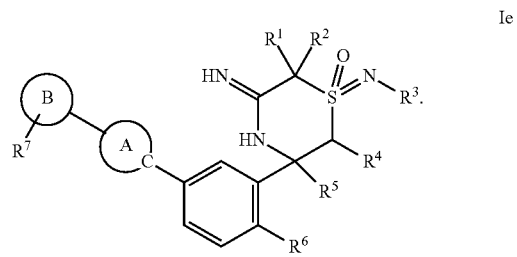

Ie

All tautomeric forms are encompassed in the present invention.

The compounds of formula I may contain one or more asymmetric centers and can therefore occur as racemates, racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within this invention. The present invention is meant to encompass all such isomeric forms of these compounds. The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration. If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography.

Certain embodiments are the following specific forms:

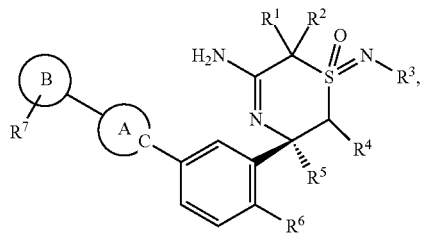

Ia

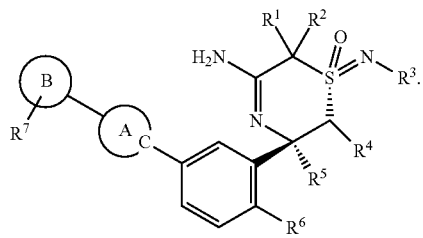

Ic

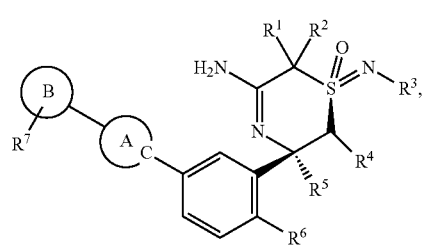

Ib

In the embodiments, where optically pure enantiomers are provided, optically pure enantiomer means that the compound contains >90% of the desired isomer by weight, particularly >95% of the desired isomer by weight, or more particularly >99% of the desired isomer by weight, said weight percent based upon the total weight of the isomer(s) of the compound. Chirally pure or chirally enriched compounds may be prepared by chirally selective synthesis or by separation of enantiomers. The separation of enantiomers may be carried out on the final product or alternatively on a suitable intermediate.

The synthesis of compounds of formula (I) is illustrated in Scheme 1.

Scheme 1

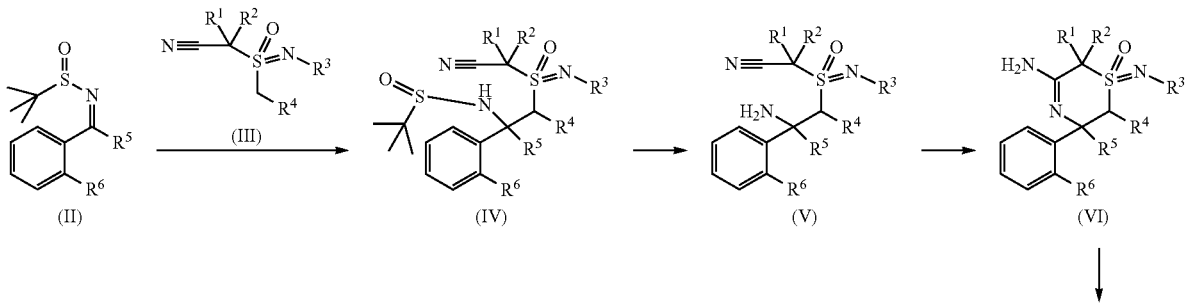

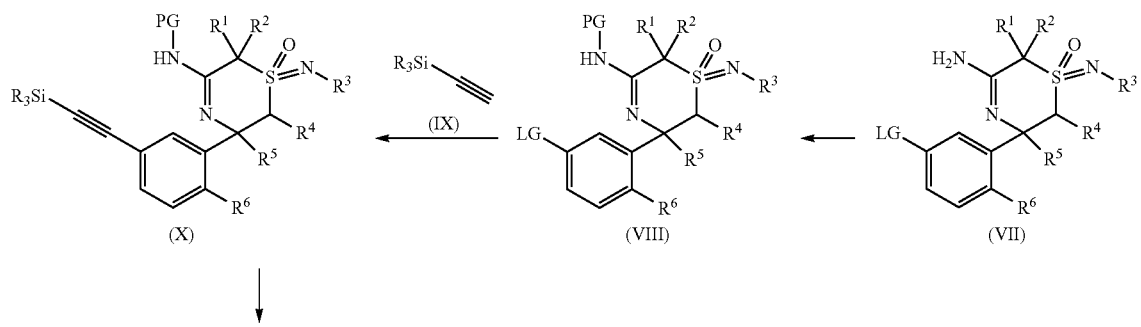

-continued

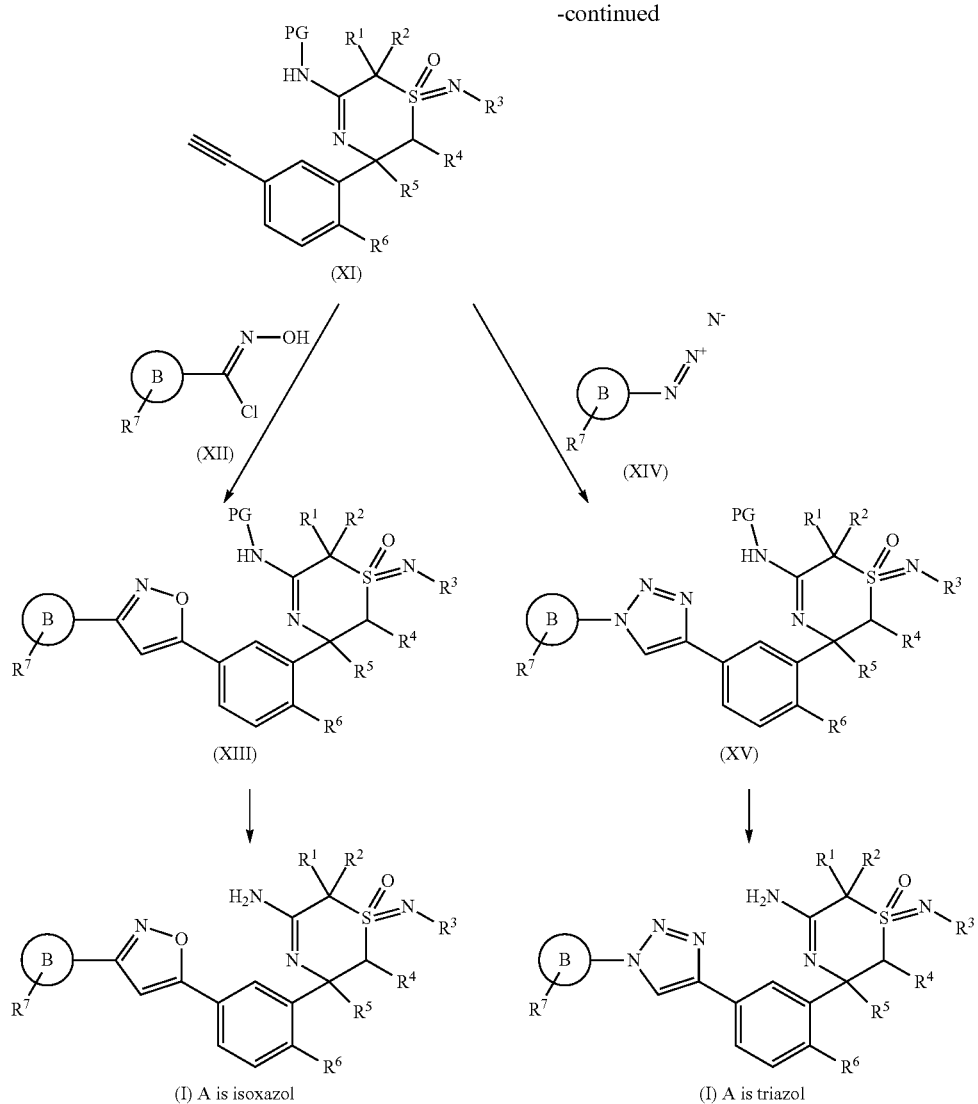

(I) A is isoxazol (I) A is triazol

LG: leaving group, e.g. I, Br
PG: protecting group, e.g. BOC, DMTr
R: alkyl, e.g. Me Starting materials (II) are known or can be prepared in analogy to known methods (e.g. described in Bioorg. Med. Chem. Lett. 2013, 23, 4239-4243). Starting materials (III) are known or can be prepared in analogy to known methods (e.g. described in WO2014/150331). Starting material (II) can be reacted with sulfoximine (III) in the presence of a strong base, e.g. alkali hexamethyldisilazide, such as lithium hexamethyldisilazide, alkali diisopropylamide, such as lithium diisopropylamide, or alkyl lithium, such as n-butyl lithium, under anhydrous conditions in a suitable aprotic solvent, e.g. tetrahydrofuran or dichloromethane, to form (IV) as a mixture of stereoisomers. The single stereoisomers can be separated at this or at a later stage by chromatography and the route depicted in Scheme 1 can be followed analogously employing the separated single isomers.

The sulfinamide moiety of (IV) can be cleaved with a mineral acid, e.g. sulfuric acid or particularly hydrochloric acid, in a solvent such as an ether, e.g. diethyl ether, tetrahydrofuran or more particularly 1,4-dioxane to give the corresponding amine (V). Subsequently, (V) can be cyclised to amidines (VI) using methods known in the art, e.g. using stoichiometric amounts of copper(I) salts, e.g. copper(I) chloride or copper(I) bromide, in suitable solvents, e.g. alcohols, such as ethanol, at elevated temperatures, such as 20° C. to 130° C., preferably at 70° C. to 90° C. Alternatively, the transformation can be achieved using stoichiometric amounts of a Lewis acid, like trimethyl aluminium, in a suitable aprotic solvent, such as toluene.

Compounds (VI) can be converted into compounds (VII) containing a leaving group such as iodide or bromide by e.g. iodination using an iodinating agent such as N-iodosuccinimide in the presence of an acid such as trifluoromethanesulfonic acid or tetrafluoroboric acid in a solvent such as dichloromethane at a temperature between 0° C. and reflux temperature of the solvent or by bromination using a brominating agent such as N-bromosuccinimide in the presence of an acid or acid mixtures such as trifluoroacetic acid and sulfuric acid. Protection of the amino group in compounds of formula (VII) to produce compounds of formula (VIII) can be performed by methods known in the art, e.g. as described in T. W. Greene and P. G. M. Wuts, "Protective Groups in Organic Synthesis", 2nd ed., John Wiley & Sons, Inc., New York, N.Y., 1991. In case PG is tert-butoxycarbonyl (BOC), the transformation can be achieved by treatment with di-tert-butyl dicarbonate in a solvent such as dichloromethane at temperatures between 0° C. and reflux temperature of the solvent. In case PG is a triarylmethyl, the transformation can be achieved by treatment with triarylmethyl chlorides, such as triphenylmethyl chloride (Tr-Cl), di(p-methoxyphenyl)phenylmethyl chloride (DMTr-Cl) under basic conditions, e.g. in the presence of an amine, such as triethylamine or diisopropylethylamine, in a chlorinated solvent, such as dichloromethane or chloroform, at temperatures between 0° C. and ambient temperature.

Sonogashira coupling of terminal alkynes (IX) with compounds of formula (VIII) in which LG is preferably iodide to yield compounds of formula (X) can be achieved with a palladium catalyst, e.g. bis(triphenyphosphine)palladium(II) chloride, a copper(I) co-catalyst, e.g. copper(I) iodide, and an amine base, e.g. triethylamine under conditions known to those skilled in the art.

Removal of the $R_3Si$ group of compounds (X) to give terminal acetylenes (XI) can be achieved by methods well known in the art, e.g. by treatment with fluoride containing reagents such as tetrabutylammonium fluoride in a solvent such as dichloromethane or THF at a temperature between 0° C. and ambient temperature or by treatment with potassium carbonate in a solvent such as ethanol or methanol at ambient temperature.

Conversion of acetylenes (XI) into isoxazoles (XIII) can be achieved by a 1,3-dipolar cycloaddition with a reagent system consisting of a heteroaryl-carboximidoyl chloride (XII) and a base such as sodium bicarbonate or triethylamine in a solvent such as THF or isopropanol at temperatures between 0° C. and reflux temperature of the solvent.

Conversion of acetylenes (XI) into triazoles (XV) can be achieved by a copper(I)-catalyzed cycloaddition with heteroaryl azides (XIV) using either a copper(I) reagent such as CuI or copper(I) trifluoromethanesulfonate benzene complex or a copper(II) reagent such as CuSO4 in the presence of a reducing agent such as sodium ascorbate and a base such as NaHCO3 in a solvent or solvent mixtures such as toluene, THF or DMF at a temperature from ambient temperature to reflux of the solvent.

Removal of the amine-protecting group PG in compounds (XIII) and compounds (XV) to give compounds of formula (I) can be achieved by methods well known in the art, e.g. by treatment with strong carbonic acids, e.g. trifluoroacetic acid, in a solvent, e.g. dichloromethane, at temperatures between 0° C. and 23° C. The product of formula (I) can either be isolated as a salt, e.g. as a trifluoroacetic acid salt or as a free base. The free base of compounds of formula (I) can be obtained from the corresponding salts by treatment with a base and, if desired can be converted into a salt with another acid by treatment with the corresponding acid.

Scheme 2

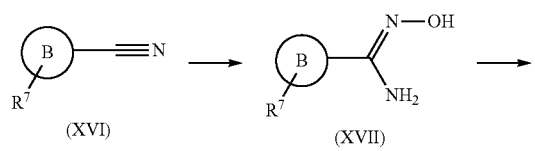

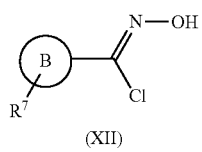

Heteroaryl-carboximidoyl chlorides (XII) are known or can be prepared in analogy to methods known in the art or using methods illustrated in Scheme 2. Heteroaryl nitriles (XVI) can be converted into heteroaryl amidoximes (XVII) by treatment with hydroxylamine or a hydroxylamine salt such as hydroxylamine hydrochloride in the presence of a base such as sodium hydroxide or triethylamine in a solvent or solvent mixtures such as water and ethanol at temperatures between 0° C. and reflux temperature of the solvent. Conversion of compounds (XVII) into heteroaryl-carboximidoyl chlorides (XII) can be performed by a Sandmeyer-type reaction by treatment with a nitrite such as sodium nitrite in the presence of aqueous hydrochloric acid preferably at a temperature <10° C.

Scheme 3

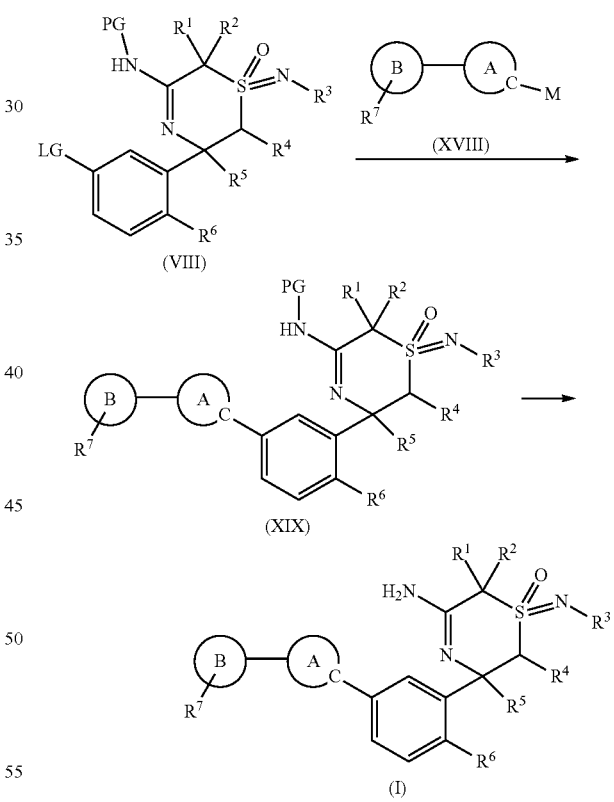

LG: leaving group, e.g. I, Br
PG: protecting group, e.g. BOC, DMTr
M: Metal derivative, e.g. B(OH)$_2$, B(pin), B(MIDA)

An alternative synthesis of compounds of formula (I) is depicted in Scheme 3: compounds (VIII) containing a leaving group such as I or Br can be coupled with metal derivatives such as boronic acids or boronic acid esters (XVIII) using well-known cross-coupling reaction conditions. In particular, the coupling of compounds (VIII) with a boronic acid or a boronic ester (XVIII) to the compound of formula (XIX) can be effected with a ferrocen derived catalyst, in particular 1,1'-bis(diphenylphosphino)-ferrocene-palladium(II)dichloride complex with dichloromethane and a metal carbonate, in particular cesium carbonate in a solvent mixture of an ether and water, in particular THF and water at elevated temperature, in particular between 80-90° C.

Removal of the amine-protecting group PG to give compounds of formula (I) can be achieved by methods well known in the art, e.g. by treatment with strong carbonic acids, e.g. trifluoroacetic acid, in a solvent, e.g. dichloromethane, at temperatures between 0° C. and 23° C. The product of formula (I) can either be isolated as a salt, e.g. as a trifluoroacetic acid salt or as a free base. The free base of compounds of formula (I) can be obtained from the corresponding salts by treatment with a base and, if desired can be converted into a salt with another acid by treatment with the corresponding acid.

The corresponding pharmaceutically acceptable salts with acids can be obtained by standard methods known to the person skilled in the art, e.g. by dissolving the compound of formula I in a suitable solvent such as e.g. dioxane or tetrahydrofuran and adding an appropriate amount of the corresponding acid. The products can usually be isolated by filtration or by chromatography. The conversion of a compound of formula I into a pharmaceutically acceptable salt with a base can be carried out by treatment of such a compound with such a base. One possible method to form such a salt is e.g. by addition of 1/n equivalents of a basic salt such as e.g. $M(OH)_n$, wherein M=metal or ammonium cation and n=number of hydroxide anions, to a solution of the compound in a suitable solvent (e.g. ethanol, ethanol-water mixture, tetrahydrofuran-water mixture) and to remove the solvent by evaporation or lyophilisation. Particular salts are hydrochloride, formate and trifluoroacetate. Specific is trifluoroacetate.

Insofar as their preparation is not described in the examples, the compounds of formula I as well as all intermediate products can be prepared according to analogous methods or according to the methods set forth herein. Starting materials are commercially available, known in the art or can be prepared by methods known in the art or in analogy thereto.

It will be appreciated that the compounds of general formula I in this invention may be derivatised at functional groups to provide derivatives which are capable of conversion back to the parent compound in vivo.

Pharmacological Tests

The compounds of formula I and their pharmaceutically acceptable salts possess valuable pharmacological properties. It has been found that the compounds of the present invention are associated with inhibition of BACE1 activity. The compounds were investigated in accordance with the test given hereinafter.

Cellular Aβ-Lowering Assay:

The Abeta 40 AlphaLISA Assay can be used. The HEK293 APP cells were seeded in 96 well Microtiter plates in cell culture medium (Tscove's, plus 10% (v/v) fetal bovine serum, penicillin/streptomycin) to about 80% confluency and the compounds were added at a 3× concentration in 1/3 volume of culture medium (final DMSO concentration was kept at 1% v/v). After 18-20 hrs incubation at 37° C. and 5% $CO_2$ in a humidified incubator, the culture supernatants were harvested for the determination of Aβ 40 concentrations using Perkin-Elmer Human Amyloid beta 1-40 (high specificity) Kit (Cat # AL275C).

In a Perkin-Elmer White Optiplate-384 (Cat #6007290), 2 ul culture supernatants were combined with 2 μl of a 10× AlphaLISA Anti-hAβAcceptor beads+Biotinylated Antibody Anti-APβ 1-40 Mix (50 μg/mL/5 nM). After 1 hour room temperature incubation, 16 μl of a 1.25× preparation of Streptavidin (SA) Donor beads (25 μg/mL) were added and incubated for 30 minutes in the Dark. Light Emission at 615 nm was then recorded using EnVision-Alpha Reader. Levels of Aβ 40 in the culture supernatants were calculated as percentage of maximum signal (cells treated with 1% DMSO without inhibitor). The $IC_{50}$ values were calculated using the Excel XLfit software.

Lowering of A0340 in Brain of Wild-Type Mice:

Animals and Housing Conditions.

Animals were maintained in a 12/12 h light/dark cycle, with lights starting at 6 a.m., and experiments were conducted during the light phase. Animal housing and experimental procedures were in line with ethical and legal guidelines and were authorized by local veterinary authorities.

Experiment.

Female C57Bl/6J mice were treated with a dose of 30 mg/kg of the compounds, 3-4 animals per treatment group. The test compound was dissolved in 5% EtOH, 10% Solutol, and was applied per os at 10 mL/kg. After 4 h, the animals were sacrificed and brain and plasma were collected. The brain was cut into halves and immediately frozen on dry ice. Brain was used for measurement of Aβ40 and plasma was used for determination of compound exposure. The method for Aβ40 determination in brain lysates followed the known procedure (Lanz, T. A.; Schachter, J. B. Demonstration of a common artifact in immunosorbent assays of brain extracts: development of a solidphase extraction protocol to enable measurement of amyloid-β from wild-type rodent brain. J. Neurosci. Methods 2006, 157, 71-81). Brain tissue was homogenized in 2% DEA buffer in a Roche MagnaLyser (20", 4000 rpm) and subsequently centrifuged for 1 h at 100000 g. DEA was reduced to 0.2% in 50 mM NaCl and one-half of the DEA lysate was passed over an Oasis Solid phase extraction plate (Waters; cat. no. 186000679), which had been activated with MeOH and equilibrated in dH2O (1 mL each). After washes in 10% and 30% MeOH (1 mL each), the Aβ-peptides were eluted in 0.8 mL of 2% NH4OH in 90% MeOH. The eluate was dried over a N2 flow, and the dried sample was reconstituted in 30 μL of AlphaLISA assay buffer. Aβ40 was determined by an AlphaLISA assay (Perkin-Elmer). In a white 96-well, half area microplate (Perkin-Elmer cat. no. 6005561), 20 μL of the reconstituted sample were mixed with 5 μL of biotinylated BAP-24 (specific for C-terminus of Aβ40) (Brockhaus, M.; Grunberg, J.; Rohrig, S.; Loetscher, H.; Wittenburg, N.; Baumeister, R.; Jacobsen, H.; Haass, C. Caspasemediated cleavage is not required for the activity of presenilins in amyloidogenesis and NOTCH signaling. NeuroReport 1998, 9, 1481-1486) stock=4.4 mg/mL, f.c.5.5 μg/mL), and 5 μL 252Q6 acceptor beads (252Q6 antibody, Invitrogen AMB0062) had been previously conjugated with AlphaLISA Acceptor beads (Perkin-Elmer cat. no. 6772002); final dilution 1:500). The mix was incubated for 1 h at RT in the dark. Then 20 μL of Streptavin-coated Donor Beads (Perkin-Elmer cat. no. 6760002, final dilution 1:125) were added and this final mix was incubated in the dark for another 30 min at RT before RFU was measured in an AlphaScreen Reader (Perkin-Elmer Envision 2104). The value obtained for Aβ40 in the treated animals was related to the value in the vehicle group and is given in %. Alternatively a commercial ELISA was used for Aβ40 determination (Wako ELISA: ("Human/Rat β Amyloid (40) ELISA kit Wako II"; cat nr. 294-64701) following the manufacture's instruction. Also here the Aβ-lowering efficacy was calculated as percentage of the vehicle group.

TABLE 1
IC50 values of selected examples
| Example | Structure | BACE1 cell act. Aβ40 IC$_{50}$ [nM] |
|---|---|---|
| 1 | 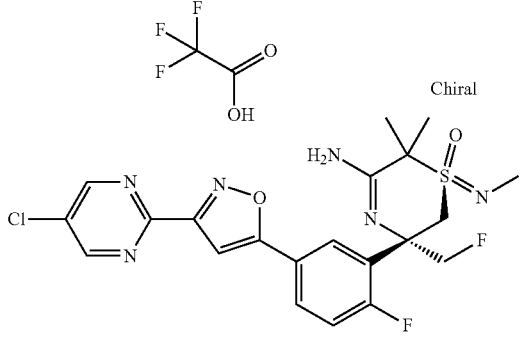 [SMILES: O=C(O)C(F)(F)F ; CN=[S@]1(=O)C[C@@](CF)(c2cc(-c3cc(-c4ncc(Cl)cn4)no3)ccc2F)N=C(N)C1(C)C] | 95 |
| 2 | 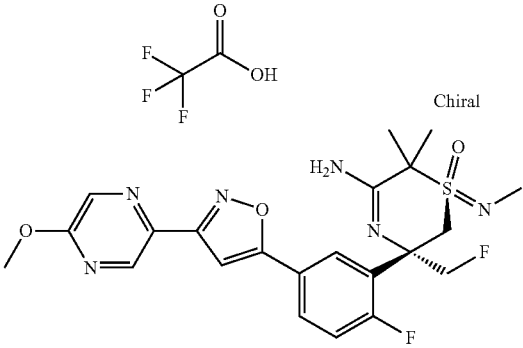 | 141 |
| 3 | 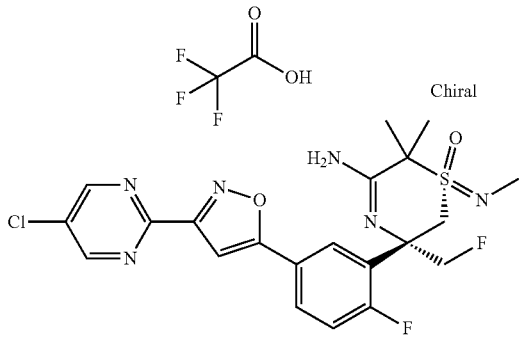 [SMILES: O=C(O)C(F)(F)F ; CN=[S@@]1(=O)C[C@@](CF)(c2cc(-c3cc(-c4ncc(Cl)cn4)no3)ccc2F)N=C(N)C1(C)C] | 89 |
| 4 | 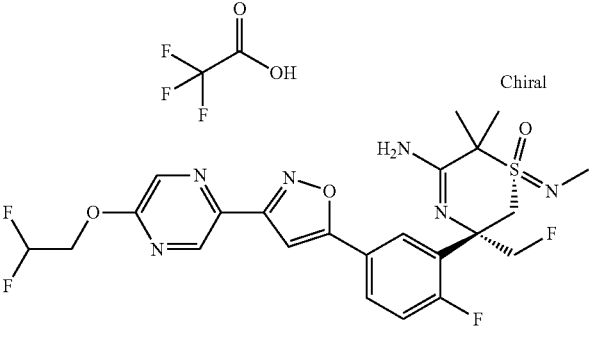 [SMILES: CN=[S@@]1(=O)C[C@@](CF)(c2cc(-c3cc(-c4cnc(OCC(F)F)cn4)no3)ccc2F)N=C(N)C1(C)C ; O=C(O)C(F)(F)F] | 111 |

TABLE 1-continued
IC50 values of selected examples
| Example | Structure | BACE1 cell act. Aβ40 IC$_{50}$ [nM] |
|---|---|---|
| 5 | 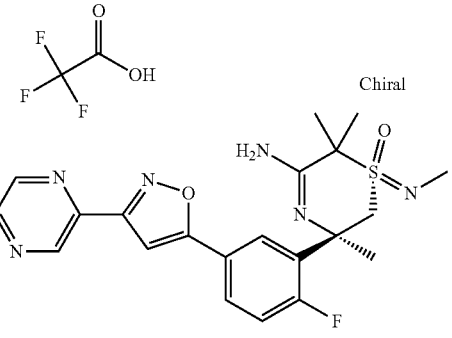 | 13 |
| 6 | 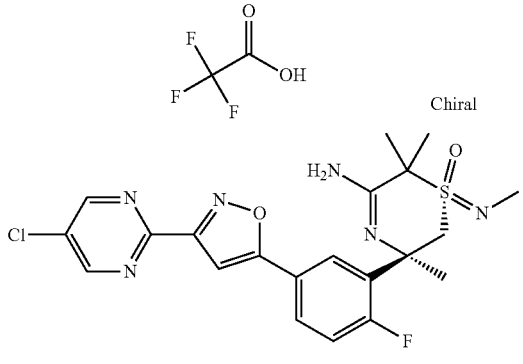 [SMILES: O=C(O)C(F)(F)F ; CN=[S@@]1(=O)C[C@@](C)(c2cc(-c3cc(-c4ncc(Cl)cn4)no3)ccc2F)N=C(N)C1(C)C] | 6 |
| 7 | 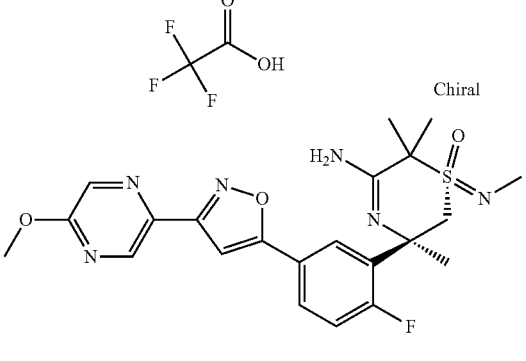 | 56 |
| 8 | 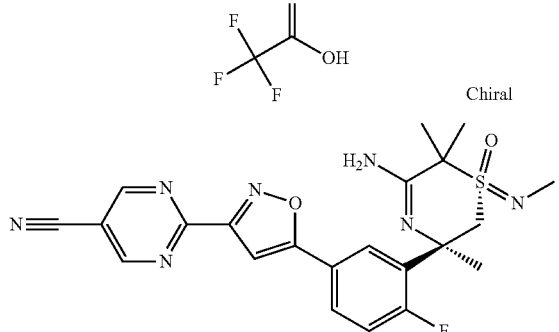 | 22 |

TABLE 1-continued
IC50 values of selected examples
| Example | Structure | BACE1 cell act. Aβ40 IC$_{50}$ [nM] |
|---|---|---|
| 9 | 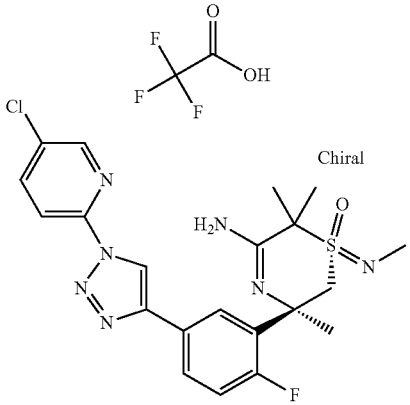 [SMILES: CN=[S@@]1(=O)C[C@@](C)(c2cc(-c3cn(-c4ccc(Cl)cn4)nn3)ccc2F)N=C(N)C1(C)C ; O=C(O)C(F)(F)F] | 17 |
| 10 | 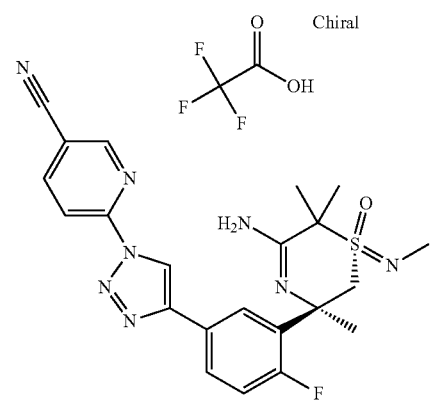 [SMILES: CN=[S@@]1(=O)C[C@@](C)(c2cc(-c3cn(-c4ccc(C#N)cn4)nn3)ccc2F)N=C(N)C1(C)C ; O=C(O)C(F)(F)F] | 20 |
| 11 | 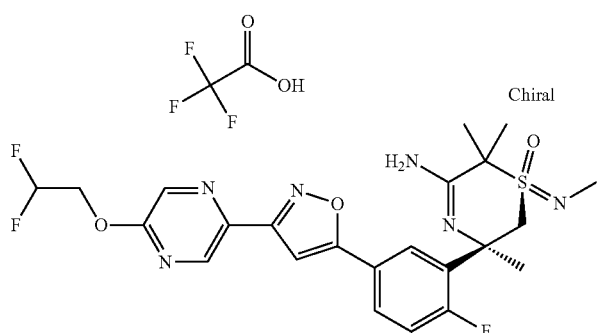 | 51 |
| 12 | 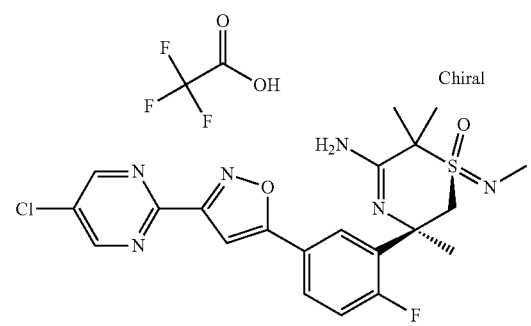 | 19 |

TABLE 1-continued

IC50 values of selected examples

| Example | Structure | BACE1 cell act. Aβ40 IC$_{50}$ [nM] |
|---|---|---|
| 13 | 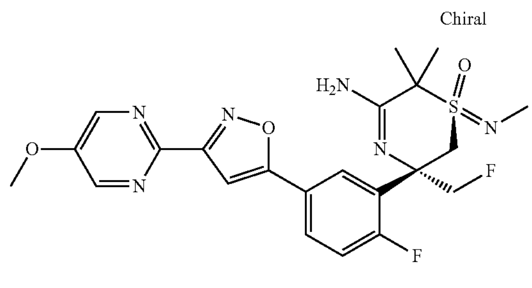 | 106 |
| 14 | 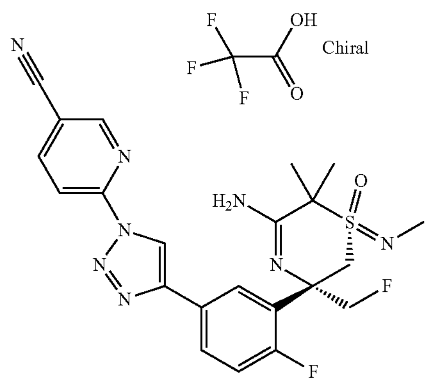 [SMILES: CN=[S@@]1(=O)C[C@@](CF)(c2cc(-c3cn(-c4ccc(C#N)cn4)nn3)ccc2F)N=C(N)C1(C)C ; O=C(O)C(F)(F)F] | 103 |
| 15 | 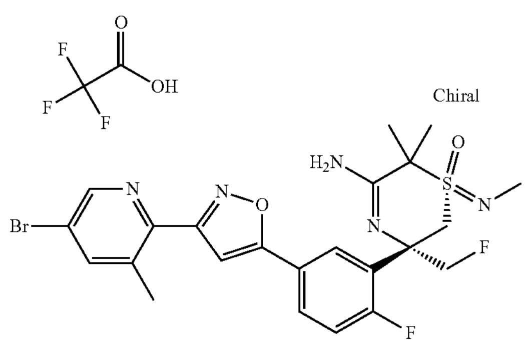 [SMILES: O=C(O)C(F)(F)F ; CN=[S@@]1(=O)C[C@@](CF)(c2cc(-c3cc(-c4ncc(Br)cc4C)no3)ccc2F)N=C(N)C1(C)C] | 344 |
| 16 | 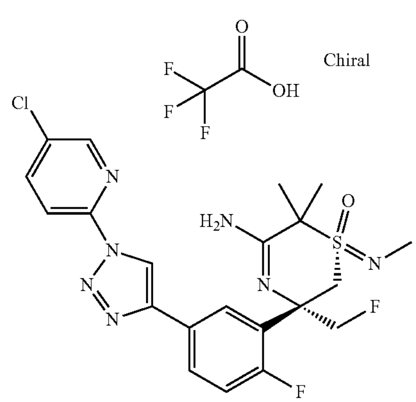 [SMILES: CN=[S@@]1(=O)C[C@@](CF)(c2cc(-c3cn(-c4ccc(Cl)cn4)nn3)ccc2F)N=C(N)C1(C)C ; O=C(O)C(F)(F)F] | 156 |

TABLE 1-continued
IC50 values of selected examples
| Example | Structure | BACE1 cell act. Aβ40 IC$_{50}$ [nM] |
|---|---|---|
| 17 | 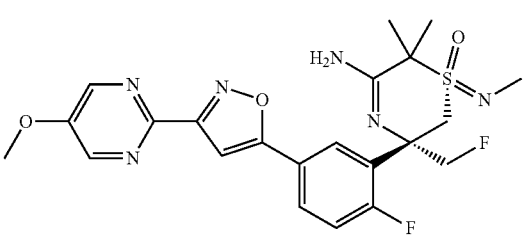 | 119 |
| 18 | 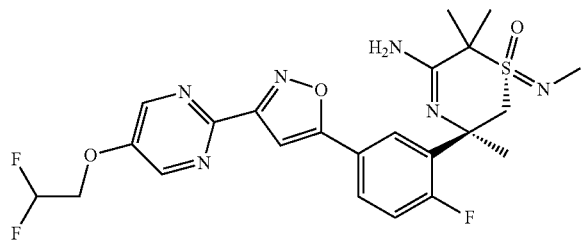 | 13 |
| 19 | 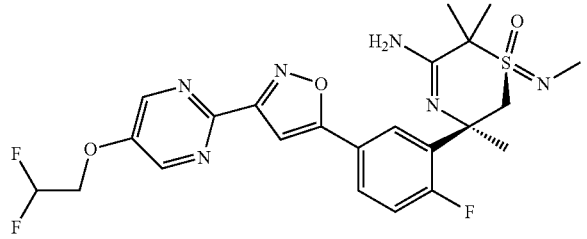 | 27 |
| 20 | 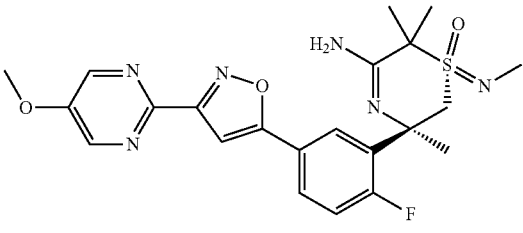 | 3 |
| 21 | 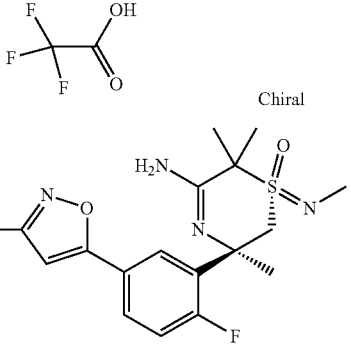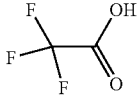 | 9 |

TABLE 1-continued

IC50 values of selected examples

| Example | Structure | BACE1 cell act. Aβ40 IC$_{50}$ [nM] |
|---|---|---|
| 22 | 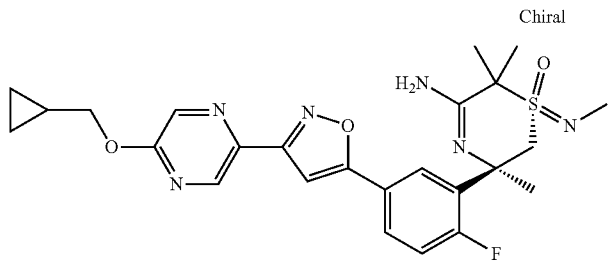 [SMILES: CN=[S@@]1(=O)C[C@@](C)(c2cc(-c3cc(-c4cnc(OCC5CC5)cn4)no3)ccc2F)N=C(N)C1(C)C] | 61 |
| 23 | 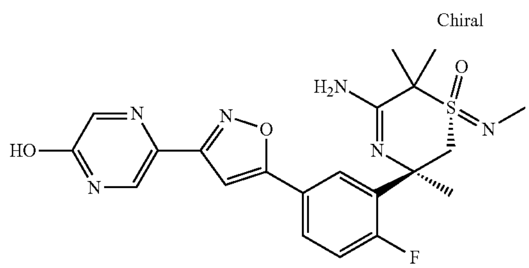 [SMILES: CN=[S@@]1(=O)C[C@@](C)(c2cc(-c3cc(-c4cnc(O)cn4)no3)ccc2F)N=C(N)C1(C)C] | >1000 |
| 24 | 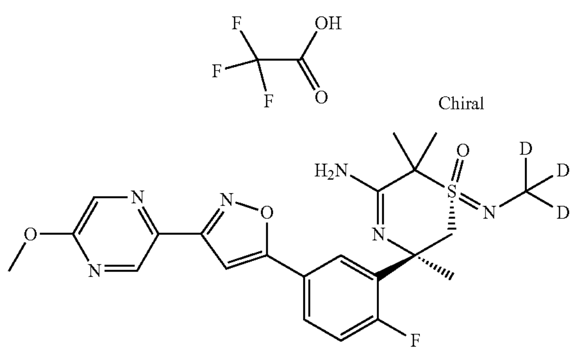 [SMILES: O=C(O)C(F)(F)F ; [2H]C([2H])([2H])N=[S@@]1(=O)C[C@@](C)(c2cc(-c3cc(-c4cnc(OC)cn4)no3)ccc2F)N=C(N)C1(C)C] | 50 |
| 25 | 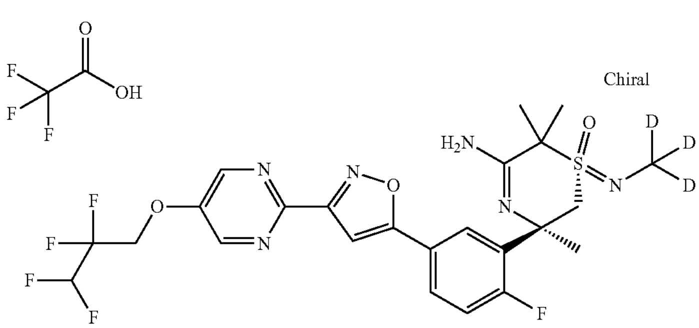 [SMILES: O=C(O)C(F)(F)F ; [2H]C([2H])([2H])N=[S@@]1(=O)C[C@@](C)(c2cc(-c3cc(-c4ncc(OCC(F)(F)C(F)F)cn4)no3)ccc2F)N=C(N)C1(C)C] | 13 |

TABLE 1-continued
IC50 values of selected examples
| Example | Structure | BACE1 cell act. Aβ40 IC$_{50}$ [nM] |
|---|---|---|
| 26 | 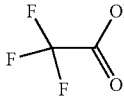 | 37 |
| 27 | 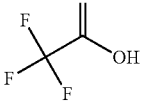 | 139 |
| 28 | 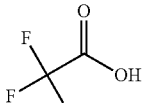 | 7 |
| 29 | 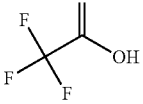 | 20 |

TABLE 1-continued

IC50 values of selected examples

| Example | Structure | BACE1 cell act. Aβ40 IC$_{50}$ [nM] |
|---|---|---|
| 30 | Chiral | 104 |
| 31 | Chiral | — |
| 32 | Chiral | — |
| 33 | Chiral | 92 |

TABLE 1-continued
IC50 values of selected examples
| Example | Structure | BACE1 cell act. Aβ40 IC$_{50}$ [nM] |
|---|---|---|
| 34 | 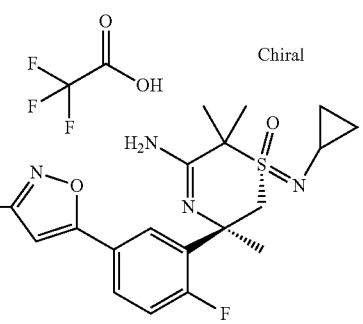 | 13 |
| 35 | 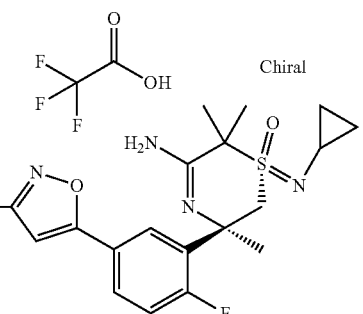 | 13 |
| 36 | 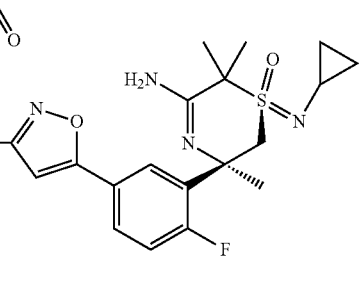 | 7 |
| 37 | 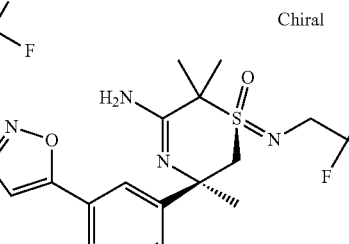 | 6 |

TABLE 1-continued
IC50 values of selected examples
| Example | Structure | BACE1 cell act. Aβ40 IC$_{50}$ [nM] |
|---|---|---|
| 38 | 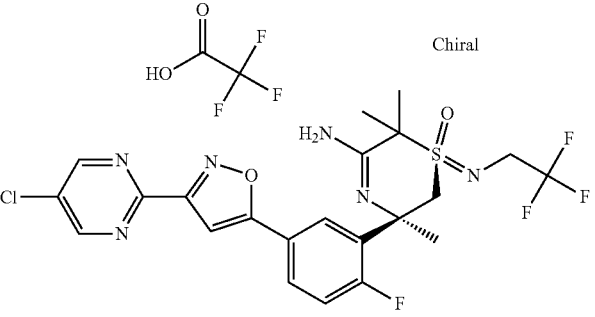 | 13 |
| 39 | 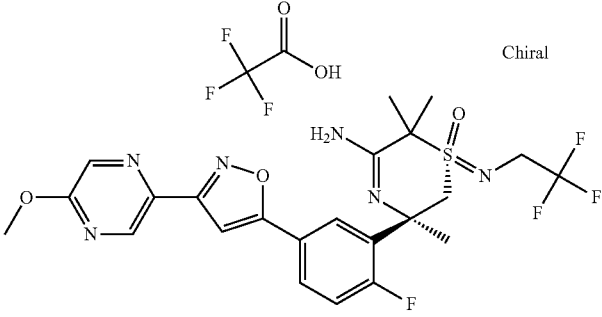 [SMILES: COc1cnc(-c2cc(-c3ccc(F)c([C@]4(C)C[S@](=O)(=NCC(F)(F)F)C(C)(C)C(N)=N4)c3)on2)cn1 ; O=C(O)C(F)(F)F] | 232 |
| 40 | 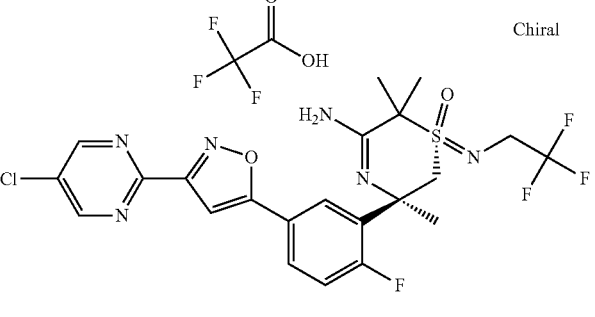 | 37 |
| 41 | 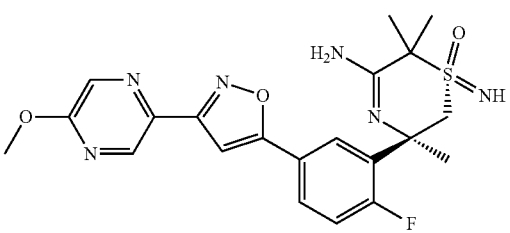 | 8 |

TABLE 1-continued

IC50 values of selected examples

| Example | Structure | BACE1 cell act. Aβ40 IC$_{50}$ [nM] |
|---|---|---|
| 42 | (Chiral structure) | — |
| 43 | (Chiral structure) | — |
| 44 | (Chiral structure) | — |

CYP Inhibition Assay

Inhibition of cytochromes P450 (CYPs) 2C9, 2D6 and 3A4 was assessed using human liver microsomes and CYP-selective substrate metabolism reactions. 50 µl incubations were made up containing (finally) 0.2 mg/ml pooled human liver microsomes, 5 µM substrate (diclofenac for CYP2C9 [4'hydroxylase], dextromethorphan for CYP2D6 [O-demethylase] or midazolam for CYP3A4 [1'hydroxylase]), 0.25 µL DMSO containing test inhibitor and NADPH regenerating system. Test inhibitor concentrations of 50, 16.7, 5.6, 1.9, 0.6 and 0.2 µM were assessed in singlicate. Incubations were prewarmed to 37° C. for 10 minutes before initiation by addition of NADPH regenerating system. Incubations were quenched after 5 minutes (20 minutes for dextromethorphan) by addition of 50 µl cold acetonitrile containing 20 ng/ml 4-OH-diclofenac-13C6, 20 ng/mL dextrorphan-D3 and 20 ng/mL 1-OH-midazolam-D4. Quenched incubates were stored at −20° C. for at least 1 hour before centrifugation (20,000×g, 20 minutes). Supernatants were removed and diluted 1:1 with water prior to analysis using a Rapid-Fire sample injector system and API4000 mass spectrometer. Peak areas for substrate, metabolite and stable-labelled metabolite standard were determined using MS/MS. The peak area ratios between the metabolite generated by the enzymatic reaction and the internal standard were used in subsequent calculations. The percentage of (DMSO) control activity was calculated for each incubate and IC$_{50}$ values estimated by non-linear regression. Sulfaphenazole, quinidine or ketoconazole were tested in each CYP2C9, CYP2D6 or CYP3A4 inhibition experiment, respectively, to ensure assay sensitivity and reproducibility. (Validated assays for human cytochrome P450 activities, R. L. Walsky and R. S. Obach, Drug Metabolism and Disposition 32: 647-660, 2004, and S. Fowler and H. Zhang, The AAPS Journal, Vol. 10, No. 2, 410-424, 2008)

Cathepsin D and Cathepsin E Fluorescent Substrate Kinetic Assays

General Assay Principle

The MR121 fluorescence assays described below are based on the fact that MR121 forms a non-fluorescent ground state complex with tryptophan. In solution this formation occurs at millimolar concentrations of tryptophan. The mechanism can be used to design a generic biochemical assay for proteases. A substrate peptide is labeled at the N-terminus with tryptophan and at the C-terminus with the fluorophore MR121 (for cathepsin D the 10 amino acid peptide WTSVLMAAPC-MR121 was used; for cathepsin E, MR121-CKLVFFAEDW was used). In absence of protease activity, the substrates remain intact and the MR121 fluorescence is reduced by the high local Trp-concentration. If the substrates are cleaved by the enzymes the MR121 fluorescence is recovered.

Assay Procedure

The fluorescent substrate cathepsin D and cathepsin E kinetic assays were performed at room temperature in 384-well microtiter plates (black with clear flat bottom, non-binding surface plates from Corning) in a final volume of 51 µl. The test compounds were serially diluted in DMSO (15 concentrations, 1/3 dilution steps) and 1 µl of diluted compounds were mixed for 10 min with 40 µl of cathepsin D (from human liver, Calbiochem) diluted in assay buffer (100 mM sodium acetate, 0.05% BSA, pH 5.5; final concentration: 200 nM) or with 40 µl of recombinant human cathepsin E (R&D Systems) diluted in assay buffer (100 mM sodium acetate, 0.05% BSA, pH 4.5; final concentration: 0.01 nM). After addition of 10 µl of the cathepsin D substrate WTS-VLMAAPC-MR121 diluted in cathepsin D assay buffer (final concentration: 300 nM) or µl of the cathepsin E substrate MR121-CKLVFFAEDW diluted in cathepsin E assay buffer (final concentration: 300 nM), the plates were strongly shaken for 2 minutes. The enzymatic reaction was followed in a plate: vision reader (Perkin Elmer) (excitation wavelength: 630 nm; emission: 695 nm) for at least 30 minutes in a kinetic measurement detecting an increase of MR121 fluorescence during the reaction time. The slope in the linear range of the kinetic was calculated and the $IC_{50}$ of the test compounds were determined using a four parameter equation for curve fitting.

In Vitro Transport Experiments

Bidirectional transcellular transport using LLC-PK1 and L-MDR1 LLC-PK1 cells exogenously expressing the human MDR1)

The method used for transport experiments was reported Schwab D, Schrag P, Portmann R, Rühmann S. Operation procedure: LLC-PK1 cell lines, parental and transfected with human (MDR1) or mouse (mdr1a) Pglycoprotein to study transcellular transport by P-glycoprotein. Report No. 1008708. Jul. 1, 2002. and Schwab D, Schrag P, Portmann R. Validation report on in vitro P-glycoprotein transport of 16 reference compounds in LLC-PK1 cells (parental) and MDR1 or mdr1a (Mouse multidrug resistance protein 1a) transfected LLC-PK1 cells and correlation to in vivo brain penetration in mice). The experiments were performed on a TECAN automated liquid handling system. Briefly, medium was removed from all compartments and the medium of receiver side was replaced with culture medium. The transcellular transport measurements were initiated by adding the substrate together with extracellular marker lucifer yellow to the donor side. Inhibitors were added to both sides (1 µM elacridar). Transport experiments were performed both in the basolateral-to-apical and apical-to-basolateral directions with 3 wells each. The plates were incubated at 37° C. and 5% $CO_2$ in a Liconic incubator. Samples were taken from the donor and the opposite (acceptor) side after 2 hours incubation. Concentrations of substrate in both compartments were determined by scintillation counting (digoxin) or by LC-MS/MS. The extracellular marker (lucifer yellow) was quantified using a spectrafluor plus reader at 430/535 nm (Ex/Em). In each experiment 3 different inserts were used for each condition and a mean was calculated.

Data Analysis

Bidirectional transcellular transport using LLC-PK1 and L-MDR1 cells

For the transcellular transport, the following equation was used for data evaluation:

$$P_{app} = \frac{1}{A * C_0} * \frac{dQ}{dt}$$

Where $P_{app}$, A, $C_0$, and dQ/dt represent the apparent permeability, the filter surface area, the initial concentration, and the amount transported per time period, respectively. $P_{app}$ values were calculated on the basis of a single time point (2 h).

Transport efflux ratios (ER) were calculated as follows:

$$ER = \frac{P_{app}BA}{P_{app}AB}$$

Where $P_{app}BA$ is the permeability value in the basolateral-to-apical direction, and $P_{app}AB$ the permeability value in the apical-to-basolateral direction. $P_{app}$ were not corrected for flux of the extracellular marker lucifer yellow, which was used to assess the quality of the cell monolayers.

Results

TABLE 2

Pharmacological data, NF = in vitro no significant adduct formation relative to control, A = less than 60% of control @ 30 mg/kg mouse, B = less than 90% of control @ 30 mg/kg mouse, C = $IC_{50}$ > 10 µM

| Ex. | GSH human | in vivo effect | Cathepsin E $IC_{50}$ [µM] | Cathepsin D $IC_{50}$ [µM] | CYP $IC_{50}$ [µM] 3A4 | 2D6 | 2C9 |
|---|---|---|---|---|---|---|---|
| 1 | NF | — | 139 | 75 | — | C | C |
| 5 | NF | A | 78 | 29 | C | — | C |
| 6 | NF | A | 79 | 38 | C | C | C |
| 7 | NF | B | 182 | 37 | C | C | C |
| 24 | — | A | 167 | 39 | C | C | C |
| 28 | — | — | 7 | 16 | C | C | C |
| 41 | — | — | 56 | 45 | C | C | C |

Pharmaceutical Compositions

The compounds of formula I and the pharmaceutically acceptable salts can be used as therapeutically active substances, e.g. in the form of pharmaceutical preparations. The pharmaceutical preparations can be administered orally, e.g. in the form of tablets, coated tablets, dragées, hard and soft gelatin capsules, solutions, emulsions or suspensions. The administration can, however, also be effected rectally, e.g. in the form of suppositories, or parenterally, e.g. in the form of injection solutions.

The compounds of formula I and the pharmaceutically acceptable salts thereof can be processed with pharmaceutically inert, inorganic or organic carriers for the production of pharmaceutical preparations. Lactose, corn starch or derivatives thereof, talc, stearic acids or its salts and the like can be used, for example, as such carriers for tablets, coated tablets, dragées and hard gelatin capsules. Suitable carriers for soft gelatin capsules are, for example, vegetable oils, waxes, fats, semi-solid and liquid polyols and the like. Depending on the nature of the active substance no carriers are however usually required in the case of soft gelatin capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical preparations can, moreover, contain pharmaceutically acceptable auxiliary substances such as preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

Medicaments containing a compound of formula I or a pharmaceutically acceptable salt thereof and a therapeutically inert carrier are also provided by the present invention, as is a process for their production, which comprises bringing one or more compounds of formula I and/or pharmaceutically acceptable salts thereof and, if desired, one or more other therapeutically valuable substances into a galenical administration form together with one or more therapeutically inert carriers.

The dosage can vary within wide limits and will, of course, have to be adjusted to the individual requirements in each particular case. In the case of oral administration the dosage for adults can vary from about 0.01 mg to about 1000 mg per day of a compound of general formula I or of the corresponding amount of a pharmaceutically acceptable salt thereof. The daily dosage may be administered as single dose or in divided doses and, in addition, the upper limit can also be exceeded when this is found to be indicated.

The following examples illustrate the present invention without limiting it, but serve merely as representative thereof. The pharmaceutical preparations conveniently contain about 1-500 mg, particularly 1-100 mg, of a compound of formula I. Examples of compositions according to the invention are:

Example A

Tablets of the following composition are manufactured in the usual manner:

TABLE 3 possible tablet composition

| ingredient | mg/tablet | | | |
|---|---|---|---|---|
|  | 5 | 25 | 100 | 500 |
| Compound of formula I | 5 | 25 | 100 | 500 |
| Lactose Anhydrous DTG | 125 | 105 | 30 | 150 |
| Sta-Rx 1500 | 6 | 6 | 6 | 60 |
| Microcrystalline Cellulose | 30 | 30 | 30 | 450 |
| Magnesium Stearate | 1 | 1 | 1 | 1 |
| Total | 167 | 167 | 167 | 831 |

Manufacturing Procedure

1. Mix ingredients 1, 2, 3 and 4 and granulate with purified water.
2. Dry the granules at 50° C.
3. Pass the granules through suitable milling equipment.
4. Add ingredient 5 and mix for three minutes; compress on a suitable press.

Example B-1

Capsules of the following composition are manufactured:

TABLE 4 possible capsule ingredient composition

| ingredient | mg/capsule | | | |
|---|---|---|---|---|
|  | 5 | 25 | 100 | 500 |
| Compound of formula I | 5 | 25 | 100 | 500 |
| Hydrous Lactose | 159 | 123 | 148 | — |
| Corn Starch | 25 | 35 | 40 | 70 |
| Talk | 10 | 15 | 10 | 25 |
| Magnesium Stearate | 1 | 2 | 2 | 5 |
| Total | 200 | 200 | 300 | 600 |

Manufacturing Procedure

1. Mix ingredients 1, 2 and 3 in a suitable mixer for 30 minutes.
2. Add ingredients 4 and 5 and mix for 3 minutes.
3. Fill into a suitable capsule.

The compound of formula I, lactose and corn starch are firstly mixed in a mixer and then in a comminuting machine. The mixture is returned to the mixer; the talc is added thereto and mixed thoroughly. The mixture is filled by machine into suitable capsules, e.g. hard gelatin capsules.

Example B-2

Soft Gelatin Capsules of the following composition are manufactured:

TABLE 5 possible soft gelatin capsule ingredient composition

| ingredient | mg/capsule |
|---|---|
| Compound of formula I | 5 |
| Yellow wax | 8 |
| Hydrogenated Soya bean oil | 8 |
| Partially hydrogenated plant oils | 34 |
| Soya bean oil | 110 |
| Total | 165 |

TABLE 6 possible soft gelatin capsule composition

| ingredient | mg/capsule |
|---|---|
| Gelatin | 75 |
| Glycerol 85% | 32 |
| Karion 83 | 8 (dry matter) |
| Titan dioxide | 0.4 |
| Iron oxide yellow | 1.1 |
| Total | 116.5 |

Manufacturing Procedure

The compound of formula I is dissolved in a warm melting of the other ingredients and the mixture is filled into soft gelatin capsules of appropriate size. The filled soft gelatin capsules are treated according to the usual procedures.

Example C

Suppositories of the following composition are manufactured:

TABLE 7

| possible suppository composition | |
| --- | --- |
| ingredient | mg/supp. |
| Compound of formula I | 15 |
| Suppository mass | 1285 |
| Total | 1300 |

Manufacturing Procedure

The suppository mass is melted in a glass or steel vessel, mixed thoroughly and cooled to 45° C. Thereupon, the finely powdered compound of formula I is added thereto and stirred until it has dispersed completely. The mixture is poured into suppository moulds of suitable size, left to cool; the suppositories are then removed from the moulds and packed individually in wax paper or metal foil.

Example D

Injection solutions of the following composition are manufactured:

TABLE 8

| possible injection solution composition | |
| --- | --- |
| ingredient | mg/injection solution. |
| Compound of formula I | 3 |
| Polyethylene Glycol 400 | 150 |
| acetic acid | q.s. ad pH 5.0 |
| water for injection solutions | ad 1.0 ml |

Manufacturing Procedure

The compound of formula I is dissolved in a mixture of Polyethylene Glycol 400 and water for injection (part). The pH is adjusted to 5.0 by acetic acid. The volume is adjusted to 1.0 ml by addition of the residual amount of water. The solution is filtered, filled into vials using an appropriate overage and sterilized.

Example E

Sachets of the following composition are manufactured:

TABLE 9

| possible sachet composition | |
| --- | --- |
| ingredient | mg/sachet |
| Compound of formula I | 50 |
| Lactose, fine powder | 1015 |
| Microcrystalline cellulose (AVICEL PH 102) | 1400 |
| Sodium carboxymethyl cellulose | 14 |
| Polyvinylpyrrolidon K 30 | 10 |
| Magnesium stearate | 10 |
| Flavoring additives | 1 |
| Total | 2500 |

Manufacturing Procedure

The compound of formula I is mixed with lactose, microcrystalline cellulose and sodium carboxymethyl cellulose and granulated with a mixture of polyvinylpyrrolidone in water. The granulate is mixed with magnesium stearate and the flavoring additives and filled into sachets.

EXPERIMENTAL PART

The following examples are provided for illustration of the invention. They should not be considered as limiting the scope of the invention, but merely as being representative thereof.

Experimental Part: Synthesis of Intermediates

Intermediates I1A and I1B 2-((S,2S)-2-Amino-3-fluoro-2-(2-fluorophenyl)-N-methylpropylsulfonimidoyl)-2-methylpropanenitrile (I1A) and 2-((R,2S)-2-amino-3-fluoro-2-(2-fluorophenyl)-N-methylpropylsulfonimidoyl)-2-methylpropanenitrile (I1B)

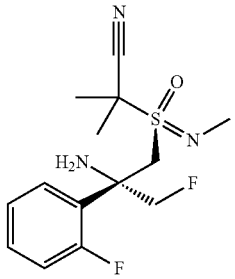

I1A

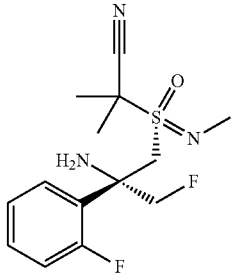

I1B

Step 1: (R)-N-(2-fluoro-1-(2-fluorophenyl)ethylidene)-2-methylpropane-2-sulfinamide (CAS #1404337-92-3, 2.8 g) and 2-(N,S-dimethylsulfonimidoyl)-2-methylpropanenitrile (CAS #1629090-52-3, 2.6 g) were dissolved in tetrahydrofuran (65 ml) and cooled to −75° C. Lithium bis(trimethylsilyl)amide (1.0 M in THF/ethylbenzene, 16.2 ml) was added dropwise and the mixture was stirred for 4 h at −75° C. After addition of aqueous half-concentrated ammonium chloride solution the cooling bath was removed and stirring was continued for 10 min. The mixture was extracted with EtOAc, dried over sodium sulphate, filtered and concentrated to dryness. The crude material was purified by flash chromatography (silica gel, 0% to 100% EtOAc in n-heptane) to give (R)-N-((2S)-1-(2-cyano-N-methylpropan-2-ylsulfonimidoyl)-3-fluoro-2-(2-fluorophenyl)propan-2-yl)-2-methylpropane-2-sulfinamide (1.05 g, mixture of epimers) as yellow viscous oil. MS: m/z=420.2 [M+H$^+$].

Step 2: (R)-N-((2S)-1-(2-cyano-N-methylpropan-2-ylsulfonimidoyl)-3-fluoro-2-(2-fluorophenyl)propan-2-yl)-2-methylpropane-2-sulfinamide (1.0 g, mixture of epimers)

was dissolved in MeOH (9.8 ml) and cooled to 0-5° C. After addition of HCl (4M in dioxane, 1.79 ml) the mixture was stirred for 3 h at 0-5° C. and stored overnight at 4° C. The reaction mixture was poured into aqueous saturated sodium bicarbonate solution and extracted 3 times with dichloromethane. The organic layers were dried over sodium sulphate, filtered and concentrated. The crude material was purified by flash chromatography (silica gel, 0% to 100% EtOAc in n-heptane) to give the first-eluting isomer 2-((S,2S)-2-amino-3-fluoro-2-(2-fluorophenyl)-N-methylpropylsulfonimidoyl)-2-methylpropanenitrile (211 mg) as light yellow viscous oil, MS: m/z=316.1 [M+H]$^+$ and the second-eluting isomer 2-((R,2S)-2-amino-3-fluoro-2-(2-fluorophenyl)-N-methylpropylsulfonimidoyl)-2-methylpropanenitrile (296 mg) as light yellow viscous oil, MS: m/z=316.1 [M+H]$^+$.

Intermediate I2A (1S,3S)-5-amino-3-(fluoromethyl)-3-(2-fluorophenyl)-6,6-dimethyl-1-(methylimino)-3,6-dihydro-2H-1,4-thiazine 1-oxide

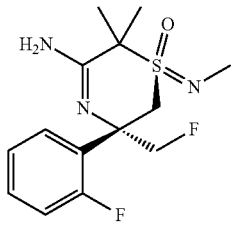 [SMILES: CN=[S@]1(=O)C[C@@](CF)(c2ccccc2F)N=C(N)C1(C)C]

2-((2S)-2-amino-3-fluoro-2-(2-fluorophenyl)-N-methylpropylsulfonimidoyl)-2-methylpropanenitrile (Intermediate I1A, 200 mg) and copper (I) chloride (65.3 mg) were combined under argon with ethanol (6.04 ml) to give a yellow suspension. The reaction mixture was stirred for 1.5 h at 75° C. The reaction mixture was cooled to room temperature and poured into 25% aqueous ammonia solution (3 ml) and water (12 ml) and extracted with dichloromethane. The organic layers were dried over MgSO$_4$ and concentrated in vacuo. The residue was diluted with EtOAc, filtered over a 20 g silica-NH$_2$-column, evaporated and dried to give (1S,3S)-5-amino-3-(fluoromethyl)-3-(2-fluorophenyl)-6,6-dimethyl-1-(methylimino)-3,6-dihydro-2H-1,4-thiazine 1-oxide (173 mg) as light yellow solid. MS: m/z=316.1 [M+H]$^+$.

Intermediate I3A tert-butyl ((1S,5S)-5-(5-ethynyl-2-fluorophenyl)-5-(fluoromethyl)-2,2-dimethyl-1-(methylimino)-1-oxido-5,6-dihydro-2H-1,4-thiazin-3-yl)carbamate

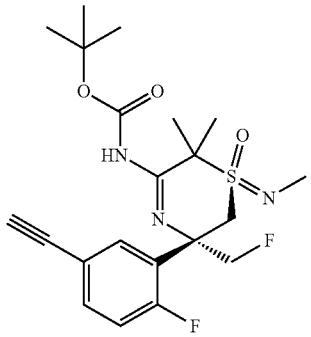 [SMILES: C#Cc1ccc(F)c([C@]2(CF)C[S@@](=O)(=NC)C(C)(C)C(NC(=O)OC(C)(C)C)=N2)c1]

Step 1: A solution of (1S,3S)-5-amino-3-(fluoromethyl)-3-(2-fluorophenyl)-6,6-dimethyl-1-(methylimino)-3,6-dihydro-2H-1,4-thiazine 1-oxide (Intermediate I2A, 165 mg) in dichloromethane (7.27 ml) was cooled under argon in an ice bath. Trifluoromethanesulfonic acid (1.57 g) was added and the solution was allowed to warm to room temperature. N-iodosuccinimide (141 mg) was added and the mixture was stirred for 3.5 h at room temperature. More N-iodosuccinimide (23.5 mg) was added and stirring was continued for 2 h. More N-iodosuccinimide (23.5 mg) was added and stirred overnight. The dark purple mixture was added dropwise to a sat. aqueous NaHCO$_3$ solution (25 ml). The aqueous layer was separated and extracted once more with dichloromethane. The organic layers were washed with aqueous 0.1M sodiumthiosulphate solution, dried over MgSO4, filtered and concentrated in vacuo. The crude material was purified by flash chromatography (NH$_2$-modified silica gel, 0% to 100% EtOAc in n-heptane) to give (1S,3S)-5-amino-3-(2-fluoro-5-iodophenyl)-3-(fluoromethyl)-6,6-dimethyl-1-(methylimino)-3,6-dihydro-2H-1,4-thiazine 1-oxide (150 mg) as off-white solid. MS: m/z=442.1 [M+H]$^+$.

Step 2: (1S,3S)-5-Amino-3-(2-fluoro-5-iodophenyl)-3-(fluoromethyl)-6,6-dimethyl-1-(methylimino)-3,6-dihydro-2H-1,4-thiazine 1-oxide (145 mg) was dissolved in dichloromethane (4.1 ml) under argon. After addition of BOC-Anhydride (75.3 mg) the mixture was stirred for 1 day. The reaction mixture was evaporated and the crude material was purified by flash chromatography (silica gel, 0% to 50% EtOAc in n-heptane) to give tert-butyl ((1S,5S)-5-(2-fluoro-5-iodophenyl)-5-(fluoromethyl)-2,2-dimethyl-1-(methylimino)-1-oxido-5,6-dihydro-2H-1,4-thiazin-3-yl)carbamate (169 mg) as off-white solid. MS: m/z=542.2 [M+H]$^+$.

Step 3: tert-Butyl ((1S,5S)-5-(2-fluoro-5-iodophenyl)-5-(fluoromethyl)-2,2-dimethyl-1-(methylimino)-1-oxido-5,6-dihydro-2H-1,4-thiazin-3-yl)carbamate (162 mg), ethynyltrimethylsilane (58.8 mg), bis(triphenylphosphine)palladium (II) chloride (14.7 mg), copper (1) iodide (2.28 mg) and triethylamine (90.8 mg) were mixed under argon with THF (2.66 ml) and stirred for 1 h at room temperature. The mixture was diluted with EtOAc and filtered through a glass fiber filter. The filtrate was evaporated and the crude material was purified by flash chromatography (silica gel, 0% to 100% EtOAc in n-heptane) to give tert-butyl ((1S,5S)-5-(2-fluoro-5-((trimethylsilyl)ethynyl)phenyl)-5-(fluoromethyl)-2,2-dimethyl-1-(methylimino)-1-oxido-5,6-dihydro-2H-1,4-thiazin-3-yl)carbamate (147 mg) as off-white solid. MS: m/z=512.2 [M+H]$^+$.

Step 4: To remove traces of Cu and Pd, the starting material was treated with a scavenger: tert-butyl ((1S,5S)-5-(2-fluoro-5-((trimethylsilyl)ethynyl)phenyl)-5-(fluoroethyl)-2,2-dimethyl-1-(methylimino)-1-oxido-5,6-dihydro-2H-1,4-thiazin-3-yl)carbamate (142 mg) was dissolved in dichloromethane (4 ml) under argon. After addition of 3-mercaptopropyl ethyl sulfide silica (96.4 mg) the mixture was stirred under argon overnight. The scavenger was filtered off and washed well with ethyl acetate. The almost colorless solution was evaporated, re-dissolved in dichloromethane (4.04 ml) and cooled to 0° C. After addition of tetrabutylammonium fluoride (1M in THF, 305 μl) the mixture was stirred for 45 min at 0° C. The mixture was diluted with dichloromethane and washed with water. The org. layer was dried over sodium sulphate, filtered and evaporated to give tert-butyl ((1S,5S)-5-(5-ethynyl-2-fluorophenyl)-5-(fluoromethyl)-2,2-dimethyl-1-(methylimino)-1-oxido-5,6-dihydro-2H-1,4-thiazin-3-yl)carbamate (122 mg) as off-white solid. MS: m/z=440.2 [M+H]$^+$. The product was used in the next step without further purification.

Intermediate I2B (1R,3S)-5-amino-3-(fluoromethyl)-3-(2-fluorophenyl)-6,6-dimethyl-1-(methylimino)-3,6-dihydro-2H-1,4-thiazine 1-oxide

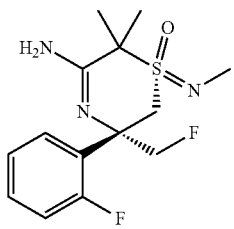 [SMILES: CN=[S@@]1(=O)C[C@@](CF)(c2ccccc2F)N=C(N)C1(C)C]

In analogy to the synthesis of Intermediate I2A, 2-((R,2S)-2-amino-3-fluoro-2-(2-fluorophenyl)-N-methylpropyl-sulfonimidoyl)-2-methylpropanenitrile (Intermediate I1B) was converted to (1R,3S)-5-amino-3-(fluoromethyl)-3-(2-fluorophenyl)-6,6-dimethyl-1-(methylimino)-3,6-dihydro-2H-1,4-thiazine 1-oxide by treatment with CuCl in ethanol at 75° C. for 5 h. Light yellow solid. MS: m/z=316.1 [M+H]$^+$

Intermediate I3B tert-butyl ((1R,5S)-5-(5-ethynyl-2-fluorophenyl)-5-(fluoromethyl)-2,2-dimethyl-1-(methylimino)-1-oxido-5,6-dihydro-2H-1,4-thiazin-3-yl)carbamate

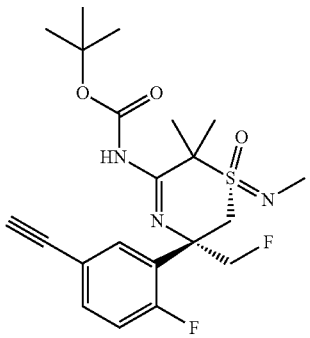 [SMILES: C#Cc1ccc(F)c([C@]2(CF)C[S@](=O)(=NC)C(C)(C)C(NC(=O)OC(C)(C)C)=N2)c1]

Step 1: In analogy to the synthesis of Intermediate I3A, step 1, (1R,3S)-5-amino-3-(fluoromethyl)-3-(2-fluorophenyl)-6,6-dimethyl-1-(methylimino)-3,6-dihydro-2H-1,4-thiazine 1-oxide (Intermediate I2B) was converted to (1R,3S)-5-amino-3-(2-fluoro-5-iodophenyl)-3-(fluoromethyl)-6,6-dimethyl-1-(methylimino)-3,6-dihydro-2H-1,4-thiazine 1-oxide by treatment with N-iodosuccinimide in dichloromethane in the presence of trifluoromethanesulfonic acid. Light yellow solid. MS: m/z=442.1 [M+H]$^+$.

Step 2: In analogy to the synthesis of Intermediate I3A, step 2, (1R,3S)-5-amino-3-(2-fluoro-5-iodophenyl)-3-(fluoromethyl)-6,6-dimethyl-1-(methylimino)-3,6-dihydro-2H-1,4-thiazine 1-oxide was converted to tert-butyl ((1R,5S)-5-(2-fluoro-5-iodophenyl)-5-(fluoromethyl)-2,2-dimethyl-1-(methylimino)-1-oxido-5,6-dihydro-2H-1,4-thiazin-3-yl)carbamate by treatment with BOC-Anhydride in dichloromethane. Off-white solid. MS: m/z=542.0 [M+H$^+$].

Step 3: In analogy to the synthesis of Intermediate I3A, step 3, tert-butyl ((1R,5S)-5-(2-fluoro-5-iodophenyl)-5-(fluoromethyl)-2,2-dimethyl-1-(methylimino)-1-oxido-5,6-dihydro-2H-1,4-thiazin-3-yl)carbamate was converted to tert-butyl ((1R,5S)-5-(2-fluoro-5-((trimethylsilyl)ethynyl)phenyl)-5-(fluoromethyl)-2,2-dimethyl-1-(methylimino)-1-oxido-5,6-dihydro-2H-1,4-thiazin-3-yl)carbamate by treatment with ethynyltrimethylsilane in THF in the presence of bis(triphenylphosphine)palladium (II) chloride, copper (I) iodide and triethylamine. Off-white solid. MS: m/z=512.2 [M+H]$^+$.

Step 4: In analogy to the synthesis of Intermediate I3A, step 4, tert-butyl ((1R,5S)-5-(2-fluoro-5-((trimethylsilyl)ethynyl)phenyl)-5-(fluoromethyl)-2,2-dimethyl-1-(methylimino)-1-oxido-5,6-dihydro-2H-1,4-thiazin-3-yl)carbamate was converted to tert-butyl ((1R,5S)-5-(5-ethynyl-2-fluorophenyl)-5-(fluoromethyl)-2,2-dimethyl-1-(methylimino)-1-oxido-5,6-dihydro-2H-1,4-thiazin-3-yl)carbamate by treatment with tetrabutylammonium fluoride in dichloromethane. Off-white solid. MS: m/z=440.2 [M+H]$^+$.

Intermediates I4A and I4B (R)-N-((R)-1-((R)-2-cyano-N-methylpropan-2-ylsulfonimidoyl)-2-(2-fluorophenyl)propan-2-yl)-2-methylpropane-2-sulfinamide (I4A) and (R)-N-((R)-1-((S)-2-cyano-N-methylpropan-2-ylsulfonimidoyl)-2-(2-fluorophenyl)propan-2-yl)-2-methylpropane-2-sulfinamide (I4B)

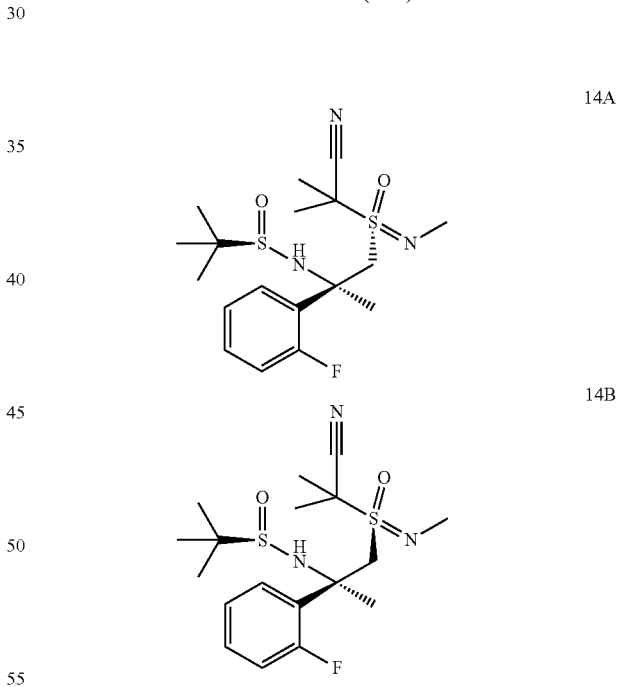

2-(N,S-dimethylsulfonimidoyl)-2-methylpropanenitrile (CAS #1629090-52-3, 2.93 g) was dissolved in dichloromethane (60 ml) and cooled to −75° C. under argon. Lithium bis(trimethylsilyl)amide, 1.0 M in THF/ethylbenzene (18.3 ml) was added dropwise and the mixture was stirred for 1 h at −70° C. A solution of (R)-N-(1-(2-fluorophenyl)ethylidene)-2-methylpropane-2-sulfinamide (CAS #1606166-80-6, 3.4 g) in dichloromethane (17.5 ml) was added dropwise within 5 min at −75° C. Stirring was continued at −75° C. for 80 min. Lithium bis(trimethylsilyl)amide, 1.0 M in THF/ethylbenzene (10.5 ml) was added dropwise and the mixture was stirred for 70 min at −70° C. The reaction was quenched by addition of aqueous half concentrated ammonium chloride solution. The temperature was allowed to rise to +5° C. The layers were separated and the org. layer was washed 3 times with water, dried over sodium sulphate and concentrated. The crude material was purified by flash chromatography (silica gel, 0% to 100% EtOAc in n-heptane) to give the first-eluting isomer (R)-N-((R)-1-((R)-2-cyano-N-methylpropan-2-ylsulfonimidoyl)-2-(2-fluorophenyl)propan-2-yl)-2-methylpropane-2-sulfinamide (Intermediate I4A, 1.135 g, contains approximately 5% Intermediate I4B) as light yellow waxy solid, MS: m/z=402.2 [M+H]$^+$ and the second-eluting isomer (R)-N-((R)-1-((S)-2-cyano-N-methylpropan-2-ylsulfonimidoyl)-2-(2-fluorophenyl)propan-2-yl)-2-methylpropane-2-sulfinamide (Intermediate I4B, 0.692 g, contains approximately 10% Intermediate I4A) as light yellow oil, MS: m/z=402.2 [M+H]$^+$.

Intermediate I5A (1R,3R)-5-amino-3-(2-fluorophenyl)-3,6,6-trimethyl-1-(methylimino)-3,6-dihydro-2H-1,4-thiazine 1-oxide

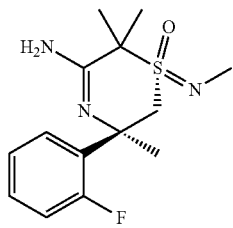 [SMILES: CN=[S@@]1(=O)C[C@@](C)(c2ccccc2F)N=C(N)C1(C)C]

Step 1: In analogy to the synthesis of Intermediates I1A and I1B, step 2, (R)-N-((R)-1-((R)-2-cyano-N-methylpropan-2-ylsulfonimidoyl)-2-(2-fluorophenyl)propan-2-yl)-2-methylpropane-2-sulfinamide (Intermediate I4A) was converted to 2-((R,2R)-2-amino-2-(2-fluorophenyl)-N-methylpropylsulfonimidoyl)-2-methylpropanenitrile by treatment with HCl in methanol and dioxane at 0-5° C. Colorless oil. MS: m/z=298.1 [M+H]$^+$.

Step 2: In analogy to the synthesis of Intermediate I2A, 2-((R,2R)-2-amino-2-(2-fluorophenyl)-N-methylpropylsulfonimidoyl)-2-methylpropanenitrile was converted to (1R,3R)-5-amino-3-(2-fluorophenyl)-3,6,6-trimethyl-1-(methylimino)-3,6-dihydro-2H-1,4-thiazine 1-oxide by treatment with CuCl in ethanol at 75° C. for 2 h. Off-white solid. MS: m/z=298.1 [M+H]$^+$.

Intermediate I6A tert-butyl ((1R,5R)-5-(5-ethynyl-2-fluorophenyl)-2,2,5-trimethyl-1-(methylimino)-1-oxido-5,6-dihydro-2H-1,4-thiazin-3-yl) carbamate

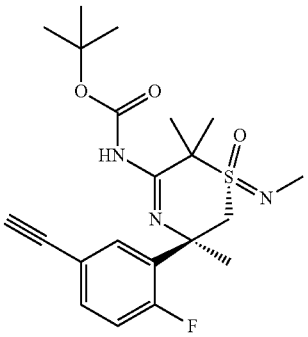 [SMILES: C#Cc1ccc(F)c([C@]2(C)C[S@](=O)(=NC)C(C)(C)C(NC(=O)OC(C)(C)C)=N2)c1]

Step 1: In analogy to the synthesis of Intermediate I3A, step 1, (1R,3R)-5-amino-3-(2-fluorophenyl)-3,6,6-trimethyl-1-(methylimino)-3,6-dihydro-2H-1,4-thiazine 1-oxide (Intermediate I5A) was converted to (1R,3R)-5-amino-3-(2-fluoro-5-iodophenyl)-3,6,6-trimethyl-1-(methylimino)-3,6-dihydro-2H-1,4-thiazine 1-oxide by treatment with N-iodosuccinimide in dichloromethane in the presence of trifluoromethanesulfonic acid. Light yellow solid. MS: m/z=424.0 [M+H]$^+$.

Step 2: In analogy to the synthesis of Intermediate I3A, step 2, (1R,3R)-5-amino-3-(2-fluoro-5-iodophenyl)-3,6,6-trimethyl-1-(methylimino)-3,6-dihydro-2H-1,4-thiazine 1-oxide was converted to tert-butyl ((1R,5R)-5-(2-fluoro-5-iodophenyl)-2,2,5-trimethyl-1-(methylimino)-1-oxido-5,6-dihydro-2H-1,4-thiazin-3-yl)carbamate by treatment with BOC-Anhydride in dichloromethane. Off-white solid. MS: m/z=522.2 [M−H]$^-$.

Step 3: In analogy to the synthesis of Intermediate I3A, step 3, tert-butyl ((1R,5R)-5-(2-fluoro-5-iodophenyl)-2,2,5-trimethyl-1-(methylimino)-1-oxido-5,6-dihydro-2H-1,4-thiazin-3-yl)carbamate was converted to tert-butyl ((1R,5R)-5-(2-fluoro-5-((trimethylsilyl)ethynyl)phenyl)-2,2,5-trimethyl-1-(methylimino)-1-oxido-5,6-dihydro-2H-1,4-thiazin-3-yl)carbamate by treatment with ethynyltrimethylsilane in THF in the presence of bis(triphenylphosphine)palladium (II) chloride, copper (I) iodide and triethylamine. Light brown solid. MS: m/z=394.2 [M+H−BOC]$^+$.

Step 4: In analogy to the synthesis of Intermediate I3A, step 4, tert-butyl ((1R,5R)-5-(2-fluoro-5-((trimethylsilyl)ethynyl)phenyl)-2,2,5-trimethyl-1-(methylimino)-1-oxido-5,6-dihydro-2H-1,4-thiazin-3-yl)carbamate was converted to tert-butyl ((1R,5R)-5-(5-ethynyl-2-fluorophenyl)-2,2,5-trimethyl-1-(methylimino)-1-oxido-5,6-dihydro-2H-1,4-thiazin-3-yl)carbamate by treatment with tetrabutylammonium fluoride in dichloromethane. Colorless foam. MS: m/z=420.2 [M−H]$^-$.

Intermediate I5B (1S,3R)-5-amino-3-(2-fluorophenyl)-3,6,6-trimethyl-1-(methylimino)-3,6-dihydro-2H-1,4-thiazine 1-oxide

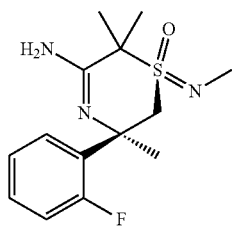 [SMILES: CN=[S@]1(=O)C[C@@](C)(c2ccccc2F)N=C(N)C1(C)C]

Step 1: In analogy to the synthesis of Intermediates I1A and I1B, step 2, (R)-N-((R)-1-((S)-2-cyano-N-methylpropan-2-ylsulfonimidoyl)-2-(2-fluorophenyl)propan-2-yl)-2-methylpropane-2-sulfinamide (Intermediate I4B) was converted to 2-((S,2R)-2-amino-2-(2-fluorophenyl)-N-methylpropylsulfonimidoyl)-2-methylpropanenitrile by treatment with HCl in methanol and dioxane at 0-5° C. Colorless oil. MS: m/z=298.1 [M+H]$^+$.

Step 2: In analogy to the synthesis of Intermediate I2A, 2-((S,2R)-2-amino-2-(2-fluorophenyl)-N-methylpropylsulfonimidoyl)-2-methylpropanenitrile was converted to (1S,3R)-5-amino-3-(2-fluorophenyl)-3,6,6-trimethyl-1-(methylimino)-3,6-dihydro-2H-1,4-thiazine 1-oxide by treatment with CuCl in ethanol at 75° C. for 2 h. Off-white foam. MS: m/z=298.1 [M+H]$^+$.

Intermediate I6B tert-butyl ((1S,5R)-5-(5-ethynyl-2-fluorophenyl)-2,2,5-trimethyl-1-(methylimino)-1-oxido-5,6-dihydro-2H-1,4-thiazin-3-yl) carbamate

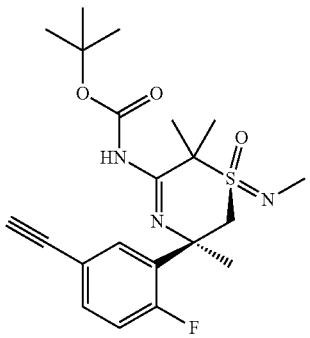 [SMILES: C#Cc1ccc(F)c([C@]2(C)C[S@@](=O)(=NC)C(C)(C)C(NC(=O)OC(C)(C)C)=N2)c1]

Step 1: In analogy to the synthesis of Intermediate I3A, step 1, (1S,3R)-5-amino-3-(2-fluorophenyl)-3,6,6-trimethyl-1-(methylimino)-3,6-dihydro-2H-1,4-thiazine 1-oxide (Intermediate I5B) was converted to (1S,3R)-5-amino-3-(2-fluoro-5-iodophenyl)-3,6,6-trimethyl-1-(methylimino)-3,6-dihydro-2H-1,4-thiazine 1-oxide by treatment with N-iodosuccinimide in dichloromethane in the presence of trifluoromethanesulfonic acid. Off-white solid. MS: m/z=424.1 [M+H]$^+$.

Step 2: In analogy to the synthesis of Intermediate I3A, step 2, (1S,3R)-5-amino-3-(2-fluoro-5-iodophenyl)-3,6,6-trimethyl-1-(methylimino)-3,6-dihydro-2H-1,4-thiazine 1-oxide was converted to tert-butyl ((1S,5R)-5-(2-fluoro-5-iodophenyl)-2,2,5-trimethyl-1-(methylimino)-1-oxido-5,6-dihydro-2H-1,4-thiazin-3-yl)carbamate by treatment with BOC-Anhydride in dichloromethane. Colorless solid. MS: m/z=522.2 [M–H]$^-$.

Step 3: In analogy to the synthesis of Intermediate I3A, step 3, tert-butyl ((1S,5R)-5-(2-fluoro-5-iodophenyl)-2,2,5-trimethyl-1-(methylimino)-1-oxido-5,6-dihydro-2H-1,4-thiazin-3-yl)carbamate was converted to tert-butyl ((1S,5R)-5-(2-fluoro-5-((trimethylsilyl)ethynyl)phenyl)-2,2,5-trimethyl-1-(methylimino)-1-oxido-5,6-dihydro-2H-1,4-thiazin-3-yl)carbamate by treatment with ethynyltrimethylsilane in THF in the presence of bis(triphenylphosphine)palladium (II) chloride, copper (I) iodide and triethylamine. Light yellow solid. MS: m/z=494.2 [M+H]$^+$.

Step 4: In analogy to the synthesis of Intermediate I3A, step 4, tert-butyl ((1S,5R)-5-(2-fluoro-5-((trimethylsilyl)ethynyl)phenyl)-2,2,5-trimethyl-1-(methylimino)-1-oxido-5,6-dihydro-2H-1,4-thiazin-3-yl)carbamate was converted to tert-butyl ((1S,5R)-5-(5-ethynyl-2-fluorophenyl)-2,2,5-trimethyl-1-(methylimino)-1-oxido-5,6-dihydro-2H-1,4-thiazin-3-yl)carbamate by treatment with tetrabutylammonium fluoride in dichloromethane. Colorless foam. MS: m/z=322.1 [M+H-BOC]$^1$.

Intermediate I7A

N-[(1R)-2-[S-(1-cyano-1-methyl-ethyl)-N-(trideuteriomethyl)sulfonimidoyl]-1-(2-fluorophenyl)-1-methyl-ethyl]-2-methyl-propane-2-sulfinamide

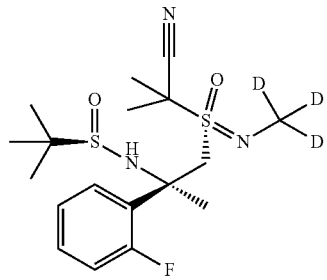 [SMILES: [2H]C([2H])([2H])N=[S@@](=O)(C[C@](C)(N[S@](=O)C(C)(C)C)c1ccccc1F)C(C)(C)C#N]

Step 1: 2-Methyl-2-(S-methylsulfonimidoyl)propanenitrile (6.68 g) was dissolved in dimethoxyethane (109 ml) and cooled to 0-5° C. After addition of sodium hydride (60% dispersion in mineral oil, 1.89 g) the mixture was stirred for 15 min at 0-5° C., the cooling bath was removed and the mixture was stirred for 1 h at room temperature. The mixture was cooled again to 0-5° C. After addition of iodomethane-D3 (6.56 g) stirring was continued for 1 h at room temperature followed by 18 h at 50° C. The mixture was allowed to cool to room temperature. After addition of aqueous saturated sodium bicarbonate solution the mixture was extracted with ethyl acetate. The organic layers were washed with brine, combined, dried over sodium sulphate and concentrated. The crude material was purified by flash chromatography (silica gel, 0% to 100% EtOAc in n-heptane) to give 2-methyl-2-[S-methyl-N-(trideuteriomethyl)sulfonimidoyl] propanenitrile as light brown oil. MS: m/z=164.1 [M+H]$^+$.

Step 2: In analogy to the synthesis of Intermediate I4A, 2-methyl-2-[S-methyl-N-(trideuteriomethyl)sulfonimidoyl] propanenitrile was reacted first with lithium bis(trimethylsilyl)amide followed by treatment with (R)-N-(1-(2-fluorophenyl)ethylidene)-2-methylpropane-2-sulfinamide to give after chromatography (silica gel, 0% to 100% EtOAc in n-heptane) the first-eluting isomer N-[(1R)-2-[S-(1-cyano-1-methyl-ethyl)-N-(trideuteriomethyl)sulfonimidoyl]-1-(2-fluorophenyl)-1-methyl-ethyl]-2-methyl-propane-2-sulfinamide (Intermediate I7A, contains approximately 5% of the second-eluting isomer) as light yellow solid, MS: m/z=405.2 [M+H]$^+$ Intermediate I8A (1R,3R)-3-(2-fluorophenyl)-3,6,6-trimethyl-1-oxo-1-(trideuteriomethylimino)-2H-1,4-thiazin-5-amine

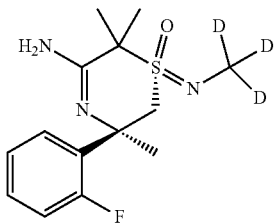 [SMILES: [2H]C([2H])([2H])N=[S@@]1(=O)C[C@@](C)(c2ccccc2F)N=C(N)C1(C)C]

Step 1: In analogy to the synthesis of Intermediates I1A and I1B, step 2, N-[(1R)-2-[S-(1-cyano-1-methyl-ethyl)-N-(trideuteriomethyl)sulfonimidoyl]-1-(2-fluorophenyl)-1-methyl-ethyl]-2-methyl-propane-2-sulfinamide (Intermediate I7A) was converted to 2-[S-[(2R)-2-amino-2-(2-fluorophenyl)propyl]-N-(trideuteriomethyl)sulfonimidoyl]-2-methyl-propanenitrile by treatment with HCl in methanol and dioxane at 0-5° C. Colorless oil. MS: m/z=301.1 [M+H]$^+$.

Step 2: In analogy to the synthesis of Intermediate I2A, 2-[S-[(2R)-2-amino-2-(2-fluorophenyl)propyl]-N-(trideuteriomethyl)sulfonimidoyl]-2-methyl-propanenitrile was converted to (1R,3R)-3-(2-fluorophenyl)-3,6,6-trimethyl-1-oxo-1-(trideuteriomethylimino)-2H-1,4-thiazin-5-amine by treatment with CuCl in ethanol at 75° C. Off-white solid. MS: m/z=301.1 [M+H]$^+$.

Intermediate I9A tert-Butyl N-[(1R,3R)-3-(5-ethynyl-2-fluoro-phenyl)-3,6,6-trimethyl-1-oxo-1-(trideuteriomethylimino)-2H-1,4-thiazin-5-yl]carbamate

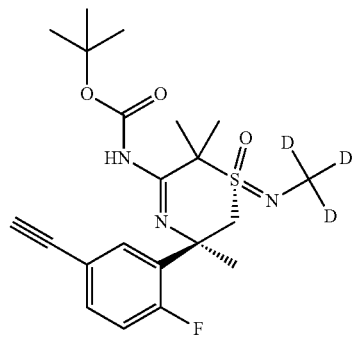 [SMILES: [2H]C([2H])([2H])N=[S@@]1(=O)C[C@@](C)(c2cc(C#C)ccc2F)N=C(NC(=O)OC(C)(C)C)C1(C)C]

Step 1: In analogy to the synthesis of Intermediate I3A, step 1, (1R,3R)-3-(2-fluorophenyl)-3,6,6-trimethyl-1-oxo-1-(trideuteriomethylimino)-2H-1,4-thiazin-5-amine (Intermediate I8A) was converted to (1R,3R)-3-(2-fluoro-5-iodo-phenyl)-3,6,6-trimethyl-1-oxo-1-(trideuteriomethylimino)-2H-1,4-thiazin-5-amine by treatment with N-iodosuccinimide in dichloromethane in the presence of trifluoromethanesulfonic acid. Off-white solid. MS: m/z=427.1 [M+H]$^+$.

Step 2: In analogy to the synthesis of Intermediate I3A, step 2, (1R,3R)-3-(2-fluoro-5-iodo-phenyl)-3,6,6-trimethyl-1-oxo-1-(trideuteriomethylimino)-2H-1,4-thiazin-5-amine was converted to tert-butyl N-[(1R,3R)-3-(2-fluoro-5-iodo-phenyl)-3,6,6-trimethyl-1-oxo-1-(trideuteriomethylimino)-2H-1,4-thiazin-5-yl]carbamate by treatment with BOC-Anhydride in dichloromethane. Colorless solid. MS: m/z=527.2 [M+H]$^+$.

Step 3: In analogy to the synthesis of Intermediate I3A, step 3, tert-butyl N-[(1R,3R)-3-(2-fluoro-5-iodo-phenyl)-3,6,6-trimethyl-1-oxo-1-(trideuteriomethylimino)-2H-1,4-thiazin-5-yl]carbamate was converted to tert-butyl N-[(1R,3R)-3-[2-fluoro-5-(2-trimethylsilylethynyl)phenyl]-3,6,6-trimethyl-1-oxo-1-(trideuteriomethylimino)-2H-1,4-thiazin-5-yl]carbamate by treatment with ethynyltrimethylsilane in THF in the presence of bis(triphenylphosphine)palladium (II) chloride, copper (I) iodide and triethylamine. Light brown solid. MS: m/z=497.3 [M+H]$^+$.

Step 4: In analogy to the synthesis of Intermediate I3A, step 4, tert-butyl N-[(1R,3R)-3-[2-fluoro-5-(2-trimethylsilylethynyl)phenyl]-3,6,6-trimethyl-1-oxo-1-(trideuteriomethylimino)-2H-1,4-thiazin-5-yl]carbamate was converted to tert-butyl N-[(1R,3R)-3-(5-ethynyl-2-fluoro-phenyl)-3,6,6-trimethyl-1-oxo-1-(trideuteriomethylimino)-2H-1,4-thiazin-5-yl]carbamate by treatment with tetrabutylammonium fluoride in dichloromethane. Colorless solid. MS: m/z=425.3 [M+H]$^+$.

Intermediates I10A and I10B (R)-N-((R)-1-((R)-1-cyano-N-methylcyclopentanesulfonimidoyl)-2-(2-fluorophenyl)propan-2-yl)-2-methylpropane-2-sulfinamide (I10A) and (R)-N-((R)-1-((S)-1-cyano-N-methylcyclopentanesulfonimidoyl)-2-(2-fluorophenyl)propan-2-yl)-2-methylpropane-2-sulfinamide (I10B)

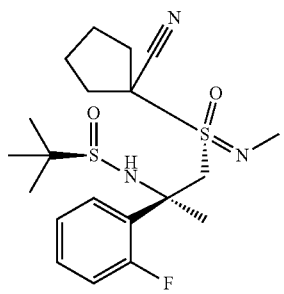

-continued

I10B

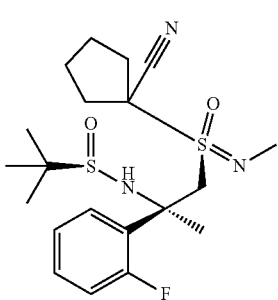

Step 1: To a stirred solution of 1-(methylthio)cyclopentanecarbonitrile (7.91 g) in dichloromethane (128 ml) 3-chlorobenzoperoxoic acid (10.9 g) was added in one portion at 0° C. The white suspension was stirred at 0° C. for 30 min. The mixture was filtered. A 1M solution of potassium carbonate (1/3) was mixed with a half sat. solution of sodium thiosulfate (2/3). The organic layer was extracted immediately with 1×20 ml of this solution. The aqueous layer was back-extracted with 1×30 ml dichloromethane. The combined organic layers were dried over Na$_2$SO$_4$ and concentrated. The crude 1-(methylsulfinyl)cyclopentanecarbonitrile was used for the next step without further purification.

Step 2: 1-(Methylsulfinyl)cyclopentanecarbonitrile (6.749 g), 4-nitrobenzenesulfonamide (9.37 g), silver nitrate (525 mg) and 4,4',4"-tri-tert-butyl-2,2':6',2"-terpyridine (1.24 g) were combined in MeCN (129 ml). After 20 min, (diacetoxyiodo)benzene (18.7 g) was added and stirred for 24 h at 60° C. The solution was filtered, and the precipitate was washed with dichloromethane. The filtrate was concentrated and the crude material was purified by flash chromatography (silica gel, 80 g, 100% DCM) to give N-[(1-cyanocyclopentyl)-methyl-oxo-λ$^6$-sulfanylidene]-4-nitro-benzenesulfonamide (12.816 g).

Step 3: To a solution of N-[(1-cyanocyclopentyl)-methyl-oxo-λ$^6$-sulfanylidene]-4-nitro-benzenesulfonamide (13.192 g) in acetonitrile (246 ml) was added at 23° C. cesium carbonate (21.6 g) followed by the addition of thiophenol (6.51 g) and the reaction mixture was stirred at 23° C. for 6 h. Poured into brine (100 ml), extracted twice with ethyl acetate (50 ml), dried the organic layers over Na2SO4, filtered, and concentrated to dryness. The crude material was purified by flash chromatography (silica gel, 80 g, 20% to 100% EtOAc in heptane) to give 1-(S-methylsulfonimidoyl)cyclopentanecarbonitrile (5.433 g) as a slight yellow oil. MS: m/z=172.9 [M+H]$^+$.

Step 4: In analogy to the synthesis of Intermediate I7A, step 1, 1-(S-methylsulfonimidoyl)cyclopentanecarbonitrile was alkylated with methyl iodide in the presence of sodium hydride to give 1-(N,S-dimethylsulfonimidoyl)cyclopentane-1-carbonitrile as light yellow oil. MS: m/z=186.1 [M]$^+$.

Step 5: In analogy to the synthesis of Intermediate I4A, 1-(N,S-dimethylsulfonimidoyl)cyclopentane-1-carbonitrile was reacted first with lithium bis(trimethylsilyl)amide followed by treatment with (R)-N-(1-(2-fluorophenyl)ethylidene)-2-methylpropane-2-sulfinamide to give after chromatography (silica gel, 0% to 100% EtOAc in n-heptane) the first-eluting isomer (R)-N-((R)-1-((R)-1-cyano-N-methylcyclopentanesulfonimidoyl)-2-(2-fluorophenyl)propan-2-yl)-2-methylpropane-2-sulfinamide (Intermediate I10A) as light brown solid, MS: m/z=428.2 [M+H]$^+$; and the second-eluting isomer (R)-N-((R)-1-((S)-1-cyano-N-methylcyclopentanesulfonimidoyl)-2-(2-fluorophenyl)propan-2-yl)-2-methylpropane-2-sulfinamide (Intermediate I10B) as light yellow solid, MS: m/z=428.3 [M+H]$^+$.

Intermediate I11A (6R,8R)-10-amino-8-(2-fluorophenyl)-8-methyl-6-(methylimino)-6-thia-9-azaspiro[4.5]dec-9-ene 6-oxide

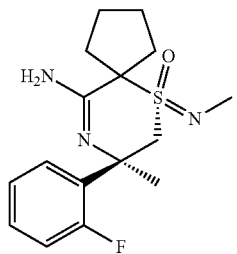 [SMILES: CN=[S@@]1(=O)C[C@@](C)(c2ccccc2F)N=C(N)C12CCCC2]

Step 1: In analogy to the synthesis of Intermediates I1A and I1B, step 2, (R)-N-((R)-1-((R)-1-cyano-N-methylcyclopentanesulfonimidoyl)-2-(2-fluorophenyl)propan-2-yl)-2-methylpropane-2-sulfinamide (Intermediate I10A) was converted to 1-((R,2R)-2-amino-2-(2-fluorophenyl)-N-methylpropylsulfonimidoyl)cyclopentanecarbonitrile by treatment with HCl in methanol and dioxane at 0-5° C. Colorless oil. MS: m/z=324.2 [M+H]$^+$.

Step 2: In analogy to the synthesis of Intermediate I2A, 1-((R,2R)-2-amino-2-(2-fluorophenyl)-N-methylpropylsulfonimidoyl)cyclopentanecarbonitrile was converted to (6R,8R)-10-amino-8-(2-fluorophenyl)-8-methyl-6-(methylimino)-6-thia-9-azaspiro[4.5]dec-9-ene 6-oxide by treatment with CuCl in ethanol at 75° C. Light brown gum. MS: m/z=324.2 [M+H]$^+$.

Intermediate I12A tert-butyl ((6R,8R)-8-(5-ethynyl-2-fluorophenyl)-8-methyl-6-(methylimino)-6-oxido-6-thia-9-azaspiro[4.5]dec-9-en-10-yl)carbamate

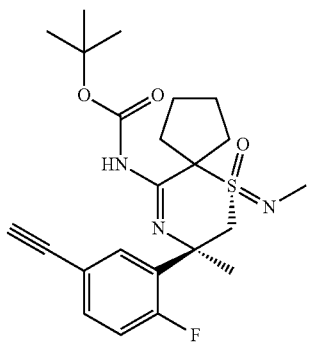 [SMILES: C#Cc1ccc(F)c([C@]2(C)C[S@](=O)(=NC)C3(CCCC3)C(NC(=O)OC(C)(C)C)=N2)c1]

Step 1: In analogy to the synthesis of Intermediate I3A, step 1, (6R,8R)-10-amino-8-(2-fluorophenyl)-8-methyl-6-(methylimino)-6-thia-9-azaspiro[4.5]dec-9-ene 6-oxide (Intermediate I11A) was converted to (6R,8R)-10-amino-8-(2-fluoro-5-iodophenyl)-8-methyl-6-(methylimino)-6-thia-9-azaspiro[4.5]dec-9-ene 6-oxide by treatment with N-iodosuccinimide in dichloromethane in the presence of trifluoromethanesulfonic acid. Brown foam. MS: m/z=450.1 [M+H]⁺.

Step 2: In analogy to the synthesis of Intermediate I3A, step 2, (6R,8R)-10-amino-8-(2-fluoro-5-iodophenyl)-8-methyl-6-(methylimino)-6-thia-9-azaspiro[4.5]dec-9-ene 6-oxide was converted to tert-butyl ((6R,8R)-8-(2-fluoro-5-iodophenyl)-8-methyl-6-(methylimino)-6-oxido-6-thia-9-azaspiro[4.5]dec-9-en-10-yl)carbamate by treatment with BOC-Anhydride in dichloromethane. Off-white solid. MS: m/z=550.3 [M+H]⁺.

Step 3: In analogy to the synthesis of Intermediate I3A, step 3, tert-butyl ((6R,8R)-8-(2-fluoro-5-iodophenyl)-8-methyl-6-(methylimino)-6-oxido-6-thia-9-azaspiro[4.5]dec-9-en-10-yl)carbamate was converted to tert-butyl ((6R,8R)-8-(2-fluoro-5-((trimethylsilyl)ethynyl)phenyl)-8-methyl-6-(methylimino)-6-oxido-6-thia-9-azaspiro[4.5]dec-9-en-10-yl)carbamate by treatment with ethynyltrimethylsilane in THF in the presence of bis(triphenylphosphine)palladium (II) chloride, copper (I) iodide and triethylamine. Colorless solid. MS: m/z=520.4 [M+H]⁺.

Step 4: In analogy to the synthesis of Intermediate I3A, step 4, tert-butyl ((6R,8R)-8-(2-fluoro-5-((trimethylsilyl)ethynyl)phenyl)-8-methyl-6-(methylimino)-6-oxido-6-thia-9-azaspiro[4.5]dec-9-en-10-yl)carbamate was converted to tert-butyl ((6R,8R)-8-(5-ethynyl-2-fluorophenyl)-8-methyl-6-(methylimino)-6-oxido-6-thia-9-azaspiro[4.5]dec-9-en-10-yl)carbamate by treatment with tetrabutylammonium fluoride in dichloromethane. Colorless solid. MS: m/z=448.3 [M+H]⁺.

Intermediate I11B (6S,8R)-10-amino-8-(2-fluorophenyl)-8-methyl-6-(methylimino)-6-thia-9-azaspiro[4.5]dec-9-ene 6-oxide

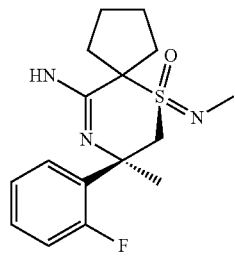 [SMILES: CN=[S@]1(=O)C[C@@](C)(c2ccccc2F)N=C(N)C12CCCC2]

Step 1: In analogy to the synthesis of Intermediates I1A and I1B, step 2, (R)-N-((R)-1-((S)-1-cyano-N-methylcyclopentanesulfonimidoyl)-2-(2-fluorophenyl)propan-2-yl)-2-methylpropane-2-sulfinamide (Intermediate I10B) was converted to 1-((S,2R)-2-amino-2-(2-fluorophenyl)-N-methylpropylsulfonimidoyl)cyclopentanecarbonitrile by treatment with HCl in methanol and dioxane at 0-5° C. Colorless oil. MS: m/z=324.2 [M+H]⁺.

Step 2: In analogy to the synthesis of Intermediate I2A, 1-((S,2R)-2-amino-2-(2-fluorophenyl)-N-methylpropylsulfonimidoyl)cyclopentanecarbonitrile was converted to (6S,8R)-10-amino-8-(2-fluorophenyl)-8-methyl-6-(methylimino)-6-thia-9-azaspiro[4.5]dec-9-ene 6-oxide by treatment with CuCl in ethanol at 75° C. Light brown gum. MS: m/z=324.2 [M+H]⁺.

Intermediate I12B tert-butyl ((6S,8R)-8-(5-ethynyl-2-fluorophenyl)-8-methyl-6-(methylimino)-6-oxido-6-thia-9-azaspiro[4.5]dec-9-en-10-yl)carbamate

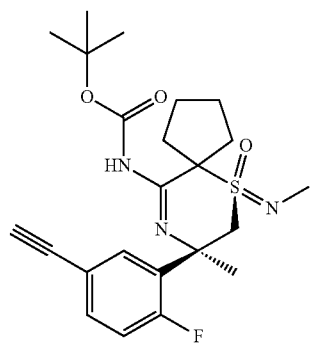 [SMILES: C#Cc1ccc(F)c([C@]2(C)C[S@@](=O)(=NC)C3(CCCC3)C(NC(=O)OC(C)(C)C)=N2)c1]

Step 1: In analogy to the synthesis of Intermediate I3A, step 1, (6S,8R)-10-amino-8-(2-fluorophenyl)-8-methyl-6-(methylimino)-6-thia-9-azaspiro[4.5]dec-9-ene 6-oxide (Intermediate I11B) was converted to (6S,8R)-10-amino-8-(2-fluoro-5-iodophenyl)-8-methyl-6-(methylimino)-6-thia-9-azaspiro[4.5]dec-9-ene 6-oxide by treatment with N-iodosuccinimide in dichloromethane in the presence of trifluoromethanesulfonic acid. Brown gum. MS: m/z=450.1 [M+H]⁺.

Step 2: In analogy to the synthesis of Intermediate I3A, step 2, (6S,8R)-10-amino-8-(2-fluoro-5-iodophenyl)-8-methyl-6-(methylimino)-6-thia-9-azaspiro[4.5]dec-9-ene 6-oxide was converted to tert-butyl ((6S,8R)-8-(2-fluoro-5-iodophenyl)-8-methyl-6-(methylimino)-6-oxido-6-thia-9-azaspiro[4.5]dec-9-en-10-yl)carbamate by treatment with BOC-Anhydride in dichloromethane. Colorless solid. MS: m/z=550.2 [M+H]⁺.

Step 3: In analogy to the synthesis of Intermediate I3A, step 3, tert-butyl ((6S,8R)-8-(2-fluoro-5-iodophenyl)-8-methyl-6-(methylimino)-6-oxido-6-thia-9-azaspiro[4.5]dec-9-en-10-yl)carbamate was converted to tert-butyl ((6S,8R)-8-(2-fluoro-5-((trimethylsilyl)ethynyl)phenyl)-8-methyl-6-(methylimino)-6-oxido-6-thia-9-azaspiro[4.5]dec-9-en-10-yl)carbamate by treatment with ethynyltrimethylsilane in THF in the presence of bis(triphenylphosphine)palladium (II) chloride, copper (I) iodide and triethylamine. Off-white solid. MS: m/z=520.4 [M+H]⁺.

Step 4: In analogy to the synthesis of Intermediate I3A, step 4, tert-butyl ((6S,8R)-8-(2-fluoro-5-((trimethylsilyl)ethynyl)phenyl)-8-methyl-6-(methylimino)-6-oxido-6-thia-9-azaspiro[4.5]dec-9-en-10-yl)carbamate was converted to tert-butyl ((6S,8R)-8-(5-ethynyl-2-fluorophenyl)-8-methyl-6-(methylimino)-6-oxido-6-thia-9-azaspiro[4.5]dec-9-en-10-yl)carbamate by treatment with tetrabutylammonium fluoride in dichloromethane. Colorless solid. MS: m/z=448.3 [M+H]⁺.

Intermediates I14A and I14B tert-butyl N-[(1R,3R)-1-cyclopropylimino-3-(2-fluoro-5-iodophenyl)-3,6,6-trimethyl-1-oxo-2H-1,4-thiazin-5-yl]carbamate (I14A) and tert-butyl N-[(1S,3R)-1-cyclopropylimino-3-(2-fluoro-5-iodophenyl)-3,6,6-trimethyl-1-oxo-2H-1,4-thiazin-5-yl]carbamate (I14B)

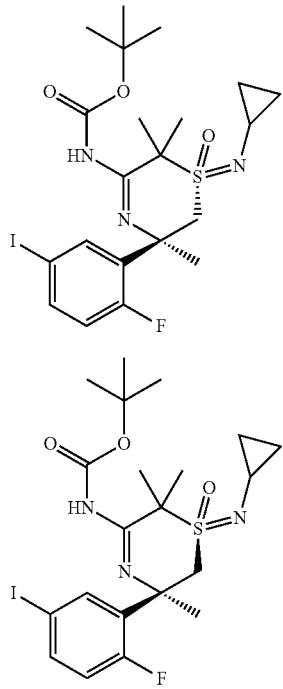

I14A

I14B

Step 1: 1-(2-Fluoro-5-iodophenyl)ethanone (5 g) and (R)-(+)-2-methyl-2-propanesulfinamide (4.59 g) were dissolved in THF (38.6 ml). After addition of titanium(iv) ethoxide (8.64 g) the mixture was stirred at room temperature overnight then heated up to 70° C. and stirred for 5 h. After cooling to room temperature, water (3 ml), ethyl acetate (50) and Dicalite were added and the mixture was stirred for 10 min and filtered. The filtrate was concentrated and the residual liquid oil was purified by chromatography (silica gel, 0% to 60% EtOAc in n-heptane) to give (R)-N-(1-(2-fluoro-5-iodophenyl)ethylidene)-2-methylpropane-2-sulfinamide as light yellow solid. MS: m/z=368.1 [M+H]$^+$.

Step 2: To a stirred solution of 2-methyl-2-(S-methylsulfonimidoyl)propanenitrile (5 g) in 1,2-dichloroethane (33.3 ml) were added cyclopropylboronic acid (6.76 g), copper (II) acetate (6.21 g), 2,2'-bipyridine (4.27 g) and sodium carbonate (10.9 g). The reaction mixture was stirred under air atmosphere for 5 min, then heated up to 90° C. and stirred for 3 h. The reaction mixture was cooled down to room temperature and stirred overnight, filtered through 50 g silica gel-column. The filtrate was concentrated to get the crude product. The product was purified using flash chromatography (silica gel, 0% to 100% EtOAc in n-heptane) to give 2-(N-cyclopropyl-S-methylsulfonimidoyl)-2-methylpropanenitrile as light yellow liquid. MS: m/z=187.1 [M+H].

Step 3: In analogy to the synthesis of Intermediate I4A, 2-(N-cyclopropyl-S-methylsulfonimidoyl)-2-methylpropanenitrile was reacted first with lithium bis(trimethylsilyl)amide followed by treatment with (R)-N-(1-(2-fluoro-5-iodophenyl)ethylidene)-2-methylpropane-2-sulfinamide to give (R)-N-((2R)-1-(2-cyano-N-cyclopropylpropan-2-ylsulfonimidoyl)-2-(2-fluoro-5-iodophenyl)propan-2-yl)-2-methylpropane-2-sulfinamide (mixture of 2 isomers as light yellow oil, MS: m/z=554.3 [M+H]$^+$.

Step 4: In analogy to the synthesis of Intermediates I1A and I1B, step 2, (R)-N-((2R)-1-(2-cyano-N-cyclopropylpropan-2-ylsulfonimidoyl)-2-(2-fluoro-5-iodophenyl)propan-2-yl)-2-methylpropane-2-sulfinamide was converted to 2-((2R)-2-amino-N-cyclopropyl-2-(2-fluoro-5-iodophenyl)propylsulfonimidoyl)-2-methylpropanenitrile (mixture of 2 isomers) by treatment with HCl in methanol and dioxane at 0-5° C. Light yellow oil. MS: m/z=450.3 [M+H]$^+$.

Step 5: In analogy to the synthesis of Intermediate I2A, 2-((2R)-2-amino-N-cyclopropyl-2-(2-fluoro-5-iodophenyl)propylsulfonimidoyl)-2-methylpropanenitrile was converted to (3R)-5-amino-1-(cyclopropylimino)-3-(2-fluoro-5-iodophenyl)-3,6,6-trimethyl-3,6-dihydro-2H-1,4-thiazine 1-oxide (mixture of 2 isomers, not pure) by treatment with CuCl in ethanol. Light green oil. MS: m/z=450.3 [M+H]$^+$.

Step 6: In analogy to the synthesis of Intermediate I3A, step 2, (3R)-5-amino-1-(cyclopropylimino)-3-(2-fluoro-5-iodophenyl)-3,6,6-trimethyl-3,6-dihydro-2H-1,4-thiazine 1-oxide was treated with BOC-anhydride in dichloromethane to give after chromatography (silica gel, 0% to 80% EtOAc in n-heptane) the first-eluting isomer tert-butyl N-[(1R,3R)-1-cyclopropylimino-3-(2-fluoro-5-iodophenyl)-3,6,6-trimethyl-1-oxo-2H-1,4-thiazin-5-yl]carbamate (Intermediate I14A, off-white solid, MS: m/z=550.4 [M+H]$^+$) and the second-eluting isomer tert-butyl N-[(1S,3R)-1-cyclopropylimino-3-(2-fluoro-5-iodophenyl)-3,6,6-trimethyl-1-oxo-2H-1,4-thiazin-5-yl]carbamate (Intermediate I14B, off-white solid, MS: m/z=550.4 [M+H]$^+$)

Intermediate I15A tert-butyl ((1R,5R)-1-(cyclopropylimino)-5-(5-ethynyl-2-fluorophenyl)-2,2,5-trimethyl-1-oxido-5,6-dihydro-2H-1,4-thiazin-3-yl)carbamate

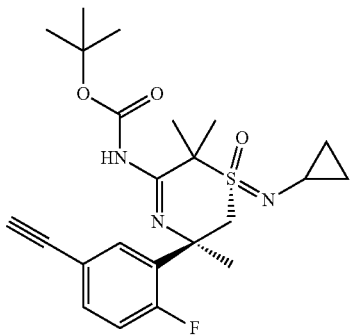 [SMILES: C#Cc1ccc(F)c([C@]2(C)C[S@](=O)(=NC3CC3)C(C)(C)C(NC(=O)OC(C)(C)C)=N2)c1]

Step 1: In analogy to the synthesis of Intermediate I3A, step 3, tert-butyl ((1R,5R)-1-(cyclopropylimino)-5-(2-fluoro-5-iodophenyl)-2,2,5-trimethyl-1-oxido-5,6-dihydro-2H-1,4-thiazin-3-yl)carbamate (Intermediate I14A) was converted to tert-butyl ((1R,5R)-1-(cyclopropylimino)-5-(2-fluoro-5-((trimethylsilyl)ethynyl)phenyl)-2,2,5-trimethyl-1-oxido-5,6-dihydro-2H-1,4-thiazin-3-yl)carbamate by treatment with ethynyltrimethylsilane in THF in the presence of bis(triphenylphosphine)palladium (II) chloride, copper (I) iodide and triethylamine. Yellow solid. MS: m/z=520.5 [M+H]⁺.

Step 2: In analogy to the synthesis of Intermediate I3A, step 4, tert-butyl ((1R,5R)-1-(cyclopropylimino)-5-(2-fluoro-5-((trimethylsilyl)ethynyl)phenyl)-2,2,5-trimethyl-1-oxido-5,6-dihydro-2H-1,4-thiazin-3-yl)carbamate was converted to tert-butyl ((1R,5R)-1-(cyclopropylimino)-5-(5-ethynyl-2-fluorophenyl)-2,2,5-trimethyl-1-oxido-5,6-dihydro-2H-1,4-thiazin-3-yl)carbamate by treatment with tetrabutylammonium fluoride in dichloromethane. Off-white solid. MS: m/z=448.4 [M+H]⁺.

Intermediate I15B tert-butyl ((1S,5R)-1-(cyclopropylimino)-5-(5-ethynyl-2-fluorophenyl)-2,2,5-trimethyl-1-oxido-5,6-dihydro-2H-1,4-thiazin-3-yl)carbamate

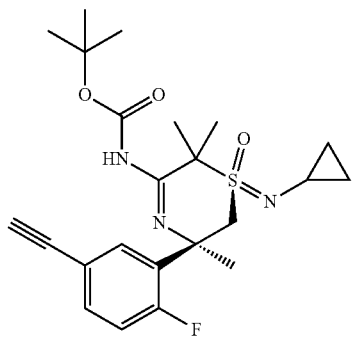 [SMILES: C#Cc1ccc(F)c([C@]2(C)C[S@@](=O)(=NC3CC3)C(C)(C)C(NC(=O)OC(C)(C)C)=N2)c1]

Step 1: In analogy to the synthesis of Intermediate I3A, step 3, tert-butyl ((1S,5R)-1-(cyclopropylimino)-5-(2-fluoro-5-iodophenyl)-2,2,5-trimethyl-1-oxido-5,6-dihydro-2H-1,4-thiazin-3-yl)carbamate (Intermediate I14B) was converted to tert-butyl ((1S,5R)-1-(cyclopropylimino)-5-(2-fluoro-5-((trimethylsilyl)ethynyl)phenyl)-2,2,5-trimethyl-1-oxido-5,6-dihydro-2H-1,4-thiazin-3-yl)carbamate by treatment with ethynyltrimethylsilane in THF in the presence of bis(triphenylphosphine)palladium (II) chloride, copper (I) iodide and triethylamine. Off-white solid. MS: m/z=520.5 [M+H]⁺.

Step 2: In analogy to the synthesis of Intermediate I3A, step 4, tert-butyl ((1S,5R)-1-(cyclopropylimino)-5-(2-fluoro-5-((trimethylsilyl)ethynyl)phenyl)-2,2,5-trimethyl-1-oxido-5,6-dihydro-2H-1,4-thiazin-3-yl)carbamate was converted to tert-butyl ((1S,5R)-1-(cyclopropylimino)-5-(5-ethynyl-2-fluorophenyl)-2,2,5-trimethyl-1-oxido-5,6-dihydro-2H-1,4-thiazin-3-yl)carbamate by treatment with tetrabutylammonium fluoride in dichloromethane. Colorless solid. MS: m/z=448.4 [M+H]⁺.

Intermediates I16A and I16B (R)-N-((R)-1-((S)-2-cyano-N-(2,2,2-trifluoroethyl) propan-2-ylsulfonimidoyl)-2-(2-fluoro-5-iodophenyl)propan-2-yl)-2-methylpropane-2-sulfinamide (I16A) and (R)-N-((R)-1-((R)-2-cyano-N-(2,2,2-trifluoroethyl)propan-2-ylsulfonimidoyl)-2-(2-fluoro-5-iodophenyl)propan-2-yl)-2-methylpropane-2-sulfinamide (I16B)

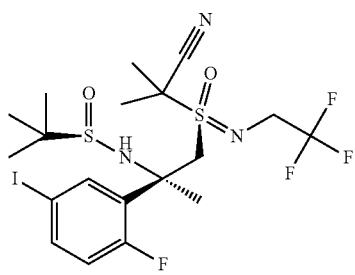

I16A

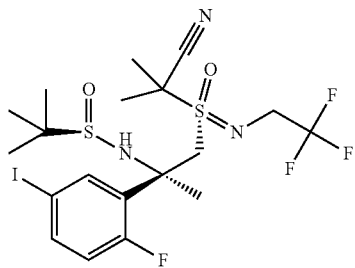

I16A

Step 1: 2-Methyl-2-(S-methylsulfonimidoyl)propanenitrile (250 mg) was dissolved in trifluoroacetic acid (16.3 g) and cooled in an ice-bath. Sodium borohydride (388 mg) was added in one portion. The cooling bath was removed and the mixture was stirred for 3.5 h at room temperature. A second batch of sodium borohydride (259 mg) was added and stirring was continued for 2 h. The mixture was concentrated and taken up in conc. sodium hydrogen carbonate solution and dichloromethane. Additional sodium hydrogen carbonate was added until the pH was >7. After stirring for 5 min, the layers were separated. The aqueous layer was extracted twice more with dichloromethane. The organic layers were dried over sodium sulphate and concentrated. The product was purified using flash chromatography (silica gel, 0% to 100% dichloromethane in n-heptane) to give 2-methyl-2-(S-methyl-N-(2,2,2-trifluoroethyl)sulfonimidoyl)propanenitrile (161 mg) as colorless solid. MS: m/z=229.1 [M+H]⁺.

Step 2: In analogy to the synthesis of Intermediate I4A 2-methyl-2-(S-methyl-N-(2,2,2-trifluoroethyl)sulfonimidoyl)propanenitrile was reacted first with lithium bis(trimethylsilyl)amide followed by treatment with (R)-N-(1-(2-fluoro-5-iodophenyl)ethylidene)-2-methylpropane-2-sulfinamide to give after chromatography (silica gel, 0% to 100% EtOAc in n-heptane) the first-eluting isomer (R)-N-((R)-1-((S)-2-cyano-N-(2,2,2-trifluoroethyl)propan-2-ylsulfonimidoyl)-2-(2-fluoro-5-iodophenyl)propan-2-yl)-2-methylpropane-2-sulfinamide (Intermediate I16A, colorless oil, MS: m/z=596.2 [M+H]⁺) and the second-eluting isomer (R)-N-((R)-1-((R)-2-cyano-N-(2,2,2-trifluoroethyl)propan-2-ylsulfonimidoyl)-2-(2-fluoro-5-iodophenyl)propan-2-yl)-

2-methylpropane-2-sulfinamide (Intermediate I16B, colorless solid, MS: m/z=596.2 [M+H]⁺).

Intermediate I17A tert-butyl ((1S,5R)-5-(2-fluoro-5-iodophenyl)-2,2,5-trimethyl-1-oxido-1-((2,2,2-trifluoroethyl)imino)-5,6-dihydro-2H-1,4-thiazin-3-yl)carbamate

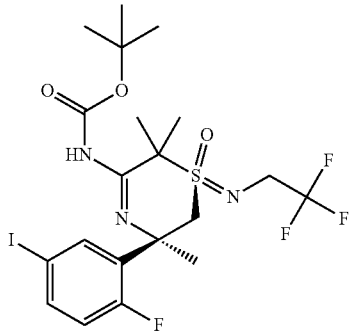 [SMILES: CC(C)(C)OC(=O)NC1=N[C@](C)(c2cc(I)ccc2F)C[S@@](=O)(=NCC(F)(F)F)C1(C)C]

Step 1: In analogy to the synthesis of Intermediates I1A and I1B, step 2, (R)-N-((R)-1-((S)-2-cyano-N-(2,2,2-trifluoroethyl)propan-2-ylsulfonimidoyl)-2-(2-fluoro-5-iodophenyl)propan-2-yl)-2-methylpropane-2-sulfinamide (Intermediate I16A) was converted to 2-((S,2R)-2-amino-2-(2-fluoro-5-iodophenyl)-N-(2,2,2-trifluoroethyl)propylsulfonimidoyl)-2-methylpropanenitrile by treatment with HCl in methanol and dioxane at 0-5° C. Colorless gum. MS: m/z=492.1 [M+H⁺].

Step 2: In analogy to the synthesis of Intermediate I2A, 2-((S,2R)-2-amino-2-(2-fluoro-5-iodophenyl)-N-(2,2,2-trifluoroethyl)propylsulfonimidoyl)-2-methylpropanenitrile was converted to (1S,3R)-5-amino-3-(2-fluoro-5-iodophenyl)-3,6,6-trimethyl-1-((2,2,2-trifluoroethyl)imino)-3,6-dihydro-2H-1,4-thiazine 1-oxide by treatment with CuCl in ethanol. Colorless solid. MS: m/z=492.1 [M+H]⁺.

Step 3: In analogy to the synthesis of Intermediate I3A, step 2, (1S,3R)-5-amino-3-(2-fluoro-5-iodophenyl)-3,6,6-trimethyl-1-((2,2,2-trifluoroethyl)imino)-3,6-dihydro-2H-1,4-thiazine 1-oxide was treated with BOC-anhydride in dichloromethane to give tert-butyl ((1S,5R)-5-(2-fluoro-5-iodophenyl)-2,2,5-trimethyl-1-oxido-1-((2,2,2-trifluoroethyl)imino)-5,6-dihydro-2H-1,4-thiazin-3-yl)carbamate as colorless foam. MS: m/z=592.07 [M+H]⁺

Intermediate I18A tert-butyl ((1S,5R)-5-(5-ethynyl-2-fluorophenyl)-2,2,5-trimethyl-1-oxido-1-((2,2,2-trifluoroethyl)imino)-5,6-dihydro-2H-1,4-thiazin-3-yl)carbamate

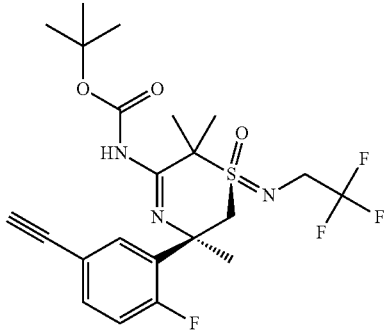 [SMILES: C#Cc1ccc(F)c([C@]2(C)C[S@@](=O)(=NCC(F)(F)F)C(C)(C)C(NC(=O)OC(C)(C)C)=N2)c1]

Step 1: In analogy to the synthesis of Intermediate I3A, step 3, tert-butyl ((1S,5R)-5-(2-fluoro-5-iodophenyl)-2,2,5-trimethyl-1-oxido-1-((2,2,2-trifluoroethyl)imino)-5,6-dihydro-2H-1,4-thiazin-3-yl)carbamate (Intermediate I17A) was converted to tert-butyl ((1S,5R)-5-(2-fluoro-5-((trimethylsilyl)ethynyl)phenyl)-2,2,5-trimethyl-1-oxido-1-((2,2,2-trifluoroethyl)imino)-5,6-dihydro-2H-1,4-thiazin-3-yl)carbamate by treatment with ethynyltrimethylsilane in THF in the presence of bis(triphenylphosphine)palladium (II) chloride, copper (I) iodide and triethylamine. Light brown solid. MS: m/z=560.3 [M–H].

Step 2: In analogy to the synthesis of Intermediate I3A, step 4, tert-butyl ((1S,5R)-5-(2-fluoro-5-((trimethylsilyl)ethynyl)phenyl)-2,2,5-trimethyl-1-oxido-1-((2,2,2-trifluoroethyl)imino)-5,6-dihydro-2H-1,4-thiazin-3-yl)carbamate was converted to tert-butyl ((1S,5R)-5-(5-ethynyl-2-fluorophenyl)-2,2,5-trimethyl-1-oxido-1-((2,2,2-trifluoroethyl)imino)-5,6-dihydro-2H-1,4-thiazin-3-yl)carbamate by treatment with tetrabutylammonium fluoride in dichloromethane. Colorless solid. MS: m/z=488.3 [M–H]⁻.

Intermediate I17B tert-butyl ((1R,5R)-5-(2-fluoro-5-iodophenyl)-2,2,5-trimethyl-1-oxido-1-((2,2,2-trifluoroethyl)imino)-5,6-dihydro-2H-1,4-thiazin-3-yl)carbamate

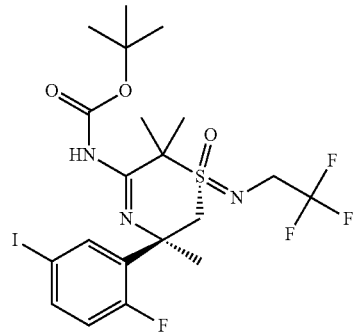 [SMILES: CC(C)(C)OC(=O)NC1=N[C@](C)(c2cc(I)ccc2F)C[S@](=O)(=NCC(F)(F)F)C1(C)C]

Step 1: In analogy to the synthesis of Intermediates I1A and I1B, step 2, (R)-N-((R)-1-((R)-2-cyano-N-(2,2,2-trifluoroethyl)propan-2-ylsulfonimidoyl)-2-(2-fluoro-5-iodophenyl)propan-2-yl)-2-methylpropane-2-sulfinamide (Intermediate I16B) was converted to 2-((R,2R)-2-amino-2-(2-fluoro-5-iodophenyl)-N-(2,2,2-trifluoroethyl)propylsulfonimidoyl)-2-methylpropanenitrile by treatment with HCl in methanol and dioxane at 0-5° C. Colorless oil. MS: m/z=492.1 [M+H]⁺.

Step 2: In analogy to the synthesis of Intermediate I2A, 2-((R,2R)-2-amino-2-(2-fluoro-5-iodophenyl)-N-(2,2,2-trifluoroethyl)propylsulfonimidoyl)-2-methylpropanenitrile was converted to (1R,3R)-5-amino-3-(2-fluoro-5-iodophenyl)-3,6,6-trimethyl-1-((2,2,2-trifluoroethyl)imino)-3,6-dihydro-2H-1,4-thiazine 1-oxide by treatment with CuCl in ethanol. Colorless solid. MS: m/z=492.1 [M+H]⁺.

Step 3: In analogy to the synthesis of Intermediate I3A, step 2, (1R,3R)-5-amino-3-(2-fluoro-5-iodophenyl)-3,6,6-trimethyl-1-((2,2,2-trifluoroethyl)imino)-3,6-dihydro-2H-1,4-thiazine 1-oxide was treated with BOC-anhydride in dichloromethane to give tert-butyl ((1R,5R)-5-(2-fluoro-5-iodophenyl)-2,2,5-trimethyl-1-oxido-1-((2,2,2-trifluoroethyl)imino)-5,6-dihydro-2H-1,4-thiazin-3-yl)carbamate as colorless foam. MS: m/z=590.3 [M–H]⁻

Intermediate I18B tert-butyl ((1R,5R)-5-(5-ethynyl-2-fluorophenyl)-2,2,5-trimethyl-1-oxido-1-((2,2,2-trifluoroethyl)imino)-5,6-dihydro-2H-1,4-thiazin-3-yl)carbamate

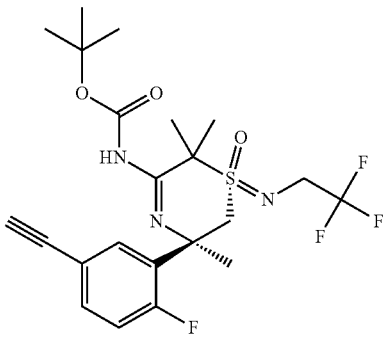 [SMILES: C#Cc1ccc(F)c([C@]2(C)C[S@](=O)(=NCC(F)(F)F)C(C)(C)C(NC(=O)OC(C)(C)C)=N2)c1]

Step 1: In analogy to the synthesis of Intermediate I3A, step 3, tert-butyl ((1R,5R)-5-(2-fluoro-5-iodophenyl)-2,2,5-trimethyl-1-oxido-1-((2,2,2-trifluoroethyl)imino)-5,6-dihydro-2H-1,4-thiazin-3-yl)carbamate (Intermediate I17B) was converted to tert-butyl ((1R,5R)-5-(2-fluoro-5-((trimethylsilyl)ethynyl)phenyl)-2,2,5-trimethyl-1-oxido-1-((2,2,2-trifluoroethyl)imino)-5,6-dihydro-2H-1,4-thiazin-3-yl)carbamate by treatment with ethynyltrimethylsilane in THF in the presence of bis(triphenylphosphine)palladium (II) chloride, copper (I) iodide and triethylamine. Light yellow solid. MS: m/z=560.3 [M–H]⁻.

Step 2: In analogy to the synthesis of Intermediate I3A, step 4, tert-butyl ((1R,5R)-5-(2-fluoro-5-((trimethylsilyl)ethynyl)phenyl)-2,2,5-trimethyl-1-oxido-1-((2,2,2-trifluoroethyl)imino)-5,6-dihydro-2H-1,4-thiazin-3-yl)carbamate was converted to tert-butyl ((1R,5R)-5-(5-ethynyl-2-fluorophenyl)-2,2,5-trimethyl-1-oxido-1-((2,2,2-trifluoroethyl)imino)-5,6-dihydro-2H-1,4-thiazin-3-yl)carbamate by treatment with tetrabutylammonium fluoride in dichloromethane. Light yellow solid. MS: m/z=488.4 [M–H]⁻.

Intermediates I19A and I19B tert-butyl ((1R,5R)-5-(2-fluoro-5-iodophenyl)-1-imino-2,2,5-trimethyl-1-oxido-5,6-dihydro-2H-1,4-thiazin-3-yl)carbamate (I19A) and tert-butyl ((1S,5R)-5-(2-fluoro-5-iodophenyl)-1-imino-2,2,5-trimethyl-1-oxido-5,6-dihydro-2H-1,4-thiazin-3-yl)carbamate (I19B)

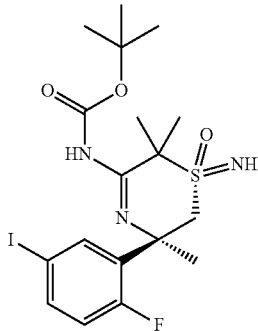

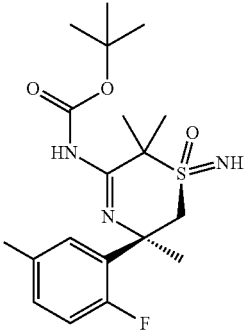

Step 1: In analogy to the synthesis of Intermediate I4A 2-(N-cyclopropyl-S-methylsulfonimidoyl)-2-methylpropanenitrile was reacted first with lithium bis(trimethylsilyl)amide followed by treatment with (R,E)-N-(1-(2-fluorophenyl)ethylidene)-2-methylpropane-2-sulfinamide to give (R)-N-((2R)-1-(2-cyano-N-cyclopropylpropan-2-ylsulfonimidoyl)-2-(2-fluorophenyl)propan-2-yl)-2-methylpropane-2-sulfinamide as a mixture of two isomers. Light yellow oil, MS: m/z=428.4 [M+H]⁺)

Step 2: In analogy to the synthesis of Intermediates I1A and I1B, step 2, (R)-N-((2R)-1-(2-cyano-N-cyclopropylpropan-2-ylsulfonimidoyl)-2-(2-fluorophenyl)propan-2-yl)-2-methylpropane-2-sulfinamide was converted to 2-((2R)-2-amino-N-cyclopropyl-2-(2-fluorophenyl)propylsulfonimidoyl)-2-methylpropanenitrile (mixture of two isomers) by treatment with HCl in methanol and dioxane at 0-5° C. Off-white oil. MS: m/z=324.3 [M+H]⁺.

Step 3: In analogy to the synthesis of Intermediate I2A, 2-((2R)-2-amino-N-cyclopropyl-2-(2-fluorophenyl)propylsulfonimidoyl)-2-methylpropanenitrile was converted to (3R)-5-amino-1-(cyclopropylimino)-3-(2-fluorophenyl)-3,6,6-trimethyl-3,6-dihydro-2H-1,4-thiazine 1-oxide (mixture of two isomers) by treatment with CuCl in ethanol at 75° C. Light green solid. MS: m/z=324.2 [M+H]⁺.

Step 4: In analogy to the synthesis of Intermediate I3A, step 1, (3R)-5-amino-1-(cyclopropylimino)-3-(2-fluorophenyl)-3,6,6-trimethyl-3,6-dihydro-2H-1,4-thiazine 1-oxide was treated with N-iodosuccinimide in dichloromethane in the presence of trifluoromethanesulfonic acid to give as an unexpected product (3R)-5-amino-3-(2-fluoro-5-iodophenyl)-1-imino-3,6,6-trimethyl-3,6-dihydro-2H-1,4-thiazine 1-oxide (mixture of two isomers, could not be obtained pure and was used as a crude product for the next step.)

Step 5: In analogy to the synthesis of Intermediate I3A, step 2, the crude (3R)-5-amino-3-(2-fluoro-5-iodophenyl)-1-imino-3,6,6-trimethyl-3,6-dihydro-2H-1,4-thiazine 1-oxide was treated with BOC-Anhydride in dichloromethane to give after chromatography (silica gel, 0% to 100% EtOAc in n-heptane) the first-eluting isomer tert-butyl ((1R,5R)-5-(2-fluoro-5-iodophenyl)-1-imino-2,2,5-trimethyl-1-oxido-5,6-dihydro-2H-1,4-thiazin-3-yl)carbamate (Intermediate I19A, light brown solid, MS: m/z=510.2 [M+H]⁺) and the second-eluting isomer tert-butyl ((1S,5R)-5-(2-fluoro-5-iodophenyl)-1-imino-2,2,5-trimethyl-1-oxido-5,6-dihydro-2H-1,4-thiazin-3-yl)carbamate (Intermediate I19B, light brown solid, MS: m/z=510.2 [M+H⁺])

Intermediate I20A tert-butyl ((1R,5R)-5-(5-ethynyl-2-fluorophenyl)-1-imino-2,2,5-trimethyl-1-oxido-5,6-dihydro-2H-1,4-thiazin-3-yl)carbamate

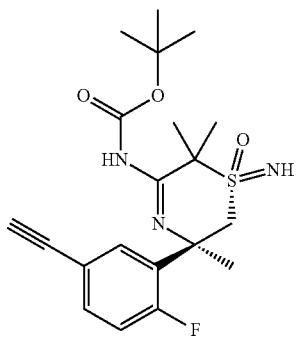 [SMILES: C#Cc1ccc(F)c([C@]2(C)C[S@@](=N)(=O)C(C)(C)C(NC(=O)OC(C)(C)C)=N2)c1]

Step 1: In analogy to the synthesis of Intermediate I3A, step 3, tert-butyl ((1R,5R)-5-(2-fluoro-5-iodophenyl)-1-imino-2,2,5-trimethyl-1-oxido-5,6-dihydro-2H-1,4-thiazin-3-yl)carbamate was converted to tert-butyl ((1R,5R)-5-(2-fluoro-5-((trimethylsilyl)ethynyl)phenyl)-1-imino-2,2,5-trimethyl-1-oxido-5,6-dihydro-2H-1,4-thiazin-3-yl)carbamate by treatment with ethynyltrimethylsilane in THF in the presence of bis(triphenylphosphine)palladium (II) chloride, copper (I) iodide and triethylamine. Off-white solid. MS: m/z=480.3 [M+H]$^+$.

Step 2: In analogy to the synthesis of Intermediate I3A, step 4, tert-butyl ((1R,5R)-5-(2-fluoro-5-((trimethylsilyl)ethynyl)phenyl)-1-imino-2,2,5-trimethyl-1-oxido-5,6-dihydro-2H-1,4-thiazin-3-yl)carbamate was converted to tert-butyl ((1R,5R)-5-(5-ethynyl-2-fluorophenyl)-1-imino-2,2,5-trimethyl-1-oxido-5,6-dihydro-2H-1,4-thiazin-3-yl)carbamate by treatment with tetrabutylammonium fluoride in dichloromethane. Off-white solid. MS: m/z=408.2 [M+H]$^+$.

Intermediate I20B tert-butyl ((1S,5R)-5-(5-ethynyl-2-fluorophenyl)-1-imino-2,2,5-trimethyl-1-oxido-5,6-dihydro-2H-1,4-thiazin-3-yl) carbamate

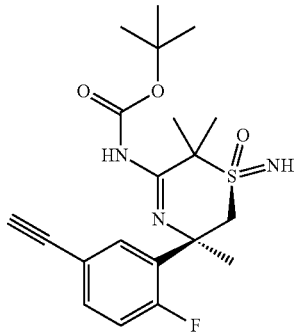 [SMILES: C#Cc1ccc(F)c([C@]2(C)C[S@](=N)(=O)C(C)(C)C(NC(=O)OC(C)(C)C)=N2)c1]

Step 1: In analogy to the synthesis of Intermediate I3A, step 3, tert-butyl ((1S,5R)-5-(2-fluoro-5-iodophenyl)-1-imino-2,2,5-trimethyl-1-oxido-5,6-dihydro-2H-1,4-thiazin-3-yl)carbamate was converted to tert-butyl ((1S,5R)-5-(2-fluoro-5-((trimethylsilyl)ethynyl)phenyl)-1-imino-2,2,5-trimethyl-1-oxido-5,6-dihydro-2H-1,4-thiazin-3-yl)carbamate by treatment with ethynyltrimethylsilane in THF in the presence of bis(triphenylphosphine)palladium (II) chloride, copper (I) iodide and triethylamine. Off-white solid. MS: m/z=480.3 [M+H]$^+$.

Step 2: In analogy to the synthesis of Intermediate I3A, step 4, tert-butyl ((1S,5R)-5-(2-fluoro-5-((trimethylsilyl)ethynyl)phenyl)-1-imino-2,2,5-trimethyl-1-oxido-5,6-dihydro-2H-1,4-thiazin-3-yl)carbamate was converted to tert-butyl ((1S,5R)-5-(5-ethynyl-2-fluorophenyl)-1-imino-2,2,5-trimethyl-1-oxido-5,6-dihydro-2H-1,4-thiazin-3-yl)carbamate by treatment with tetrabutylammonium fluoride in dichloromethane. Off-white solid. MS: m/z=408.2 [M+H]$^+$.

EXPERIMENTAL PART: EXAMPLES

Example 1

(1S,3S)-5-amino-3-(5-(3-(5-chloropyrimidin-2-yl)isoxazol-5-yl)-2-fluorophenyl)-3-(fluoromethyl)-6,6-dimethyl-1-(methylimino)-3,6-dihydro-2H-1,4-thiazine 1-oxide 2,2,2-trifluoroacetate Step 1: 5-Chloropyrimidine-2-carbonitrile (CAS #38275-56-8, 10 g) and hydroxylamine hydrochloride (5.23 g) were combined in Ethanol (107 ml) and stirred for 5 min. Sodium hydroxide (1M in Water, 72.4 ml) was added at room temperature. The mixture was stirred for 35 min. The mixture was diluted with ice and water. The precipitated solid was collected by filtration, washed with cold water and dried to give 5-chloro-N'-hydroxypyrimidine-2-carboximidamide (10.14 g) as colorless solid. MS: m/z=173.0 [M+H]$^+$.

Step 2: To a suspension of 5-chloro-N'-hydroxypyrimidine-2-carboximidamide (5.05 g) in 3.7M aqueous hydrochloric acid (82.3 ml) a solution of sodium nitrite (2.5 g) in water (13.2 ml) was added dropwise while stirring at 0° C. The reaction mixture was stirred at 0° C. for 2 h. The suspension was filtered through sintered glass, the residue was washed with cold water and dried to give 5-chloro-N-hydroxypyrimidine-2-carbimidoyl chloride (4.93) as off-white solid. MS: m/z=192.0 [M+H]$^+$.

Step 3: tert-Butyl ((1S,5S)-5-(5-ethynyl-2-fluorophenyl)-5-(fluoromethyl)-2,2-dimethyl-1-(methylimino)-1-oxido-5,6-dihydro-2H-1,4-thiazin-3-yl)carbamate (Intermediate I3A, 77 mg) was dissolved in THF (3.58 ml) at room temperature under argon. After addition of 5-chloro-N-hydroxypyrimidine-2-carbimidoyl chloride (67.3 mg) and sodium bicarbonate (29.4 mg) the mixture was stirred for 4 days. The mixture was diluted with ethyl acetate, filtered over a 20 g silica-NH2-column, evaporated and purified by chromatography (silica gel, 0% to 100% EtOAc in n-heptane) to give tert-butyl ((1S,5S)-5-(5-(3-(5-chloropyrimidin-2-yl)isoxazol-5-yl)-2-fluorophenyl)-5-(fluoromethyl)-2,2-dimethyl-1-(methylimino)-1-oxido-5,6-dihydro-2H-1,4-thiazin-3-yl)carbamate (83 mg) as off-white solid. MS: m/z=593.3 [M−H].

Step 4: ((1S,5S)-5-(5-(3-(5-chloropyrimidin-2-yl)isoxazol-5-yl)-2-fluorophenyl)-5-(fluoromethyl)-2,2-dimethyl-1-(methylimino)-1-oxido-5,6-dihydro-2H-1,4-thiazin-3-yl)carbamate (80 mg) was combined under argon with dichloromethane (1 ml). Trifluoroacetic acid (920 mg) was added and the mixture was stirred for 2 h. The reaction mixture was evaporated, the residual gum was evaporated with dichloromethane/n-hexane and 4× with n-hexane and dried to give (1S,3S)-5-amino-3-(5-(3-(5-chloropyrimidin-2-yl)isoxazol-5-yl)-2-fluorophenyl)-3-(fluoromethyl)-6,6-dimethyl-1-(methylimino)-3,6-dihydro-2H-1,4-thiazine 1-oxide 2,2,2-trifluoroacetate (81 mg) as colorless solid. MS: m/z=495.1 [M+H$^+$].

Example 2

(1S,3S)-5-amino-3-(2-fluoro-5-(3-(5-methoxypyrazin-2-yl)isoxazol-5-yl)phenyl)-3-(fluoromethyl)-6,6-dimethyl-1-(methylimino)-3,6-dihydro-2H-1,4-thiazine 1-oxide 2,2,2-trifluoroacetate Step 1: In analogy to Example 1, step 2, N'-hydroxy-5-methoxypyrazine-2-carboximidamide (CAS #1344885-60-4) was converted to N-hydroxy-5-methoxypyrazine-2-carbimidoyl chloride by treatment with sodium nitrite in water/HCl at 0° C. Off-white solid. MS: m/z=188.3 [M+H]$^+$.

Step 2: In analogy to Example 1, step 3, tert-butyl ((1S,5S)-5-(5-ethynyl-2-fluorophenyl)-5-(fluoromethyl)-2,2-dimethyl-1-(methylimino)-1-oxido-5,6-dihydro-2H-1,4-thiazin-3-yl)carbamate (Intermediate I3A) was converted to tert-butyl ((1S,5S)-5-(2-fluoro-5-(3-(5-methoxypyrazin-2-yl)isoxazol-5-yl)phenyl)-5-(fluoromethyl)-2,2-dimethyl-1-(methylimino)-1-oxido-5,6-dihydro-2H-1,4-thiazin-3-yl)carbamate by treatment with N-hydroxy-5-methoxypyrazine-2-carbimidoyl chloride in the presence of sodium bicarbonate. Off-white solid. MS: m/z=589.3 [M−H]$^-$.

Step 3: In analogy to Example 1, step 4, tert-butyl ((1S,5S)-5-(2-fluoro-5-(3-(5-methoxypyrazin-2-yl)isoxazol-5-yl)phenyl)-5-(fluoromethyl)-2,2-dimethyl-1-(methylimino)-1-oxido-5,6-dihydro-2H-1,4-thiazin-3-yl)carbamate was converted to (1S,3S)-5-amino-3-(2-fluoro-5-(3-(5-methoxypyrazin-2-yl)isoxazol-5-yl)phenyl)-3-(fluoromethyl)-6,6-dimethyl-1-(methylimino)-3,6-dihydro-2H-1,4-thiazine 1-oxide 2,2,2-trifluoroacetate by treatment with trifluoroacetic acid in dichloromethane. Off-white solid. MS: m/z=491.2 [M+H]$^+$.

Example 3

(1R,3S)-5-amino-3-(5-(3-(5-chloropyrimidin-2-yl)isoxazol-5-yl)-2-fluorophenyl)-3-(fluoromethyl)-6,6-dimethyl-1-(methylimino)-3,6-dihydro-2H-1,4-thiazine 1-oxide 2,2,2-trifluoroacetate Step 1: In analogy to Example 1, step 3, tert-butyl ((1R,5S)-5-(5-ethynyl-2-fluorophenyl)-5-(fluoromethyl)-2,2-dimethyl-1-(methylimino)-1-oxido-5,6-dihydro-2H-1,4-thiazin-3-yl)carbamate (Intermediate I3B) was converted to tert-butyl ((1R,5S)-5-(5-(3-(5-chloropyrimidin-2-yl)isoxazol-5-yl)-2-fluorophenyl)-5-(fluoromethyl)-2,2-dimethyl-1-(methylimino)-1-oxido-5,6-dihydro-2H-1,4-thiazin-3-yl)carbamate by treatment with 5-chloro-N-hydroxypyrimidine-2-carbimidoyl chloride in the presence of sodium bicarbonate. Off-white solid. MS: m/z=593.3 [M−H]$^-$.

Step 2: In analogy to Example 1, step 4, tert-butyl ((1R,5S)-5-(5-(3-(5-chloropyrimidin-2-yl)isoxazol-5-yl)-2-fluorophenyl)-5-(fluoromethyl)-2,2-dimethyl-1-(methylimino)-1-oxido-5,6-dihydro-2H-1,4-thiazin-3-yl)carbamate was converted to (1R,3S)-5-amino-3-(5-(3-(5-chloropyrimidin-2-yl)isoxazol-5-yl)-2-fluorophenyl)-3-(fluoromethyl)-6,6-dimethyl-1-(methylimino)-3,6-dihydro-2H-1,4-thiazine 1-oxide 2,2,2-trifluoroacetate by treatment with trifluoroacetic acid in dichloromethane. Off-white solid. MS: m/z=495.1 [M+H]$^+$.

Example 4

(1R,3S)-5-amino-3-(5-(3-(5-(2,2-difluoroethoxy)pyrazin-2-yl)isoxazol-5-yl)-2-fluorophenyl)-3-(fluoromethyl)-6,6-dimethyl-1-(methylimino)-3,6-dihydro-2H-1,4-thiazine 1-oxide 2,2,2-trifluoroacetate Step 1: In analogy to Example 1, step 1, 5-(2,2-difluoroethoxy)pyrazine-2-carbonitrile (CAS #1544861-08-6) was converted to 5-(2,2-difluoroethoxy)-N'-hydroxypyrazine-2-carboximidamide by treatment with hydroxylamine hydrochloride in the presence of aqueous sodium hydroxide. Off-white solid. MS: m/z=219.1 [M+H]$^+$.

Step 2: In analogy to Example 1, step 2, 5-(2,2-difluoroethoxy)-N'-hydroxypyrazine-2-carboximidamide was converted to 5-(2,2-difluoroethoxy)-N-hydroxypyrazine-2-carbimidoyl chloride by treatment with sodium nitrite in water/HCl at 0° C. Yellow solid.

Step 3: In analogy to Example 1, step 3, tert-butyl ((1R,5S)-5-(5-ethynyl-2-fluorophenyl)-5-(fluoromethyl)-2,2-dimethyl-1-(methylimino)-1-oxido-5,6-dihydro-2H-1,4-thiazin-3-yl)carbamate (Intermediate I3B) was converted to tert-butyl ((1R,5S)-5-(5-(3-(5-(2,2-difluoroethoxy)pyrazin-2-yl)isoxazol-5-yl)-2-fluorophenyl)-5-(fluoromethyl)-2,2-dimethyl-1-(methylimino)-1-oxido-5,6-dihydro-2H-1,4-thiazin-3-yl)carbamate by treatment with 5-(2,2-difluoroethoxy)-N-hydroxypyrazine-2-carbimidoyl chloride in the presence of sodium bicarbonate. Off-white solid. MS: m/z=639.3 [M−H].

Step 4: In analogy to Example 1, step 4, tert-butyl ((1R,5S)-5-(5-(3-(5-(2,2-difluoroethoxy)pyrazin-2-yl)isoxazol-5-yl)-2-fluorophenyl)-5-(fluoromethyl)-2,2-dimethyl-1-(methylimino)-1-oxido-5,6-dihydro-2H-1,4-thiazin-3-yl)carbamate was converted to (1R,3S)-5-amino-3-(5-(3-(5-(2,2-difluoroethoxy)pyrazin-2-yl)isoxazol-5-yl)-2-fluorophenyl)-3-(fluoromethyl)-6,6-dimethyl-1-(methylimino)-3,6-dihydro-2H-1,4-thiazine 1-oxide 2,2,2-trifluoroacetate by treatment with trifluoroacetic acid in dichloromethane. Off-white solid. MS: m/z=541.1 [M+H]$^+$.

Example 5

(1R,3R)-5-amino-3-(5-(3-(5-(2,2-difluoroethoxy)pyrazin-2-yl)isoxazol-5-yl)-2-fluorophenyl)-3,6,6-trimethyl-1-(methylimino)-3,6-dihydro-2H-1,4-thiazine 1-oxide 2,2,2-trifluoroacetate Step 1: In analogy to Example 1, step 3, tert-butyl ((1R,5R)-5-(5-ethynyl-2-fluorophenyl)-2,2,5-trimethyl-1-(methylimino)-1-oxido-5,6-dihydro-2H-1,4-thiazin-3-yl)carbamate (Intermediate I6A) was converted to tert-butyl ((1R,5R)-5-(5-(3-(5-(2,2-difluoroethoxy)pyrazin-2-yl)isoxazol-5-yl)-2-fluorophenyl)-2,2,5-trimethyl-1-(methylimino)-1-oxido-5,6-dihydro-2H-1,4-thiazin-3-yl)carbamate by treatment with 5-(2,2-difluoroethoxy)-N-hydroxypyrazine-2-carbimidoyl chloride in the presence of sodium bicarbonate. Colorless solid. MS: m/z=621.4 [M−H]$^-$.

Step 2: In analogy to Example 1, step 4, tert-butyl ((1R,5R)-5-(5-(3-(5-(2,2-difluoroethoxy)pyrazin-2-yl)isoxazol-5-yl)-2-fluorophenyl)-2,2,5-trimethyl-1-(methylimino)-1-oxido-5,6-dihydro-2H-1,4-thiazin-3-yl)carbamate was converted to (1R,3R)-5-amino-3-(5-(3-(5-(2,2-difluoroethoxy)pyrazin-2-yl)isoxazol-5-yl)-2-fluorophenyl)-3,6, 6-trimethyl-1-(methylimino)-3,6-dihydro-2H-1,4-thiazine 1-oxide 2,2,2-trifluoroacetate by treatment with trifluoroacetic acid in dichloromethane. Off-white solid. MS: m/z=523.2 [M+H]$^+$.

Example 6

(1R,3R)-5-amino-3-(5-(3-(5-chloropyrimidin-2-yl)isoxazol-5-yl)-2-fluorophenyl)-3,6,6-trimethyl-1-(methylimino)-3,6-dihydro-2H-1,4-thiazine 1-oxide 2,2,2-trifluoroacetate Step 1: In analogy to Example 1, step 3, tert-butyl ((1R,5R)-5-(5-ethynyl-2-fluorophenyl)-2,2,5-trimethyl-1-(methylimino)-1-oxido-5,6-dihydro-2H-1,4-thiazin-3-yl)carbamate (Intermediate I6A) was converted to tert-butyl ((1R,5R)-5-(5-(3-(5-chloropyrimidin-2-yl)isoxazol-5-yl)-2-fluorophenyl)-2,2,5-trimethyl-1-(methylimino)-1-oxido-5,6-dihydro-2H-1,4-thiazin-3-yl)carbamate by treatment with 5-chloro-N-hydroxypyrimidine-2-carbimidoyl chloride in the presence of sodium bicarbonate. Colorless solid. MS: m/z=575.3 [M–H]$^−$.

Step 2: In analogy to Example 1, step 4, tert-butyl ((1R,5R)-5-(5-(3-(5-chloropyrimidin-2-yl)isoxazol-5-yl)-2-fluorophenyl)-2,2,5-trimethyl-1-(methylimino)-1-oxido-5,6-dihydro-2H-1,4-thiazin-3-yl)carbamate was converted to (1R,3R)-5-amino-3-(5-(3-(5-chloropyrimidin-2-yl)isoxazol-5-yl)-2-fluorophenyl)-3,6,6-trimethyl-1-(methylimino)-3,6-dihydro-2H-1,4-thiazine 1-oxide 2,2,2-trifluoroacetate by treatment with trifluoroacetic acid in dichloromethane. Off-white solid. MS: m/z=477.1 [M+H$^+$].

Example 7

(1R,3R)-5-amino-3-(2-fluoro-5-(3-(5-methoxypyrazin-2-yl)isoxazol-5-yl)phenyl)-3,6,6-trimethyl-1-(methylimino)-3,6-dihydro-2H-1,4-thiazine 1-oxide 2,2,2-trifluoroacetate Step 1: In analogy to Example 1, step 3, tert-butyl ((1R,5R)-5-(5-ethynyl-2-fluorophenyl)-2,2,5-trimethyl-1-(methylimino)-1-oxido-5,6-dihydro-2H-1,4-thiazin-3-yl)carbamate (Intermediate I6A) was converted to tert-butyl ((1R,5R)-5-(2-fluoro-5-(3-(5-methoxypyrazin-2-yl)isoxazol-5-yl)phenyl)-2,2,5-trimethyl-1-(methylimino)-1-oxido-5,6-dihydro-2H-1,4-thiazin-3-yl)carbamate by treatment with N-hydroxy-5-methoxypyrazine-2-carbimidoyl chloride in the presence of sodium bicarbonate. Colorless solid. MS: m/z=575.3 [M–H]$^−$.

Step 2: In analogy to Example 1, step 4, tert-butyl ((1R,5R)-5-(2-fluoro-5-(3-(5-methoxypyrazin-2-yl)isoxazol-5-yl)phenyl)-2,2,5-trimethyl-1-(methylimino)-1-oxido-5,6-dihydro-2H-1,4-thiazin-3-yl)carbamate was converted to (1R,3R)-5-amino-3-(2-fluoro-5-(3-(5-methoxypyrazin-2-yl)isoxazol-5-yl)phenyl)-3,6,6-trimethyl-1-(methylimino)-3,6-dihydro-2H-1,4-thiazine 1-oxide 2,2,2-trifluoroacetate by treatment with trifluoroacetic acid in dichloromethane. Off-white solid. MS: m/z=473.2 [M+H]$^+$.

Example 8

2-(5-(3-((1R,3R)-5-amino-3,6,6-trimethyl-1-(methylimino)-1-oxido-3,6-dihydro-2H-1,4-thiazin-3-yl)-4-fluorophenyl)isoxazol-3-yl)pyrimidine-5-carbonitrile 2,2,2-trifluoroacetate Step 1: In analogy to Example 1, step 1, pyrimidine-2,5-dicarbonitrile (CAS #38275-58-0) was converted to 5-cyano-N'-hydroxypyrimidine-2-carboximidamide by treatment with hydroxylamine hydrochloride in the presence of aqueous sodium hydroxide. Light brown solid. MS: m/z=164.057 [M+H]$^+$.

Step 2: In analogy to Example 1, step 2, 5-cyano-N'-hydroxypyrimidine-2-carboximidamide was converted to 5-cyano-N-hydroxypyrimidine-2-carbimidoyl chloride by treatment with sodium nitrite in water/HCl at 0° C. Off-white solid.

Step 3: In analogy to Example 1, step 3, tert-butyl ((1R,5R)-5-(5-ethynyl-2-fluorophenyl)-2,2,5-trimethyl-1-(methylimino)-1-oxido-5,6-dihydro-2H-1,4-thiazin-3-yl)carbamate (Intermediate I6A) was converted to tert-butyl ((1R,5R)-5-(5-(3-(5-cyanopyrimidin-2-yl)isoxazol-5-yl)-2-fluorophenyl)-2,2,5-trimethyl-1-(methylimino)-1-oxido-5,6-dihydro-2H-1,4-thiazin-3-yl)carbamate by treatment with 5-cyano-N-hydroxypyrimidine-2-carbimidoyl chloride in the presence of sodium bicarbonate. Colorless solid. MS: m/z=566.3 [M–H]$^−$.

Step 4: In analogy to Example 1, step 4, tert-butyl ((1R,5R)-5-(5-(3-(5-cyanopyrimidin-2-yl)isoxazol-5-yl)-2-fluorophenyl)-2,2,5-trimethyl-1-(methylimino)-1-oxido-5,6-dihydro-2H-1,4-thiazin-3-yl)carbamate was converted to 2-(5-(3-((1R,3R)-5-amino-3,6,6-trimethyl-1-(methylimino)-1-oxido-3,6-dihydro-2H-1,4-thiazin-3-yl)-4-fluorophenyl)isoxazol-3-yl)pyrimidine-5-carbonitrile 2,2,2-trifluoroacetate by treatment with trifluoroacetic acid in dichloromethane. Off-white solid. MS: m/z=468.2 [M+H]$^+$.

Example 9

(1R,3R)-5-amino-3-(5-(1-(5-chloropyridin-2-yl)-1H-1,2,3-triazol-4-yl)-2-fluorophenyl)-3,6,6-trimethyl-1-(methylimino)-3,6-dihydro-2H-1,4-thiazine 1-oxide 2,2,2-trifluoroacetate Step 1: tert-Butyl ((1R,5R)-5-(5-ethynyl-2-fluorophenyl)-2,2,5-trimethyl-1-(methylimino)-1-oxido-5,6-dihydro-2H-1,4-thiazin-3-yl)carbamate (Intermediate I6A, 50 mg) and 2-azido-5-chloropyridine (CAS #242815-95-8, 18.3 mg) were mixed under argon with toluene (1.5 ml). After addition of copper(I) trifluoromethanesulfonate benzene complex (5.97 mg) the reaction mixture was stirred for 2 days at rt in a sealed tube. The mixture was diluted with ethyl acetate, filtered through a glass fiber filter, evaporated and purified by chromatography (silica gel, 0% to 80% EtOAc in n-heptane) to give tert-butyl ((1R,5R)-5-(5-(1-(5-chloropyridin-2-yl)-1H-1,2,3-triazol-4-yl)-2-fluorophenyl)-2,2,5-trimethyl-1-(methylimino)-1-oxido-5,6-dihydro-2H-1,4-thiazin-3-yl)carbamate (49.8 mg) as colorless solid. MS: m/z=574.4 [M–H].

Step 2: In analogy to Example 1, step 4, tert-butyl ((1R,5R)-5-(5-(1-(5-chloropyridin-2-yl)-1H-1,2,3-triazol-4-yl)-2-fluorophenyl)-2,2,5-trimethyl-1-(methylimino)-1-oxido-5,6-dihydro-2H-1,4-thiazin-3-yl)carbamate was converted to (1R,3R)-5-amino-3-(5-(1-(5-chloropyridin-2-yl)-1H-1,2,3-triazol-4-yl)-2-fluorophenyl)-3,6,6-trimethyl-1-(methylimino)-3,6-dihydro-2H-1,4-thiazine 1-oxide 2,2,2-trifluoroacetate by treatment with trifluoroacetic acid in dichloromethane. Off-white solid. MS: m/z=476.1 [M+H]$^+$.

Example 10

6-(4-(3-((1R,3R)-5-amino-3,6,6-trimethyl-1-(methylimino)-1-oxido-3,6-dihydro-2H-1,4-thiazin-3-yl)-4-fluorophenyl)-1H-1,2,3-triazol-1-yl)nicotinonitrile 2,2,2-trifluoroacetate Step 1: In analogy to Example 9, step 1, tert-butyl ((1R,5R)-5-(5-ethynyl-2-fluorophenyl)-2,2,5-trimethyl-1-

(methylimino)-1-oxido-5,6-dihydro-2H-1,4-thiazin-3-yl) carbamate (Intermediate I6A) was converted to tert-butyl ((1R,5R)-5-(5-(1-(5-cyanopyridin-2-yl)-1H-1,2,3-triazol-4-yl)-2-fluorophenyl)-2,2,5-trimethyl-1-(methylimino)-1-oxido-5,6-dihydro-2H-1,4-thiazin-3-yl)carbamate by treatment with 6-azidonicotinonitrile (CAS #1139703-59-5) in the presence of copper(I) trifluoromethanesulfonate benzene complex. Colorless solid. MS: m/z=467.2 [M+H-BOC]$^+$.

Step 2: In analogy to Example 1, step 4, tert-butyl ((1R,5R)-5-(5-(1-(5-cyanopyridin-2-yl)-1H-1,2,3-triazol-4-yl)-2-fluorophenyl)-2,2,5-trimethyl-1-(methylimino)-1-oxido-5,6-dihydro-2H-1,4-thiazin-3-yl)carbamate was converted to 6-(4-(3-((1R,3R)-5-amino-3,6,6-trimethyl-1-(methylimino)-1-oxido-3,6-dihydro-2H-1,4-thiazin-3-yl)-4-fluorophenyl)-1H-1,2,3-triazol-1-yl)nicotinonitrile 2,2,2-trifluoroacetate by treatment with trifluoroacetic acid in dichloromethane. Colorless solid. MS: m/z=467.1 [M+H]$^+$.

Example 11

(1S,3R)-5-amino-3-(5-(3-(5-(2,2-difluoroethoxy) pyrazin-2-yl)isoxazol-5-yl)-2-fluorophenyl)-3,6,6-trimethyl-1-(methylimino)-3,6-dihydro-2H-1,4-thiazine 1-oxide 2,2,2-trifluoroacetate Step 1: In analogy to Example 1, step 3, tert-butyl ((1S,5R)-5-(5-ethynyl-2-fluorophenyl)-2,2,5-trimethyl-1-(methylimino)-1-oxido-5,6-dihydro-2H-1,4-thiazin-3-yl) carbamate (Intermediate I6B) was converted to tert-butyl ((1S,5R)-5-(5-(3-(5-(2,2-difluoroethoxy)pyrazin-2-yl)isoxazol-5-yl)-2-fluorophenyl)-2,2,5-trimethyl-1-(methylimino)-1-oxido-5,6-dihydro-2H-1,4-thiazin-3-yl)carbamate by treatment with 5-(2,2-difluoroethoxy)-N-hydroxypyrazine-2-carbimidoyl chloride in the presence of sodium bicarbonate. Colorless solid. MS: m/z=621.3 [M–H]$^-$.

Step 2: In analogy to Example 1, step 4, tert-butyl ((1S,5R)-5-(5-(3-(5-(2,2-difluoroethoxy)pyrazin-2-yl)isoxazol-5-yl)-2-fluorophenyl)-2,2,5-trimethyl-1-(methylimino)-1-oxido-5,6-dihydro-2H-1,4-thiazin-3-yl)carbamate was converted to (1S,3R)-5-amino-3-(5-(3-(5-(2,2-difluoroethoxy)pyrazin-2-yl)isoxazol-5-yl)-2-fluorophenyl)-3,6,6-trimethyl-1-(methylimino)-3,6-dihydro-2H-1,4-thiazine 1-oxide 2,2,2-trifluoroacetate by treatment with trifluoroacetic acid in dichloromethane. Off-white solid. MS: m/z=523.2 [M+H]$^+$.

Example 12

(1S,3R)-5-amino-3-(5-(3-(5-chloropyrimidin-2-yl) isoxazol-5-yl)-2-fluorophenyl)-3,6,6-trimethyl-1-(methylimino)-3,6-dihydro-2H-1,4-thiazine 1-oxide 2,2,2-trifluoroacetate Step 1: In analogy to Example 1, step 3, tert-butyl ((1S,5R)-5-(5-ethynyl-2-fluorophenyl)-2,2,5-trimethyl-1-(methylimino)-1-oxido-5,6-dihydro-2H-1,4-thiazin-3-yl) carbamate (Intermediate I6B) was converted to tert-butyl ((1S,5R)-5-(5-(3-(5-chloropyrimidin-2-yl)isoxazol-5-yl)-2-fluorophenyl)-2,2,5-trimethyl-1-(methylimino)-1-oxido-5,6-dihydro-2H-1,4-thiazin-3-yl)carbamate by treatment with 5-chloro-N-hydroxypyrimidine-2-carbimidoyl chloride in the presence of sodium bicarbonate. Colorless solid. MS: m/z=575.2 [M–H]$^-$.

Step 2: In analogy to Example 1, step 4, tert-butyl ((1S,5R)-5-(5-(3-(5-chloropyrimidin-2-yl)isoxazol-5-yl)-2-fluorophenyl)-2,2,5-trimethyl-1-(methylimino)-1-oxido-5,6-dihydro-2H-1,4-thiazin-3-yl)carbamate was converted to (1S,3R)-5-amino-3-(5-(3-(5-chloropyrimidin-2-yl)isoxazol-5-yl)-2-fluorophenyl)-3,6,6-trimethyl-1-(methylimino)-3,6-dihydro-2H-1,4-thiazine 1-oxide 2,2,2-trifluoroacetate by treatment with trifluoroacetic acid in dichloromethane. Colorless solid. MS: m/z=477.1 [M+H]$^+$.

Example 13

(1S,3S)-5-amino-3-(2-fluoro-5-(3-(5-methoxypyrimidin-2-yl)isoxazol-5-yl)phenyl)-3-(fluoromethyl)-6,6-dimethyl-1-(methylimino)-3,6-dihydro-2H-1,4-thiazine 1-oxide Step 1: In analogy to Example 1, step 2, N'-hydroxy-5-methoxypyrimidine-2-carboximidamide (CAS #143031-89-4) was converted to N-hydroxy-5-methoxypyrimidine-2-carbimidoyl chloride by treatment with sodium nitrite in water/HCl at 0° C. Off-white solid. MS: m/z=188.1 [M+H]$^+$.

Step 2: In analogy to Example 1, step 3, tert-butyl ((1S,5S)-5-(5-ethynyl-2-fluorophenyl)-5-(fluoromethyl)-2,2-dimethyl-1-(methylimino)-1-oxido-5,6-dihydro-2H-1,4-thiazin-3-yl)carbamate (Intermediate I3A) was converted to tert-butyl ((1S,5S)-5-(2-fluoro-5-(3-(5-methoxypyrimidin-2-yl)isoxazol-5-yl)phenyl)-5-(fluoromethyl)-2,2-dimethyl-1-(methylimino)-1-oxido-5,6-dihydro-2H-1,4-thiazin-3-yl) carbamate by treatment with N-hydroxy-5-methoxypyrimidine-2-carbimidoyl chloride in the presence of sodium bicarbonate. Colorless solid. MS: m/z=589.3 [M–H]$^-$.

Step 3: In analogy to Example 1, step 4, tert-butyl ((1S,5S)-5-(2-fluoro-5-(3-(5-methoxypyrimidin-2-yl)isoxazol-5-yl)phenyl)-5-(fluoromethyl)-2,2-dimethyl-1-(methylimino)-1-oxido-5,6-dihydro-2H-1,4-thiazin-3-yl)carbamate was converted to (1S,3S)-5-amino-3-(2-fluoro-5-(3-(5-methoxypyrimidin-2-yl)isoxazol-5-yl)phenyl)-3-(fluoromethyl)-6,6-dimethyl-1-(methylimino)-3,6-dihydro-2H-1,4-thiazine 1-oxide by treatment with trifluoroacetic acid in dichloromethane. Off-white solid. MS: m/z=491.2 [M+H].

Example 14

6-(4-(3-((1R,3S)-5-amino-3-(fluoromethyl)-6,6-dimethyl-1-(methylimino)-1-oxido-3,6-dihydro-2H-1,4-thiazin-3-yl)-4-fluorophenyl)-1H-1,2,3-triazol-L-yl) nicotinonitrile 2,2,2-trifluoroacetate Step 1: In analogy to Example 9, step 1, tert-butyl ((1R,5S)-5-(5-ethynyl-2-fluorophenyl)-5-(fluoromethyl)-2,2-dimethyl-1-(methylimino)-1-oxido-5,6-dihydro-2H-1,4-thiazin-3-yl)carbamate (Intermediate I3B) was converted to tert-butyl ((1R,5S)-5-(5-(1-(5-cyanopyridin-2-yl)-1H-1,2,3-triazol-4-yl)-2-fluorophenyl)-5-(fluoromethyl)-2,2-dimethyl-1-(methylimino)-1-oxido-5,6-dihydro-2H-1,4-thiazin-3-yl)carbamate by treatment with 6-azidonicotinonitrile (CAS #1139703-59-5) in the presence of copper(I) trifluoromethanesulfonate benzene complex. Colorless solid. MS: m/z=585.2 [M+H]$^+$.

Step 2: In analogy to Example 1, step 4, tert-butyl ((1R,5S)-5-(5-(1-(5-cyanopyridin-2-yl)-1H-1,2,3-triazol-4-yl)-2-fluorophenyl)-5-(fluoromethyl)-2,2-dimethyl-1-(methylimino)-1-oxido-5,6-dihydro-2H-1,4-thiazin-3-yl) carbamate was converted to 6-(4-(3-((1R,3S)-5-amino-3-(fluoromethyl)-6,6-dimethyl-1-(methylimino)-1-oxido-3,6-dihydro-2H-1,4-thiazin-3-yl)-4-fluorophenyl)-1H-1,2,3-triazol-1-yl)nicotinonitrile 2,2,2-trifluoroacetate by treatment with trifluoroacetic acid in dichloromethane. Colorless solid. MS: m/z=485.2 [M+H]⁺.

Example 15

(1R,3S)-5-amino-3-(5-(3-(5-bromo-3-methylpyridin-2-yl)isoxazol-5-yl)-2-fluorophenyl)-3-(fluoromethyl)-6,6-dimethyl-1-(methylimino)-3,6-dihydro-2H-1,4-thiazine 1-oxide 2,2,2-trifluoroacetate Step 1: In analogy to Example 1, step 1, 5-bromo-3-methylpicolinonitrile (CAS #156072-86-5) was converted to 5-bromo-N'-hydroxy-3-methylpicolinimidamide by treatment with hydroxylamine hydrochloride in the presence of aqueous sodium hydroxide. Off-white solid. MS: m/z=230.0 [M+H]⁺.

Step 2: In analogy to Example 1, step 2, 5-bromo-N'-hydroxy-3-methylpicolinimidamide was converted to 5-bromo-N-hydroxy-3-methylpicolinimidoyl chloride by treatment with sodium nitrite in water/HCl at 0° C. Off-white solid.

Step 3: In analogy to Example 1, step 3, tert-butyl ((1R,5S)-5-(5-ethynyl-2-fluorophenyl)-5-(fluoromethyl)-2,2-dimethyl-1-(methylimino)-1-oxido-5,6-dihydro-2H-1,4-thiazin-3-yl)carbamate (Intermediate I3B) was converted to tert-butyl ((1R,5S)-5-(5-(3-(5-bromo-3-methylpyridin-2-yl)isoxazol-5-yl)-2-fluorophenyl)-5-(fluoromethyl)-2,2-dimethyl-1-(methylimino)-1-oxido-5,6-dihydro-2H-1,4-thiazin-3-yl)carbamate by treatment with 5-bromo-N-hydroxy-3-methylpicolinimidoyl chloride in the presence of sodium bicarbonate. Off-white solid. MS: m/z=652.4 [M−H].

Step 4: In analogy to Example 1, step 4, tert-butyl ((1R,5S)-5-(5-(3-(5-bromo-3-methylpyridin-2-yl)isoxazol-5-yl)-2-fluorophenyl)-5-(fluoromethyl)-2,2-dimethyl-1-(methylimino)-1-oxido-5,6-dihydro-2H-1,4-thiazin-3-yl)carbamate was converted to (1R,3S)-5-amino-3-(5-(3-(5-bromo-3-methylpyridin-2-yl)isoxazol-5-yl)-2-fluorophenyl)-3-(fluoromethyl)-6,6-dimethyl-1-(methylimino)-3,6-dihydro-2H-1,4-thiazine 1-oxide 2,2,2-trifluoroacetate by treatment with trifluoroacetic acid in dichloromethane. Off-white solid. MS: m/z=554.1 [M+H]⁺.

Example 16

(1R,3S)-5-amino-3-(5-(1-(5-chloropyridin-2-yl)-1H-1,2,3-triazol-4-yl)-2-fluorophenyl)-3-(fluoromethyl)-6,6-dimethyl-1-(methylimino)-3,6-dihydro-2H-1,4-thiazine 1-oxide 2,2,2-trifluoroacetate Step 1: In analogy to Example 9, step 1, tert-butyl ((1R,5S)-5-(5-ethynyl-2-fluorophenyl)-5-(fluoromethyl)-2,2-dimethyl-1-(methylimino)-1-oxido-5,6-dihydro-2H-1,4-thiazin-3-yl)carbamate (Intermediate I3B) was converted to tert-butyl ((1R,5S)-5-(5-(1-(5-chloropyridin-2-yl)-1H-1,2,3-triazol-4-yl)-2-fluorophenyl)-5-(fluoromethyl)-2,2-dimethyl-1-(methylimino)-1-oxido-5,6-dihydro-2H-1,4-thiazin-3-yl)carbamate by treatment with 2-azido-5-chloropyridine (CAS #242815-95-8) in the presence of copper(I) trifluoromethanesulfonate benzene complex. Colorless solid. MS: m/z=594.2 [M+H]⁺.

Step 2: In analogy to Example 1, step 4, tert-butyl ((1R,5S)-5-(5-(1-(5-chloropyridin-2-yl)-1H-1,2,3-triazol-4-yl)-2-fluorophenyl)-5-(fluoromethyl)-2,2-dimethyl-1-(methylimino)-1-oxido-5,6-dihydro-2H-1,4-thiazin-3-yl)carbamate was converted to (1R,3S)-5-amino-3-(5-(1-(5-chloropyridin-2-yl)-1H-1,2,3-triazol-4-yl)-2-fluorophenyl)-3-(fluoromethyl)-6,6-dimethyl-1-(methylimino)-3,6-dihydro-2H-1,4-thiazine 1-oxide 2,2,2-trifluoroacetate by treatment with trifluoroacetic acid in dichloromethane. Off-white solid. MS: m/z=494.2 [M+H]⁺.

Example 17

(1R,3S)-3-[2-fluoro-5-[3-(5-methoxypyrimidin-2-yl)isoxazol-5-yl]phenyl]-3-(fluoromethyl)-6,6-dimethyl-1-methylimino-1-oxo-2H-1,4-thiazin-5-amine Step 1: In analogy to Example 1, step 3, tert-butyl ((1R,5S)-5-(5-ethynyl-2-fluorophenyl)-5-(fluoromethyl)-2,2-dimethyl-1-(methylimino)-1-oxido-5,6-dihydro-2H-1,4-thiazin-3-yl)carbamate (Intermediate I3B) was converted to tert-butyl ((1R,5S)-5-(2-fluoro-5-(3-(5-methoxypyrimidin-2-yl)isoxazol-5-yl)phenyl)-5-(fluoromethyl)-2,2-dimethyl-1-(methylimino)-1-oxido-5,6-dihydro-2H-1,4-thiazin-3-yl)carbamate by treatment with N-hydroxy-5-methoxypyrimidine-2-carbimidoyl chloride in the presence of sodium bicarbonate. Light yellow solid. MS: m/z=589.3 [M−H]⁻.

Step 2: In analogy to Example 1, step 4, tert-butyl ((1R,5S)-5-(2-fluoro-5-(3-(5-methoxypyrimidin-2-yl)isoxazol-5-yl)phenyl)-5-(fluoromethyl)-2,2-dimethyl-1-(methylimino)-1-oxido-5,6-dihydro-2H-1,4-thiazin-3-yl)carbamate was converted to (1R,3S)-3-[2-fluoro-5-[3-(5-methoxypyrimidin-2-yl)-1,2-oxazol-5-yl]phenyl]-3-(fluoromethyl)-6,6-dimethyl-1-methylimino-1-oxo-2H-1,4-thiazin-5-amine by treatment with trifluoroacetic acid in dichloromethane followed by chromatography over amino-modified silica gel. Colorless solid. MS: m/z=491.2 [M+H⁺].

Example 18

(1R,3R)-3-[5-[3-[5-(2,2-difluoroethoxy)pyrimidin-2-yl]isoxazol-5-yl]-2-fluoro-phenyl]-3,6,6-trimethyl-1-methylimino-1-oxo-2H-1,4-thiazin-5-amine Step 1: To a solution of 2-(methylthio)pyrimidin-5-ol (CAS #4874-33-3, 2 g) in acetone (50 ml) were added potassium carbonate (2.92 g) and 2,2-difluoroethyl trifluoromethanesulfonate (3.46 g) and the mixture was stirred for 3 h at room temperature. Diethyl ether (200 ml) was added and the mixture was filtered. The filtrate was concentrated and the crude material was purified by flash chromatography (silica gel, 0% to 50% EtOAc in n-heptane) to give 5-(2,2-difluoroethoxy)-2-(methylthio)pyrimidine (2.65 g) as light yellow solid. MS: m/z=207.0 [M+H⁺].

Step 2: 5-(2,2-Difluoroethoxy)-2-(methylthio)pyrimidine (2.46 g) was dissolved in dichloromethane (45 ml). After addition of 3-chloroperbenzoic acid (8.02 g) the mixture was stirred for 90 min at room temperature. The mixture was diluted with dichloromethane, washed with aqueous saturated sodium carbonate solution and with water. The organic layer was dried over sodium sulphate and concentrated. The crude product was purified by filtration with dichloromethane through a 50 g silica-NH2 column to give 5-(2,2-difluoroethoxy)-2-(methylsulfonyl)pyrimidine (2.73 g) as colorless solid. MS: m/z=239.1 [M+H]⁺.

Step 3: 5-(2,2-Difluoroethoxy)-2-(methylsulfonyl)pyrimidine (2.31 g) was dissolved in dichloromethane (26.4 ml). After addition of tetrabutylammonium cyanide (3.25 g) the mixture was stirred for 18 h at room temperature. The mixture was evaporated to a smaller volume and directly purified by chromatography (silica gel, dichloromethane) to give 5-(2,2-difluoroethoxy)pyrimidine-2-carbonitrile (2.19 g) as light yellow liquid.

Step 4: In analogy to Example 1, step 1, 5-(2,2-difluoroethoxy)pyrimidine-2-carbonitrile was converted to 5-(2,2-difluoroethoxy)-N'-hydroxypyrimidine-2-carboximidamide by treatment with hydroxylamine hydrochloride in the presence of aqueous sodium hydroxide. Colorless solid. MS: m/z=219.1 [M+H]$^+$.

Step 5: In analogy to Example 1, step 2, 5-(2,2-difluoroethoxy)-N'-hydroxypyrimidine-2-carboximidamide was converted to 5-(2,2-difluoroethoxy)-N-hydroxypyrimidine-2-carbimidoyl chloride by treatment with sodium nitrite in water/HCl at 0° C. Colorless solid.

Step 6: 1-(2-Fluoro-5-hydroxyphenyl)ethanone (6.17 g) and pyridine (6.33 g) were combined with dichloromethane (60 ml) and cooled in an ice bath. Trifluoromethanesulfonic anhydride (13.5 g) was added dropwise. After 15 min the ice bath was removed and the mixture was stirred at room temperature for 1 h. The mixture was again cooled in an ice bath and quenched by addition of sat. NaHCO$_3$ solution and water. The org. phase was separated, washed with water, dried (MgSO$_4$) and filtered. The filtrate was concentrated to dryness and dried to give 3-acetyl-4-fluorophenyl trifluoromethanesulfonate as a light brown liquid. (11.17 g)

Step 7: A solution of 3-acetyl-4-fluorophenyl trifluoromethanesulfonate (5.018 g) in N,N-dimethylformamide (30 ml) and triethylamine (10.9 g) was purged with argon for 10 min. copper (I) iodide (334 mg), trimethylsilylacetylene (3.44 g) and bis(triphenylphosphine)palladium (II) chloride (615 mg) were added and the mixture was heated to 80° C. for 110 min. After cooling to room temperature, water was added and the mixture was extracted with EtOAc. The organic layers were dried (MgSO$_4$), filtered over a plug of SiO$_2$ and concentrated in vacuo. The crude material was purified by flash chromatography (SiO$_2$, 0% to 30% EtOAc in n-heptane) to give 1-(2-fluoro-5-((trimethylsilyl)ethynyl) phenyl)ethanone (4.08 g) as light brown liquid.

Step 8: 1-(2-fluoro-5-((trimethylsilyl)ethynyl)phenyl) ethanone (1 g) was dissolved in dichloromethane (60.1 ml) under argon and cooled to 0° C. After addition of TBAF, (1M in THF, 4.69 ml) the mixture was stirred for 85 min at 0° C. The mixture was diluted with dichloromethane and washed with water. The combined org. layers were dried over sodium sulphate and concentrated. The crude material was purified by flash chromatography (SiO$_2$, 0% to 50% EtOAc in n-heptane) to give 1-(5-ethynyl-2-fluorophenyl) ethanone as light yellow solid (590 mg).

Step 9: In analogy to Example 1, step 3, 1-(5-ethynyl-2-fluorophenyl)ethanone was converted to 1-(5-(3-(5-(2,2-difluoroethoxy)pyrimidin-2-yl)isoxazol-5-yl)-2-fluorophenyl) ethanone by treatment with 5-(2,2-difluoroethoxy)-N-hydroxypyrimidine-2-carbimidoyl chloride in the presence of sodium bicarbonate. Light yellow solid. MS: m/z=364.1 [M+H]$^+$.

Step 10: 1-(5-(3-(5-(2,2-difluoroethoxy)pyrimidin-2-yl) isoxazol-5-yl)-2-fluorophenyl)ethanone (1.15 g) and (R)-(+)-2-methyl-2-propanesulfinamide (767 mg) were dissolved under argon in THF (6.42 ml). After addition of titanium(iv) ethoxide (1.44 g) the reaction mixture was stirred at for 3 weeks. After addition of 0.5 ml water, 25 ml ethyl acetate and Dicalite, the mixture was stirred for 10 min, filtered and rinsed well with ethyl acetate. The filtrate was concentrated and purified by chromatography (SiO$_2$, 0% to 100% EtOAc in n-heptane) to give (R)-N-(1-(5-(3-(5-(2,2-difluoroethoxy)pyrimidin-2-yl)isoxazol-5-yl)-2-fluorophenyl)ethylidene)-2-methylpropane-2-sulfinamide (305 mg) as off-white solid. MS: m/z=467.2 [M+H]$^+$.

Step 11: In analogy to the synthesis of Intermediate I1A, step 1, (R)-N-(1-(5-(3-(5-(2,2-difluoroethoxy)pyrimidin-2-yl)isoxazol-5-yl)-2-fluorophenyl)ethylidene)-2-methylpropane-2-sulfinamide was converted to (R)-N-((2R)-1-(2-cyano-N-methylpropan-2-ylsulfonimidoyl)-2-(5-(3-(5-(2,2-difluoroethoxy)pyrimidin-2-yl)isoxazol-5-yl)-2-fluorophenyl)propan-2-yl)-2-methylpropane-2-sulfinamide by treatment with 2-(N,S-dimethylsulfonimidoyl)-2-methylpropanenitrile (pre-treated with lithium bis(trimethylsilyl) amide). Light yellow solid. MS: m/z=627.1 [M+H]$^+$.

Step 12: In analogy to the synthesis of Intermediate I1A, step 2, (R)-N-((2R)-1-(2-cyano-N-methylpropan-2-ylsulfonimidoyl)-2-(5-(3-(5-(2,2-difluoroethoxy)pyrimidin-2-yl) isoxazol-5-yl)-2-fluorophenyl)propan-2-yl)-2-methylpropane-2-sulfinamide was reacted with HCl in dioxane/methanol to give after chromatography (SiO$_2$, 0% to 100% EtOAc in n-heptane) 2-((2R)-2-amino-2-(5-(3-(5-(2,2-difluoroethoxy)pyrimidin-2-yl)isoxazol-5-yl)-2-fluorophenyl)-N-methylpropylsulfonimidoyl)-2-methylpropanenitrile (first-eluting isomer, off-white solid, MS: m/z=523.2 [M+H]$^+$) and 2-((2R)-2-amino-2-(5-(3-(5-(2,2-difluoroethoxy)pyrimidin-2-yl)isoxazol-5-yl)-2-fluorophenyl)-N-methylpropylsulfonimidoyl)-2-methylpropanenitrile (second-eluting isomer, off-white solid, MS: m/z=523.2 [M+H]$^+$).

Step 13: In analogy to the synthesis of Intermediate I2A, step 1, 2-((2R)-2-amino-2-(5-(3-(5-(2,2-difluoroethoxy)pyrimidin-2-yl)isoxazol-5-yl)-2-fluorophenyl)-N-methylpropylsulfonimidoyl)-2-methylpropanenitrile was treated with copper (I) chloride to give (1R,3R)-3-[5-[3-[5-(2,2-difluoroethoxy)pyrimidin-2-yl]-1,2-oxazol-5-yl]-2-fluorophenyl]-3,6,6-trimethyl-1-methylimino-1-oxo-2H-1,4-thiazin-5-amine as off-white solid, MS: m/z=523.2 [M+H]$^+$.

Example 19

(1S,3R)-3-[5-[3-[5-(2,2-difluoroethoxy)pyrimidin-2-yl]isoxazol-5-yl]-2-fluoro-phenyl]-3,6,6-trimethyl-1-methylimino-1-oxo-2H-1,4-thiazin-5-amine Step 1: In analogy to the synthesis of Intermediate I2A, step 1, 2-((2R)-2-amino-2-(5-(3-(5-(2,2-difluoroethoxy)pyrimidin-2-yl)isoxazol-5-yl)-2-fluorophenyl)-N-methylpropylsulfonimidoyl)-2-methylpropanenitrile was treated with copper (I) chloride to give (1S,3R)-3-[5-[3-[5-(2,2-difluoroethoxy)pyrimidin-2-yl]-1,2-oxazol-5-yl]-2-fluorophenyl]-3,6,6-trimethyl-1-methylimino-1-oxo-2H-1,4-thiazin-5-amine as off-white solid, MS: m/z=523.2 [M+H]$^+$.

Example 20

(1R,3R)-5-amino-3-(2-fluoro-5-(3-(5-methoxypyrimidin-2-yl)isoxazol-5-yl)phenyl)-3,6,6-trimethyl-1-(methylimino)-3,6-dihydro-2H-1,4-thiazine 1-oxide Step 1: In analogy to Example 1, step 3, tert-butyl ((1R,5R)-5-(5-ethynyl-2-fluorophenyl)-2,2,5-trimethyl-1-(methylimino)-1-oxido-5,6-dihydro-2H-1,4-thiazin-3-yl) carbamate (Intermediate I6A) was converted to tert-butyl ((1R,5R)-5-(2-fluoro-5-(3-(5-methoxypyrimidin-2-yl)isoxazol-5-yl)phenyl)-2,2,5-trimethyl-1-(methylimino)-1-oxido-5,6-dihydro-2H-1,4-thiazin-3-yl)carbamate by treatment with N-hydroxy-5-methoxypyrimidine-2-carbimidoyl chloride in the presence of sodium bicarbonate. The product could not be obtained pure and was used directly for the next step.

Step 2: In analogy to Example 1, step 4, tert-butyl ((1R,5R)-5-(2-fluoro-5-(3-(5-methoxypyrimidin-2-yl)isoxazol-5-yl)phenyl)-2,2,5-trimethyl-1-(methylimino)-1-oxido-5,6-dihydro-2H-1,4-thiazin-3-yl)carbamate was converted to (1R,3R)-5-amino-3-(2-fluoro-5-(3-(5-methoxypyrimidin-2-yl)isoxazol-5-yl)phenyl)-3,6,6-trimethyl-1-(methylimino)-3,6-dihydro-2H-1,4-thiazine 1-oxide by treatment with trifluoroacetic acid in dichloromethane. Colorless solid. MS: m/z=473.2 [M+H]$^+$.

Example 21

(1R,3R)-5-amino-3-(2-fluoro-5-(3-(5-(2,2,2-trifluoroethoxy)pyrazin-2-yl)isoxazol-5-yl)phenyl)-3,6,6-trimethyl-1-(methylimino)-3,6-dihydro-2H-1,4-thiazine 1-oxide 2,2,2-trifluoroacetate Step 1: In analogy to Example 1, step 2, N'-hydroxy-5-(2,2,2-trifluoroethoxy)pyrazine-2-carboximidamide (CAS #1344794-41-7) was converted to N-hydroxy-5-(2,2,2-trifluoroethoxy)pyrazine-2-carbimidoyl chloride by treatment with sodium nitrite in water/HCl at 0° C. Off-white solid.

Step 2: In analogy to Example 1, step 3, tert-butyl ((1R,5R)-5-(5-ethynyl-2-fluorophenyl)-2,2,5-trimethyl-1-(methylimino)-1-oxido-5,6-dihydro-2H-1,4-thiazin-3-yl)carbamate (Intermediate I6A) was converted to tert-butyl ((1R,5R)-5-(2-fluoro-5-(3-(5-(2,2,2-trifluoroethoxy)pyrazin-2-yl)isoxazol-5-yl)phenyl)-2,2,5-trimethyl-1-(methylimino)-1-oxido-5,6-dihydro-2H-1,4-thiazin-3-yl)carbamate by treatment with N-hydroxy-5-(2,2,2-trifluoroethoxy)pyrazine-2-carbimidoyl chloride in the presence of sodium bicarbonate. Colorless solid. MS: m/z=639.4 [M−H]$^−$.

Step 3: In analogy to Example 1, step 4, tert-butyl ((1R,5R)-5-(2-fluoro-5-(3-(5-(2,2,2-trifluoroethoxy)pyrazin-2-yl)isoxazol-5-yl)phenyl)-2,2,5-trimethyl-1-(methylimino)-1-oxido-5,6-dihydro-2H-1,4-thiazin-3-yl)carbamate was converted to (1R,3R)-5-amino-3-(2-fluoro-5-(3-(5-(2,2,2-trifluoroethoxy)pyrazin-2-yl)isoxazol-5-yl)phenyl)-3,6,6-trimethyl-1-(methylimino)-3,6-dihydro-2H-1,4-thiazine 1-oxide 2,2,2-trifluoroacetate by treatment with trifluoroacetic acid in dichloromethane. Off-white solid. MS: m/z=541.2 [M+H]$^+$.

Example 22

(1R,3R)-5-amino-3-(5-(3-(5-(cyclopropylmethoxy)pyrazin-2-yl)isoxazol-5-yl)-2-fluorophenyl)-3,6,6-trimethyl-1-(methylimino)-3,6-dihydro-2H-1,4-thiazine 1-oxide Step 1: In analogy to Example 1, step 2, 5-(cyclopropylmethoxy)-N'-hydroxypyrazine-2-carboximidamide (CAS #1344867-87-3) was converted to 5-(cyclopropylmethoxy)-N-hydroxypyrazine-2-carbimidoyl chloride by treatment with sodium nitrite in water/HCl at 0° C. Off-white solid.

Step 2: In analogy to Example 1, step 3, tert-butyl ((1R,5R)-5-(5-ethynyl-2-fluorophenyl)-2,2,5-trimethyl-1-(methylimino)-1-oxido-5,6-dihydro-2H-1,4-thiazin-3-yl)carbamate (Intermediate I6A) was converted to tert-butyl ((1R,5R)-5-(5-(3-(5-(cyclopropylmethoxy)pyrazin-2-yl)isoxazol-5-yl)-2-fluorophenyl)-2,2,5-trimethyl-1-(methylimino)-1-oxido-5,6-dihydro-2H-1,4-thiazin-3-yl)carbamate by treatment with 5-(cyclopropylmethoxy)-N-hydroxypyrazine-2-carbimidoyl chloride in the presence of sodium bicarbonate. Colorless solid. MS: m/z=611.4 [M−H]$^−$.

Step 3: In analogy to Example 1, step 4, tert-butyl ((1R,5R)-5-(5-(3-(5-(cyclopropylmethoxy)pyrazin-2-yl)isoxazol-5-yl)-2-fluorophenyl)-2,2,5-trimethyl-1-(methylimino)-1-oxido-5,6-dihydro-2H-1,4-thiazin-3-yl)carbamate was converted to (1R,3R)-5-amino-3-(5-(3-(5-(cyclopropylmethoxy)pyrazin-2-yl)isoxazol-5-yl)-2-fluorophenyl)-3,6,6-trimethyl-1-(methylimino)-3,6-dihydro-2H-1,4-thiazine 1-oxide by treatment with trifluoroacetic acid in dichloromethane. Off-white solid. MS: m/z=513.3 [M+H]$^+$.

Example 23

(1R,3R)-5-amino-3-(2-fluoro-5-(3-(5-hydroxypyrazin-2-yl)isoxazol-5-yl)phenyl)-3,6,6-trimethyl-1-(methylimino)-3,6-dihydro-2H-1,4-thiazine 1-oxide As a side product in the formation of Example 22, step 3, (1R,3R)-5-amino-3-(2-fluoro-5-(3-(5-hydroxypyrazin-2-yl)isoxazol-5-yl)phenyl)-3,6,6-trimethyl-1-(methylimino)-3,6-dihydro-2H-1,4-thiazine 1-oxide was isolated as off-white solid. MS: m/z=459.2 [M+H]$^+$.

Example 24

(1R,3R)-3-[2-fluoro-5-[3-(5-methoxypyrazin-2-yl)isoxazol-5-yl]phenyl]-3,6,6-trimethyl-1-oxo-1-(trideuteriomethylimino)-2H-1,4-thiazin-5-amine 2,2,2-trifluoroacetate Step 1: In analogy to Example 1, step 3, tert-butyl N-[(1R,3R)-3-(5-ethynyl-2-fluoro-phenyl)-3,6,6-trimethyl-1-oxo-1-(trideuteriomethylimino)-2H-1,4-thiazin-5-yl]carbamate (Intermediate I9A) was converted to tert-butyl N-[(1R,3R)-3-[2-fluoro-5-[3-(5-methoxypyrazin-2-yl)isoxazol-5-yl]phenyl]-3,6,6-trimethyl-1-oxo-1-(trideuteriomethylimino)-2H-1,4-thiazin-5-yl]carbamate by treatment with N-hydroxy-5-methoxypyrazine-2-carbimidoyl chloride in the presence of sodium bicarbonate. Colorless solid. MS: m/z=576.3 [M+H]$^+$.

Step 2: In analogy to Example 1, step 4, tert-butyl N-[(1R,3R)-3-[2-fluoro-5-[3-(5-methoxypyrazin-2-yl)isoxazol-5-yl]phenyl]-3,6,6-trimethyl-1-oxo-1-(trideuteriomethylimino)-2H-1,4-thiazin-5-yl]carbamate was converted to (1R,3R)-3-[2-fluoro-5-[3-(5-methoxypyrazin-2-yl)-1,2-oxazol-5-yl]phenyl]-3,6,6-trimethyl-1-oxo-1-(trideuteriomethylimino)-2H-1,4-thiazin-5-amine 2,2,2-trifluoroacetate by treatment with trifluoroacetic acid in dichloromethane. Off-white solid. MS: m/z=476.3 [M+H]$^+$.

Example 25

(1R,3R)-3-[2-fluoro-5-[3-[5-(2,2,3,3-tetrafluoropropoxy)pyrimidin-2-yl]isoxazol-5-yl]phenyl]-3,6,6-trimethyl-1-oxo-1-(trideuteriomethylimino)-2H-1,4-thiazin-5-amine 2,2,2-trifluoroacetate Step 1: 2-Chloropyrimidin-5-ol (5.3 g) was dissolved under argon in acetone (144 ml). After addition of potassium carbonate (8.42 g) and 2,2,3,3-tetrafluoropropyl trifluoromethanesulfonate (12.3 g) the mixture was stirred for 18 h. The mixture was diluted with ~200 ml ether, stirred for 10 min and filtered. The filtrate was concentrated, taken up in dichloromethane, filtered again and concentrated to dryness to give 2-chloro-5-(2,2,3,3-tetrafluoropropoxy)pyrimidine (8.99 g, not totally pure) as orange oil. MS: m/z=245.0 [M+H]$^+$.

Step 2: 2-Chloro-5-(2,2,3,3-tetrafluoropropoxy)pyrimidine (1.5 g) was dissolved in N,N-dimethylacetamide (25 ml). After addition of zinc cyanide (864 mg) and tetrakis-triphenylphosphin-palladium (709 mg) the mixture was stirred for 45 min at 160° C. under argon.

The mixture was diluted with water, stirred for 5 min and filtered. The filtrate was extracted with EtOAc, the organic layers were washed with water, combined, dried over sodium sulphate and concentrated. The crude material was purified by flash chromatography (silica gel, 0% to 30% EtOAc in n-heptane) to give 5-(2,2,3,3-tetrafluoropropoxy)pyrimidine-2-carbonitrile (944 mg) as colorless oil. MS: m/z=236.1 [M+H]$^+$.

Step 3: In analogy to Example 1, step 1, 5-(2,2,3,3-tetrafluoropropoxy)pyrimidine-2-carbonitrile was converted to N'-hydroxy-5-(2,2,3,3-tetrafluoropropoxy)pyrimidine-2-carboximidamide by treatment with hydroxylamine hydrochloride in the presence of aqueous sodium hydroxide. Colorless solid. MS: m/z=269.1 [M+H]$^+$.

Step 4: In analogy to Example 1, step 2, N'-hydroxy-5-(2,2,3,3-tetrafluoropropoxy)pyrimidine-2-carboximidamide was converted to N-hydroxy-5-(2,2,3,3-tetrafluoropropoxy)pyrimidine-2-carbimidoyl chloride by treatment with sodium nitrite in water/HCl at 0° C. Colorless solid.

Step 5: In analogy to Example 1, step 3, tert-butyl N-[(1R,3R)-3-(5-ethynyl-2-fluoro-phenyl)-3,6,6-trimethyl-1-oxo-1-(trideuteriomethylimino)-2H-1,4-thiazin-5-yl]carbamate (Intermediate I9A) was converted to tert-butyl N-[(1R,3R)-3-[2-fluoro-5-[3-[5-(2,2,3,3-tetrafluoropropoxy)pyrimidin-2-yl]-1,2-oxazol-5-yl]phenyl]-3,6,6-trimethyl-1-oxo-1-(trideuteriomethylimino)-2H-1,4-thiazin-5-yl]carbamate by treatment with N-hydroxy-5-(2,2,3,3-tetrafluoropropoxy)pyrimidine-2-carbimidoyl chloride in the presence of sodium bicarbonate. Colorless solid. MS: m/z=674.5 [M−H]$^−$.

Step 6: In analogy to Example 1, step 4, tert-butyl N-[(1R,3R)-3-[2-fluoro-5-[3-[5-(2,2,3,3-tetrafluoropropoxy)pyrimidin-2-yl]-1,2-oxazol-5-yl]phenyl]-3,6,6-trimethyl-1-oxo-1-(trideuteriomethylimino)-2H-1,4-thiazin-5-yl]carbamate was converted to (1R,3R)-3-[2-fluoro-5-[3-[5-(2,2,3,3-tetrafluoropropoxy)pyrimidin-2-yl]-1,2-oxazol-5-yl]phenyl]-3,6,6-trimethyl-1-oxo-1-(trideuteriomethylimino)-2H-1,4-thiazin-5-amine 2,2,2-trifluoroacetate by treatment with trifluoroacetic acid in dichloromethane. Off-white solid. MS: m/z=576.3 [M+H]$^+$.

Example 26

(1R,3R)-3-[5-[3-(5-ethylpyrimidin-2-yl)isoxazol-5-yl]-2-fluoro-phenyl]-3,6,6-trimethyl-1-oxo-1-(trideuteriomethylimino)-2H-1,4-thiazin-5-amine 2,2,2-trifluoroacetate Step 1: In analogy to Example 1, step 1, 5-ethylpyrimidine-2-carbonitrile (CAS #1622073-68-0) was converted to 5-ethyl-N'-hydroxypyrimidine-2-carboximidamide by treatment with hydroxylamine hydrochloride in the presence of aqueous sodium hydroxide. Off-white solid. MS: m/z=167.1 [M+H]$^+$.

Step 2: In analogy to Example 1, step 2, 5-ethyl-N'-hydroxypyrimidine-2-carboximidamide was converted to 5-ethyl-N-hydroxypyrimidine-2-carbimidoyl chloride by treatment with sodium nitrite in water/HCl at 0° C. Colorless solid. MS: m/z=186.1 [M+H]$^+$.

Step 3: In analogy to Example 1, step 3, tert-butyl N-[(1R,3R)-3-(5-ethynyl-2-fluoro-phenyl)-3,6,6-trimethyl-1-oxo-1-(trideuteriomethylimino)-2H-1,4-thiazin-5-yl]carbamate (Intermediate I9A) was converted to tert-butyl N-[(1R,3R)-3-[5-[3-(5-ethylpyrimidin-2-yl)isoxazol-5-yl]-2-fluoro-phenyl]-3,6,6-trimethyl-1-oxo-1-(trideuteriomethylimino)-2H-1,4-thiazin-5-yl]carbamate by treatment with 5-ethyl-N-hydroxypyrimidine-2-carbimidoyl chloride in the presence of sodium bicarbonate. Off-white solid. MS: m/z=572.5 [M−H]$^−$.

Step 4: In analogy to Example 1, step 4, tert-butyl N-[(1R,3R)-3-[5-[3-(5-ethylpyrimidin-2-yl)isoxazol-5-yl]-2-fluoro-phenyl]-3,6,6-trimethyl-1-oxo-1-(trideuteriomethylimino)-2H-1,4-thiazin-5-yl]carbamate was converted to (1R,3R)-3-[5-[3-(5-ethylpyrimidin-2-yl)-1,2-oxazol-5-yl]-2-fluorophenyl]-3,6,6-trimethyl-1-oxo-1-(trideuteriomethylimino)-2H-1,4-thiazin-5-amine 2,2,2-trifluoroacetate by treatment with trifluoroacetic acid in dichloromethane. Off-white solid. MS: m/z=474.4 [M+H]$^+$].

Example 27

(6R,8R)-10-amino-8-(2-fluoro-5-(3-(5-methoxypyrazin-2-yl)isoxazol-5-yl)phenyl)-8-methyl-6-(methylimino)-6-thia-9-azaspiro[4.5]dec-9-ene 6-oxide 2,2,2-trifluoroacetate Step 1: In analogy to Example 1, step 3, tert-butyl ((6R,8R)-8-(5-ethynyl-2-fluorophenyl)-8-methyl-6-(methylimino)-6-oxido-6-thia-9-azaspiro[4.5]dec-9-en-10-yl)carbamate (Intermediate I12A) was converted to tert-butyl ((6R,8R)-8-(2-fluoro-5-(3-(5-methoxypyrazin-2-yl)isoxazol-5-yl)phenyl)-8-methyl-6-(methylimino)-6-oxido-6-thia-9-azaspiro[4.5]dec-9-en-10-yl)carbamate by treatment with N-hydroxy-5-methoxypyrazine-2-carbimidoyl chloride in the presence of sodium bicarbonate. Colorless solid. MS: m/z=599.3 [M+H]$^+$.

Step 2: In analogy to Example 1, step 4, tert-butyl ((6R,8R)-8-(2-fluoro-5-(3-(5-methoxypyrazin-2-yl)isoxazol-5-yl)phenyl)-8-methyl-6-(methylimino)-6-oxido-6-thia-9-azaspiro[4.5]dec-9-en-10-yl)carbamate was converted to (6R,8R)-10-amino-8-(2-fluoro-5-(3-(5-methoxypyrazin-2-yl)isoxazol-5-yl)phenyl)-8-methyl-6-(methylimino)-6-thia-9-azaspiro[4.5]dec-9-ene 6-oxide 2,2,2-trifluoroacetate by treatment with trifluoroacetic acid in dichloromethane. Light yellow solid. MS: m/z=499.3 [M+H]$^+$].

Example 28

(6R,8R)-10-amino-8-(5-(3-(5-chloropyrimidin-2-yl)isoxazol-5-yl)-2-fluorophenyl)-8-methyl-6-(methylimino)-6-thia-9-azaspiro[4.5]dec-9-ene 6-oxide 2,2,2-trifluoroacetate Step 1: In analogy to Example 1, step 3, tert-butyl ((6R,8R)-8-(5-ethynyl-2-fluorophenyl)-8-methyl-6-(methylimino)-6-oxido-6-thia-9-azaspiro[4.5]dec-9-en-10-yl)carbamate (Intermediate I12A) was converted to tert-butyl ((6R,8R)-8-(5-(3-(5-chloropyrimidin-2-yl)isoxazol-5-yl)-2-fluorophenyl)-8-methyl-6-(methylimino)-6-oxido-6-thia-9-azaspiro[4.5]dec-9-en-10-yl)carbamate by treatment with 5-chloro-N-hydroxypyrimidine-2-carbimidoyl chloride in the presence of sodium bicarbonate. Colorless solid. MS: m/z=603.3 [M+H]$^+$.

Step 2: In analogy to Example 1, step 4, tert-butyl ((6R,8R)-8-(5-(3-(5-chloropyrimidin-2-yl)isoxazol-5-yl)-2- fluorophenyl)-8-methyl-6-(methylimino)-6-oxido-6-thia-9-azaspiro[4.5]dec-9-en-10-yl)carbamate was converted to (6R,8R)-10-amino-8-(5-(3-(5-chloropyrimidin-2-yl)isoxazol-5-yl)-2-fluorophenyl)-8-methyl-6-(methylimino)-6-thia-9-azaspiro[4.5]dec-9-ene 6-oxide 2,2,2-trifluoroacetate by treatment with trifluoroacetic acid in dichloromethane. Colorless solid. MS: m/z=503.2 [M+H]$^+$.

Example 29

(6R,8R)-10-amino-8-(2-fluoro-5-(3-(5-methoxypyrimidin-2-yl)isoxazol-5-yl)phenyl)-8-methyl-6-(methylimino)-6-thia-9-azaspiro[4.5]dec-9-ene 6-oxide 2,2,2-trifluoroacetate Step 1: In analogy to Example 1, step 3, tert-butyl ((6R,8R)-8-(5-ethynyl-2-fluorophenyl)-8-methyl-6-(methylimino)-6-oxido-6-thia-9-azaspiro[4.5]dec-9-en-10-yl)carbamate (Intermediate I12A) was converted to tert-butyl ((6R,8R)-8-(2-fluoro-5-(3-(5-methoxypyrimidin-2-yl)isoxazol-5-yl)phenyl)-8-methyl-6-(methylimino)-6-oxido-6-thia-9-azaspiro[4.5]dec-9-en-10-yl)carbamate by treatment with N-hydroxy-5-methoxypyrimidine-2-carbimidoyl chloride in the presence of sodium bicarbonate. Light yellow solid. MS: m/z=599.4 [M+H]$^+$.

Step 2: In analogy to Example 1, step 4, tert-butyl ((6R,8R)-8-(2-fluoro-5-(3-(5-methoxypyrimidin-2-yl)isoxazol-5-yl)phenyl)-8-methyl-6-(methylimino)-6-oxido-6-thia-9-azaspiro[4.5]dec-9-en-10-yl)carbamate was converted to (6R,8R)-10-amino-8-(2-fluoro-5-(3-(5-methoxypyrimidin-2-yl)isoxazol-5-yl)phenyl)-8-methyl-6-(methylimino)-6-thia-9-azaspiro[4.5]dec-9-ene 6-oxide 2,2,2-trifluoroacetate by treatment with trifluoroacetic acid in dichloromethane. Light yellow solid. MS: m/z=499.3 [M+H]$^+$.

Example 30

(6R,8R)-10-amino-8-(5-(3-(5-(2,2-difluoroethoxy)pyrazin-2-yl)isoxazol-5-yl)-2-fluorophenyl)-8-methyl-6-(methylimino)-6-thia-9-azaspiro[4.5]dec-9-ene 6-oxide Step 1: In analogy to Example 1, step 3, tert-butyl ((6R,8R)-8-(5-ethynyl-2-fluorophenyl)-8-methyl-6-(methylimino)-6-oxido-6-thia-9-azaspiro[4.5]dec-9-en-10-yl)carbamate (Intermediate I12A) was converted to tert-butyl ((6R,8R)-8-(5-(3-(5-(2,2-difluoroethoxy)pyrazin-2-yl)isoxazol-5-yl)-2-fluorophenyl)-8-methyl-6-(methylimino)-6-oxido-6-thia-9-azaspiro[4.5]dec-9-en-10-yl)carbamate by treatment with 5-(2,2-difluoroethoxy)-N-hydroxypyrazine-2-carbimidoyl chloride in the presence of sodium bicarbonate. The product was not obtained pure and was used directly for the next step.

Step 2: In analogy to Example 1, step 4, tert-butyl ((6R,8R)-8-(5-(3-(5-(2,2-difluoroethoxy)pyrazin-2-yl)isoxazol-5-yl)-2-fluorophenyl)-8-methyl-6-(methylimino)-6-oxido-6-thia-9-azaspiro[4.5]dec-9-en-10-yl)carbamate was converted to (6R,8R)-10-amino-8-(5-(3-(5-(2,2-difluoroethoxy)pyrazin-2-yl)isoxazol-5-yl)-2-fluorophenyl)-8-methyl-6-(methylimino)-6-thia-9-azaspiro[4.5]dec-9-ene 6-oxide by treatment with trifluoroacetic acid in dichloromethane. Off-white solid. MS: m/z=549.3 [M+H]$^+$.

Example 31

(6S,8R)-10-amino-8-(5-(3-(5-chloropyrimidin-2-yl)isoxazol-5-yl)-2-fluorophenyl)-8-methyl-6-(methylimino)-6-thia-9-azaspiro[4.5]dec-9-ene 6-oxide 2,2,2-trifluoroacetate Step 1: In analogy to Example 1, step 3, tert-butyl ((6S,8R)-8-(5-ethynyl-2-fluorophenyl)-8-methyl-6-(methylimino)-6-oxido-6-thia-9-azaspiro[4.5]dec-9-en-10-yl)carbamate (Intermediate I12B) was converted to tert-butyl ((6S,8R)-8-(5-(3-(5-chloropyrimidin-2-yl)isoxazol-5-yl)-2-fluorophenyl)-8-methyl-6-(methylimino)-6-oxido-6-thia-9-azaspiro[4.5]dec-9-en-10-yl)carbamate by treatment with 5-chloro-N-hydroxypyrimidine-2-carbimidoyl chloride in the presence of sodium bicarbonate. Colorless solid. MS: m/z=601.5 [M−H]$^-$.

Step 2: In analogy to Example 1, step 4, tert-butyl ((6S,8R)-8-(5-(3-(5-chloropyrimidin-2-yl)isoxazol-5-yl)-2-fluorophenyl)-8-methyl-6-(methylimino)-6-oxido-6-thia-9-azaspiro[4.5]dec-9-en-10-yl)carbamate was converted to (6S,8R)-10-amino-8-(5-(3-(5-chloropyrimidin-2-yl)isoxazol-5-yl)-2-fluorophenyl)-8-methyl-6-(methylimino)-6-thia-9-azaspiro[4.5]dec-9-ene 6-oxide 2,2,2-trifluoroacetate by treatment with trifluoroacetic acid in dichloromethane. Colorless solid. MS: m/z=503.3 [M+H]$^+$.

Example 32

(6S,8R)-10-amino-8-(2-fluoro-5-(3-(5-methoxypyrazin-2-yl)isoxazol-5-yl)phenyl)-8-methyl-6-(methylimino)-6-thia-9-azaspiro[4.5]dec-9-ene 6-oxide 2,2,2-trifluoroacetate Step 1: In analogy to Example 1, step 3, tert-butyl ((6S,8R)-8-(5-ethynyl-2-fluorophenyl)-8-methyl-6-(methylimino)-6-oxido-6-thia-9-azaspiro[4.5]dec-9-en-10-yl)carbamate (Intermediate I12B) was converted to tert-butyl ((6S,8R)-8-(2-fluoro-5-(3-(5-methoxypyrazin-2-yl)isoxazol-5-yl)phenyl)-8-methyl-6-(methylimino)-6-oxido-6-thia-9-azaspiro[4.5]dec-9-en-10-yl)carbamate by treatment with N-hydroxy-5-methoxypyrazine-2-carbimidoyl chloride in the presence of sodium bicarbonate. Colorless solid. MS: m/z=599.3 [M+H]$^+$.

Step 2: In analogy to Example 1, step 4, tert-butyl ((6S,8R)-8-(2-fluoro-5-(3-(5-methoxypyrazin-2-yl)isoxazol-5-yl)phenyl)-8-methyl-6-(methylimino)-6-oxido-6-thia-9-azaspiro[4.5]dec-9-en-10-yl)carbamate was converted to (6S,8R)-10-amino-8-(2-fluoro-5-(3-(5-methoxypyrazin-2-yl)isoxazol-5-yl)phenyl)-8-methyl-6-(methylimino)-6-thia-9-azaspiro[4.5]dec-9-ene 6-oxide 2,2,2-trifluoroacetate by treatment with trifluoroacetic acid in dichloromethane. Colorless solid. MS: m/z=499.3 [M+H]$^+$.

Example 33

(1R,3R)-5-amino-1-(cyclopropylimino)-3-(2-fluoro-5-(3-(5-methoxypyrazin-2-yl)isoxazol-5-yl)phenyl)-3,6,6-trimethyl-3,6-dihydro-2H-1,4-thiazine 1-oxide Step 1: In analogy to Example 1, step 3, tert-butyl ((1R,5R)-1-(cyclopropylimino)-5-(5-ethynyl-2-fluorophenyl)-2,2,5-trimethyl-1-oxido-5,6-dihydro-2H-1,4-thiazin-3-yl)carbamate (Intermediate I15A) was converted to tert-butyl ((1R,5R)-1-(cyclopropylimino)-5-(2-fluoro-5-(3-(5-methoxypyrazin-2-yl)isoxazol-5-yl)phenyl)-2,2,5-trimethyl-1-oxido-5,6-dihydro-2H-1,4-thiazin-3-yl)carbamate by treatment with N-hydroxy-5-methoxypyrazine-2-carbimidoyl chloride in the presence of sodium bicarbonate. Colorless solid. MS: m/z=599.5 [M+H]$^+$.

Step 2: In analogy to Example 1, step 4, tert-butyl ((1R,5R)-1-(cyclopropylimino)-5-(2-fluoro-5-(3-(5-methoxypyrazin-2-yl)isoxazol-5-yl)phenyl)-2,2,5-trimethyl-1-oxido-5,6-dihydro-2H-1,4-thiazin-3-yl)carbamate was converted to (1R,3R)-5-amino-1-(cyclopropylimino)-3-(2-fluoro-5-(3-(5-methoxypyrazin-2-yl)isoxazol-5-yl)phenyl)-3,6,6-trimethyl-3,6-dihydro-2H-1,4-thiazine 1-oxide by treatment with trifluoroacetic acid in dichloromethane. Colorless solid. MS: m/z=499.4 [M+H]$^+$.

Example 34

(1R,3R)-3-[5-[3-(5-chloropyrimidin-2-yl)isoxazol-5-yl]-2-fluoro-phenyl]-1-cyclopropylimino-3,6,6-trimethyl-1-oxo-2H-1,4-thiazin-5-amine 2,2,2-trifluoroacetate Step 1: In analogy to Example 1, step 3, tert-butyl ((1R,5R)-1-(cyclopropylimino)-5-(5-ethynyl-2-fluorophenyl)-2,2,5-trimethyl-1-oxido-5,6-dihydro-2H-1,4-thiazin-3-yl)carbamate (Intermediate I15A) was converted to tert-butyl ((1R,5R)-5-(5-(3-(5-chloropyrimidin-2-yl)isoxazol-5-yl)-2-fluorophenyl)-1-(cyclopropylimino)-2,2,5-trimethyl-1-oxido-5,6-dihydro-2H-1,4-thiazin-3-yl)carbamate by treatment with 5-chloro-N-hydroxypyrimidine-2-carbimidoyl chloride in the presence of sodium bicarbonate. Off-white solid. MS: m/z=601.7 [M–H]$^-$.

Step 2: In analogy to Example 1, step 4, tert-butyl ((1R,5R)-5-(5-(3-(5-chloropyrimidin-2-yl)isoxazol-5-yl)-2-fluorophenyl)-1-(cyclopropylimino)-2,2,5-trimethyl-1-oxido-5,6-dihydro-2H-1,4-thiazin-3-yl)carbamate was converted to (1R,3R)-3-[5-[3-(5-chloropyrimidin-2-yl)-1,2-oxazol-5-yl]-2-fluorophenyl]-1-cyclopropylimino-3,6,6-trimethyl-1-oxo-2H-1,4-thiazin-5-amine;2,2,2-trifluoroacetate by treatment with trifluoroacetic acid in dichloromethane. Colorless solid. MS: m/z=503.4 [M+H]$^+$.

Example 35

(1S,3R)-5-amino-1-(cyclopropylimino)-3-(2-fluoro-5-(3-(5-methoxypyrazin-2-yl)isoxazol-5-yl)phenyl)-3,6,6-trimethyl-3,6-dihydro-2H-1,4-thiazine 1-oxide 2,2,2-trifluoroacetate Step 1: In analogy to Example 1, step 3, tert-butyl ((1S,5R)-1-(cyclopropylimino)-5-(5-ethynyl-2-fluorophenyl)-2,2,5-trimethyl-1-oxido-5,6-dihydro-2H-1,4-thiazin-3-yl)carbamate (Intermediate I15B) was converted to tert-butyl ((1S,5R)-1-(cyclopropylimino)-5-(2-fluoro-5-(3-(5-methoxypyrazin-2-yl)isoxazol-5-yl)phenyl)-2,2,5-trimethyl-1-oxido-5,6-dihydro-2H-1,4-thiazin-3-yl)carbamate by treatment with N-hydroxy-5-methoxypyrazine-2-carbimidoyl chloride in the presence of sodium bicarbonate. Colorless solid. MS: m/z=599.5 [M+H]$^+$.

Step 2: In analogy to Example 1, step 4, tert-butyl ((1S,5R)-1-(cyclopropylimino)-5-(2-fluoro-5-(3-(5-methoxypyrazin-2-yl)isoxazol-5-yl)phenyl)-2,2,5-trimethyl-1-oxido-5,6-dihydro-2H-1,4-thiazin-3-yl)carbamate was converted to (1S,3R)-5-amino-1-(cyclopropylimino)-3-(2-fluoro-5-(3-(5-methoxypyrazin-2-yl)isoxazol-5-yl)phenyl)-3,6,6-trimethyl-3,6-dihydro-2H-1,4-thiazine 1-oxide 2,2,2-trifluoroacetate by treatment with trifluoroacetic acid in dichloromethane. Colorless solid. MS: m/z=499.4 [M+H]$^+$.

Example 36

(1S,3R)-5-amino-3-(5-(3-(5-chloropyrimidin-2-yl)isoxazol-5-yl)-2-fluorophenyl)-1-(cyclopropylimino)-3,6,6-trimethyl-3,6-dihydro-2H-1,4-thiazine 1-oxide 2,2,2-trifluoroacetate Step 1: In analogy to Example 1, step 3, tert-butyl ((1S,5R)-1-(cyclopropylimino)-5-(5-ethynyl-2-fluorophenyl)-2,2,5-trimethyl-1-oxido-5,6-dihydro-2H-1,4-thiazin-3-yl)carbamate (Intermediate I15B) was converted to tert-butyl ((1S,5R)-5-(5-(3-(5-chloropyrimidin-2-yl)isoxazol-5-yl)-2-fluorophenyl)-1-(cyclopropylimino)-2,2,5-trimethyl-1-oxido-5,6-dihydro-2H-1,4-thiazin-3-yl)carbamate by treatment with 5-chloro-N-hydroxypyrimidine-2-carbimidoyl chloride in the presence of sodium bicarbonate. Colorless solid. MS: m/z=601.7 [M–H]$^-$.

Step 2: In analogy to Example 1, step 4, tert-butyl ((1S,5R)-5-(5-(3-(5-chloropyrimidin-2-yl)isoxazol-5-yl)-2-fluorophenyl)-1-(cyclopropylimino)-2,2,5-trimethyl-1-oxido-5,6-dihydro-2H-1,4-thiazin-3-yl)carbamate was converted to (1S,3R)-5-amino-3-(5-(3-(5-chloropyrimidin-2-yl)isoxazol-5-yl)-2-fluorophenyl)-1-(cyclopropylimino)-3,6,6-trimethyl-3,6-dihydro-2H-1,4-thiazine 1-oxide 2,2,2-trifluoroacetate by treatment with trifluoroacetic acid in dichloromethane. Colorless solid. MS: m/z=503.4 [M+H]$^+$.

Example 37

(1S,3R)-5-amino-3-(2-fluoro-5-(3-(5-methoxypyrazin-2-yl)isoxazol-5-yl)phenyl)-3,6,6-trimethyl-1-((2,2,2-trifluoroethyl)imino)-3,6-dihydro-2H-1,4-thiazine 1-oxide 2,2,2-trifluoroacetate Step 1: In analogy to Example 1, step 3, tert-butyl ((1S,5R)-5-(5-ethynyl-2-fluorophenyl)-2,2,5-trimethyl-1-oxido-1-((2,2,2-trifluoroethyl)imino)-5,6-dihydro-2H-1,4-thiazin-3-yl)carbamate (Intermediate I18A) was converted to tert-butyl ((1S,5R)-5-(2-fluoro-5-(3-(5-methoxypyrazin-2-yl)isoxazol-5-yl)phenyl)-2,2,5-trimethyl-1-oxido-1-((2,2,2-trifluoroethyl)imino)-5,6-dihydro-2H-1,4-thiazin-3-yl)carbamate by treatment with N-hydroxy-5-methoxypyrazine-2-carbimidoyl chloride in the presence of sodium bicarbonate. Colorless solid. MS: m/z=639.3 [M–H]$^-$.

Step 2: In analogy to Example 1, step 4, tert-butyl ((1S,5R)-5-(2-fluoro-5-(3-(5-methoxypyrazin-2-yl)isoxazol-5-yl)phenyl)-2,2,5-trimethyl-1-oxido-1-((2,2,2-trifluoroethyl)imino)-5,6-dihydro-2H-1,4-thiazin-3-yl)carbamate was converted to (1S,3R)-5-amino-3-(2-fluoro-5-(3-(5-methoxypyrazin-2-yl)isoxazol-5-yl)phenyl)-3,6,6-trimethyl-1-((2,2,2-trifluoroethyl)imino)-3,6-dihydro-2H-1,4-thiazine 1-oxide 2,2,2-trifluoroacetate by treatment with trifluoroacetic acid in dichloromethane. Off-white solid. MS: m/z=541.2 [M+H]$^+$.

Example 38

(1S,3R)-5-amino-3-(5-(3-(5-chloropyrimidin-2-yl)isoxazol-5-yl)-2-fluorophenyl)-3,6,6-trimethyl-1-((2,2,2-trifluoroethyl)imino)-3,6-dihydro-2H-1,4-thiazine 1-oxide 2,2,2-trifluoroacetate Step 1: In analogy to Example 1, step 3, tert-butyl ((1S,5R)-5-(5-ethynyl-2-fluorophenyl)-2,2,5-trimethyl-1- oxido-1-((2,2,2-trifluoroethyl)imino)-5,6-dihydro-2H-1,4-thiazin-3-yl)carbamate (Intermediate I18A) was converted to tert-butyl ((1S,5R)-5-(5-(3-(5-chloropyrimidin-2-yl)isoxazol-5-yl)-2-fluorophenyl)-2,2,5-trimethyl-1-oxido-1-((2,2,2-trifluoroethyl)imino)-5,6-dihydro-2H-1,4-thiazin-3-yl)carbamate by treatment with 5-chloro-N-hydroxypyrimidine-2-carbimidoyl chloride in the presence of sodium bicarbonate. Colorless solid. MS: m/z=643.3 [M–H].

Step 2: In analogy to Example 1, step 4, tert-butyl ((1S,5R)-5-(5-(3-(5-chloropyrimidin-2-yl)isoxazol-5-yl)-2-fluorophenyl)-2,2,5-trimethyl-1-oxido-1-((2,2,2-trifluoroethyl)imino)-5,6-dihydro-2H-1,4-thiazin-3-yl)carbamate was converted to (1S,3R)-5-amino-3-(5-(3-(5-chloropyrimidin-2-yl)isoxazol-5-yl)-2-fluorophenyl)-3,6,6-trimethyl-1-((2,2,2-trifluoroethyl)imino)-3,6-dihydro-2H-1,4-thiazine 1-oxide 2,2,2-trifluoroacetate by treatment with trifluoroacetic acid in dichloromethane. Colorless solid. MS: m/z=545.1 [M+H]$^+$.

Example 39

(1R,3R)-5-amino-3-(2-fluoro-5-(3-(5-methoxypyrazin-2-yl)isoxazol-5-yl)phenyl)-3,6,6-trimethyl-1-((2,2,2-trifluoroethyl)imino)-3,6-dihydro-2H-1,4-thiazine 1-oxide 2,2,2-trifluoroacetate Step 1: In analogy to Example 1, step 3, tert-butyl ((1R,5R)-5-(5-ethynyl-2-fluorophenyl)-2,2,5-trimethyl-1-oxido-1-((2,2,2-trifluoroethyl)imino)-5,6-dihydro-2H-1,4-thiazin-3-yl)carbamate (Intermediate I18B) was converted to tert-butyl ((1R,5R)-5-(2-fluoro-5-(3-(5-methoxypyrazin-2-yl)isoxazol-5-yl)phenyl)-2,2,5-trimethyl-1-oxido-1-((2,2,2-trifluoroethyl)imino)-5,6-dihydro-2H-1,4-thiazin-3-yl)carbamate by treatment with N-hydroxy-5-methoxypyrazine-2-carbimidoyl chloride in the presence of sodium bicarbonate. Colorless solid. MS: m/z=639.4 [M–H]$^-$.

Step 2: In analogy to Example 1, step 4, tert-butyl ((1R,5R)-5-(2-fluoro-5-(3-(5-methoxypyrazin-2-yl)isoxazol-5-yl)phenyl)-2,2,5-triethyl-1-oxido-1-((2,2,2-trifluoroethyl)imino)-5,6-dihydro-2H-1,4-thiazin-3-yl)carbamate was converted to (1R,3R)-5-amino-3-(2-fluoro-5-(3-(5-methoxypyrazin-2-yl)isoxazol-5-yl)phenyl)-3,6,6-trimethyl-1-((2,2,2-trifluoroethyl)imino)-3,6-dihydro-2H-1,4-thiazine 1-oxide 2,2,2-trifluoroacetate by treatment with trifluoroacetic acid in dichloromethane. Colorless solid. MS: m/z=541.2 [M+H]$^+$.

Example 40

(1R,3R)-5-amino-3-(5-(3-(5-chloropyrimidin-2-yl)isoxazol-5-yl)-2-fluorophenyl)-3,6,6-trimethyl-1-((2,2,2-trifluoroethyl)imino)-3,6-dihydro-2H-1,4-thiazine 1-oxide 2,2,2-trifluoroacetate Step 1: In analogy to Example 1, step 3, tert-butyl ((1R,5R)-5-(5-ethynyl-2-fluorophenyl)-2,2,5-trimethyl-1-oxido-1-((2,2,2-trifluoroethyl)imino)-5,6-dihydro-2H-1,4-thiazin-3-yl)carbamate (Intermediate I18B) was converted to tert-butyl ((1R,5R)-5-(5-(3-(5-chloropyrimidin-2-yl)isoxazol-5-yl)-2-fluorophenyl)-2,2,5-trimethyl-1-oxido-1-((2,2,2-trifluoroethyl)imino)-5,6-dihydro-2H-1,4-thiazin-3-yl)carbamate by treatment with 5-chloro-N-hydroxypyrimidine-2-carbimidoyl chloride in the presence of sodium bicarbonate. Colorless solid. MS: m/z=643.3 [M–H]$^-$.

Step 2: In analogy to Example 1, step 4, tert-butyl ((1R,5R)-5-(5-(3-(5-chloropyrimidin-2-yl)isoxazol-5-yl)-2-fluorophenyl)-2,2,5-trimethyl-1-oxido-1-((2,2,2-trifluoroethyl)imino)-5,6-dihydro-2H-1,4-thiazin-3-yl)carbamate was converted to (1R,3R)-5-amino-3-(5-(3-(5-chloropyrimidin-2-yl)isoxazol-5-yl)-2-fluorophenyl)-3,6,6-trimethyl-1-((2,2,2-trifluoroethyl)imino)-3,6-dihydro-2H-1,4-thiazine 1-oxide 2,2,2-trifluoroacetate by treatment with trifluoroacetic acid in dichloromethane. Off-white solid. MS: m/z=545.2 [M+H]$^+$.

Example 41

(1R,3R)-5-amino-3-(2-fluoro-5-(3-(5-methoxypyrazin-2-yl)isoxazol-5-yl)phenyl)-1-imino-3,6,6-trimethyl-3,6-dihydro-2H-1,4-thiazine 1-oxide Step 1: In analogy to Example 1, step 3, tert-butyl ((1R,5R)-5-(5-ethynyl-2-fluorophenyl)-1-imino-2,2,5-trimethyl-1-oxido-5,6-dihydro-2H-1,4-thiazin-3-yl)carbamate (Intermediate I20A) was converted to tert-butyl ((1R,5R)-5-(2-fluoro-5-(3-(5-methoxypyrazin-2-yl)isoxazol-5-yl)phenyl)-1-imino-2,2,5-trimethyl-1-oxido-5,6-dihydro-2H-1,4-thiazin-3-yl)carbamate by treatment with N-hydroxy-5-methoxypyrazine-2-carbimidoyl chloride in the presence of sodium bicarbonate. Off-white solid. MS: m/z=559.3 [M+H].

Step 2: In analogy to Example 1, step 4, tert-butyl ((1R,5R)-5-(2-fluoro-5-(3-(5-methoxypyrazin-2-yl)isoxazol-5-yl)phenyl)-1-imino-2,2,5-trimethyl-1-oxido-5,6-dihydro-2H-1,4-thiazin-3-yl)carbamate was converted to (1R,3R)-5-amino-3-(2-fluoro-5-(3-(5-methoxypyrazin-2-yl)isoxazol-5-yl)phenyl)-1-imino-3,6,6-trimethyl-3,6-dihydro-2H-1,4-thiazine 1-oxide by treatment with trifluoroacetic acid in dichloromethane. Off-white solid. MS: m/z=459.3 [M+H]$^+$.

Example 42

(1R,3R)-3-[5-[3-(5-chloropyrimidin-2-yl)isoxazol-5-yl]-2-fluoro-phenyl]-1-imino-3,6,6-trimethyl-1-oxo-2H-1,4-thiazin-5-amine;2,2,2-trifluoroacetic acid 2,2,2-trifluoroacetate Step 1: In analogy to Example 1, step 3, tert-butyl ((1R,5R)-5-(5-ethynyl-2-fluorophenyl)-1-imino-2,2,5-trimethyl-1-oxido-5,6-dihydro-2H-1,4-thiazin-3-yl)carbamate (Intermediate I20A) was converted to tert-butyl ((1R,5R)-5-(5-(3-(5-chloropyrimidin-2-yl)isoxazol-5-yl)-2-fluorophenyl)-1-imino-2,2,5-trimethyl-1-oxido-5,6-dihydro-2H-1,4-thiazin-3-yl)carbamate by treatment with 5-chloro-N-hydroxypyrimidine-2-carbimidoyl chloride in the presence of sodium bicarbonate. Off-white solid. MS: m/z=561.5 [M–H]$^-$.

Step 2: In analogy to Example 1, step 4, tert-butyl ((1R,5R)-5-(5-(3-(5-chloropyrimidin-2-yl)isoxazol-5-yl)-2-fluorophenyl)-1-imino-2,2,5-trimethyl-1-oxido-5,6-dihydro-2H-1,4-thiazin-3-yl)carbamate was converted to (1R,3R)-3-[5-[3-(5-chloropyrimidin-2-yl)-1,2-oxazol-5-yl]-2-fluorophenyl]-1-imino-3,6,6-trimethyl-1-oxo-2H-1,4-thiazin-5-amine 2,2,2-trifluoroacetate by treatment with trifluoroacetic acid in dichloromethane. Off-white solid. MS: m/z=463.3 [M+H]$^+$.

Example 43

(1S,3R)-3-[2-fluoro-5-[3-(5-methoxypyrazin-2-yl)isoxazol-5-yl]phenyl]-1-imino-3,6,6-trimethyl-1-oxo-2H-1,4-thiazin-5-amine 2,2,2-trifluoroacetate Step 1: In analogy to Example 1, step 3, tert-butyl ((1S,5R)-5-(5-ethynyl-2-fluorophenyl)-1-imino-2,2,5-trimethyl-1-oxido-5,6-dihydro-2H-1,4-thiazin-3-yl)carbamate (Intermediate I20B) was converted to tert-butyl ((1S,5R)-5-(2-fluoro-5-(3-(5-methoxypyrazin-2-yl)isoxazol-5-yl)phenyl)-1-imino-2,2,5-trimethyl-1-oxido-5,6-dihydro-2H-1,4-thiazin-3-yl)carbamate by treatment with N-hydroxy-5-methoxypyrazine-2-carbimidoyl chloride in the presence of sodium bicarbonate. Off-white solid. MS: m/z=557.5 [M−H]$^-$.

Step 2: In analogy to Example 1, step 4, tert-butyl ((1S,5R)-5-(2-fluoro-5-(3-(5-methoxypyrazin-2-yl)isoxazol-5-yl)phenyl)-1-imino-2,2,5-trimethyl-1-oxido-5,6-dihydro-2H-1,4-thiazin-3-yl)carbamate was converted to (1S,3R)-3-[2-fluoro-5-[3-(5-methoxypyrazin-2-yl)-1,2-oxazol-5-yl]phenyl]-1-imino-3,6,6-trimethyl-1-oxo-2H-1,4-thiazin-5-amine 2,2,2-trifluoroacetate by treatment with trifluoroacetic acid in dichloromethane. Off-white solid. MS: m/z=459.3 [M+H]$^+$.

Example 44

(1S,3R)-3-[5-[3-(5-chloropyrimidin-2-yl)isoxazol-5-yl]-2-fluoro-phenyl]-1-imino-3,6,6-trimethyl-1-oxo-2H-1,4-thiazin-5-amine 2,2,2-trifluoroacetate Step 1: In analogy to Example 1, step 3, tert-butyl ((1S,5R)-5-(5-ethynyl-2-fluorophenyl)-1-imino-2,2,5-trimethyl-1-oxido-5,6-dihydro-2H-1,4-thiazin-3-yl)carbamate (Intermediate I20B) was converted to tert-butyl ((1S,5R)-5-(5-(3-(5-chloropyrimidin-2-yl)isoxazol-5-yl)-2-fluorophenyl)-1-imino-2,2,5-trimethyl-1-oxido-5,6-dihydro-2H-1,4-thiazin-3-yl)carbamate by treatment with 5-chloro-N-hydroxypyrimidine-2-carbimidoyl chloride in the presence of sodium bicarbonate. Off-white solid. MS: m/z=561.5 [M−H]$^-$.

Step 2: In analogy to Example 1, step 4, tert-butyl ((1S,5R)-5-(5-(3-(5-chloropyrimidin-2-yl)isoxazol-5-yl)-2-fluorophenyl)-1-imino-2,2,5-trimethyl-1-oxido-5,6-dihydro-2H-1,4-thiazin-3-yl)carbamate was converted to (1S,3R)-3-[5-[3-(5-chloropyrimidin-2-yl)-1,2-oxazol-5-yl]-2-fluorophenyl]-1-imino-3,6,6-trimethyl-1-oxo-2H-1,4-thiazin-5-amine 2,2,2-trifluoroacetate by treatment with trifluoroacetic acid in dichloromethane. Off-white solid. MS: m/z=463.3 [M+H]$^+$.

The invention claimed is:

1. A compound of formula I:

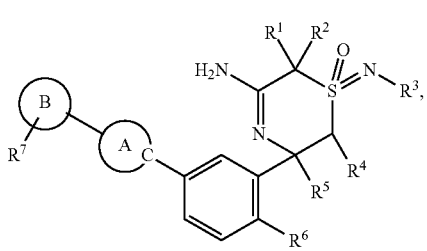

wherein:
A is a 5-membered heteroaryl group;
B is a 6-membered heteroaryl group;
$R^1$ is selected from the group consisting of
  i) $C_{1-6}$-alkyl and
  ii) halogen-$C_{1-6}$-alkyl;
$R^2$ is selected from the group consisting of
  i) $C_{1-6}$-alkyl, and
  ii) halogen-$C_{1-6}$-alkyl;
or $R^1$ and $R^2$ form together with the C-atom they are attached to, a $C_{3-6}$-cycloalkyl-, wherein the $C_{3-6}$-cycloalkyl- is optionally substituted by one or more substituents selected from the group consisting of halogen and hydroxyl;
$R^3$ is selected from the group consisting of
  i) hydrogen,
  ii) $C_{3-6}$-cycloalkyl,
  iii) halogen-$C_{1-6}$-alkyl, and
  iv) $C_{1-6}$-alkyl;
$R^4$ is selected from the group consisting of
  i) hydrogen, and
  ii) $C_{1-6}$-alkyl;
$R^5$ is selected from the group consisting of
  i) $C_{1-6}$-alkyl, and
  ii) halogen-$C_{1-6}$-alkyl;
$R^6$ is fluorine;
$R^7$ is selected from the group consisting of
  i) amino,
  ii) cyano,
  iii) hydrogen,
  iv) OH,
  v) halogen,
  vi) $C_{1-6}$-alkyl,
  vii) $C_{1-6}$-alkyl-$C_{3-6}$-cycloalkyl,
  viii) halogen-$C_{1-6}$-alkyl,
  ix) $C_{1-6}$-alkoxy-$C_{1-6}$-alkyl,
  x) $C_{2-6}$-alkynyl,
  xi) $C_{2-6}$-alkynyl-$C_{1-6}$-alkyl,
  xii) $C_{2-6}$-alkynyl-$C_{1-6}$-alkoxy
  xiii) $C_{1-6}$-alkoxy, and
  xiv) halogen-$C_{1-6}$-alkoxy;
or a pharmaceutically acceptable salt thereof.

2. A compound according to claim 1, wherein
A is a 5-membered heteroaryl group;
B is a 6-membered heteroaryl group;
$R^1$ is selected from the group consisting of
  i) $C_{1-6}$-alkyl and
  ii) halogen-$C_{1-6}$-alkyl;
$R^2$ is selected from the group consisting of
  i) $C_{1-6}$-alkyl, and
  ii) halogen-$C_{1-6}$-alkyl;
or $R^1$ and $R^2$ form together with the C-atom they are attached to a $C_{3-6}$-cycloalkyl-, wherein the $C_{3-6}$-cycloalkyl- is optionally substituted by one or more substituents selected from the group consisting of halogen and hydroxyl;
$R^3$ is selected from the group consisting of
  i) hydrogen,
  ii) halogen-$C_{1-6}$-alkyl, and
  iii) $C_{1-6}$-alkyl;
$R^4$ is selected from the group consisting of
  i) hydrogen, and
  ii) $C_{1-6}$-alkyl;
$R^5$ is selected from the group consisting of
  i) $C_{1-6}$-alkyl, and
  ii) halogen-$C_{1-6}$-alkyl;
$R^6$ is fluorine;
$R^7$ is selected from the group consisting of
  i) amino,
  ii) cyano,
  iii) hydrogen,
  iv) halogen,
  v) $C_{1-6}$-alkyl,
  vi) halogen-$C_{1-6}$-alkyl,
  vii) $C_{1-6}$-alkoxy-$C_{1-6}$-alkyl,
  viii) $C_{2-6}$-alkynyl, ix) $C_{2-6}$-alkynyl-$C_{1-6}$-alkyl,
x) $C_{2-6}$-alkynyl-$C_{1-6}$-alkoxy
xi) $C_{1-6}$-alkoxy, and
xii) halogen-$C_{1-6}$-alkoxy;
or a pharmaceutically acceptable salt thereof.

3. The compound according to claim 1, which is of formula Ia, wherein A, B, $R^1$, $R^2$, $R^3$, $R^4$, $R^5$, $R^6$ and $R^7$ is as defined in claim 1

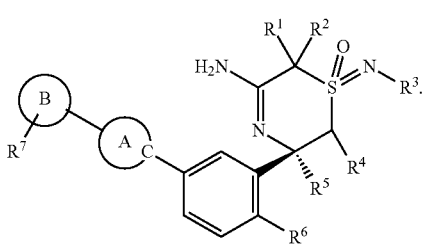

Ia

4. The compound according to claim 1, wherein A is independently isoxazolyl or triazolyl; and B is independently pyrazinyl, pyrimidinyl, or pyridinyl.

5. The compound according to claim 1, wherein $R^1$ is $C_{1-6}$-alkyl.

6. The compound according to claim 1, wherein $R^1$ is methyl.

7. The compound according to claim 1, wherein $R^2$ is $C_{1-6}$-alkyl.

8. The compound according to claim 1, wherein $R^2$ is methyl.

9. The compound according to claim 1, wherein $R^1$ and $R^2$ form together with the C-atom they are attached to a $C_{3-6}$-cycloalkyl-.

10. The compound according to claim 1, wherein $R^1$ and $R^2$ form together with the C-atom they are attached to a cyclopentyl.

11. The compound according to claim 1, wherein $R^3$ is H, $CH_3$, $CD_3$, $CH_2CF_3$ or cyclopropyl.

12. The compound according to claim 1, wherein $R^3$ is $C_{1-6}$-alkyl.

13. The compound according to claim 1, wherein $R^3$ is methyl.

14. The compound according to claim 1, wherein $R^4$ is hydrogen.

15. The compound according to claim 1, wherein $R^5$ is $C_{1-6}$-alkyl or halogen-$C_{1-6}$-alkyl.

16. The compound according to claim 1, wherein $R^5$ is methyl or —$CH_2F$.

17. The compound according to claim 1, wherein $R^7$ is Br, $CH_2$-cyclopropyl, Cl, CN, Et, Me, $OCH_2CF_2CHF_2$, $OCH_2CF_3$, $OCH_2CHF_2$, OH or OMe.

18. A pharmaceutical composition, comprising a therapeutically effective amount of a compound according to claim 1, or a pharmaceutically acceptable salt thereof, and a pharmaceutically acceptable carrier or excipient.

19. A method of treating Alzheimer's Disease, comprising the step of administering a therapeutically effective amount of a compound according to claim 1, or a pharmaceutically acceptable salt thereof, to a patient in need thereof.

* * * * *